US006271362B1

(12) United States Patent
Morikawa et al.

(10) Patent No.: US 6,271,362 B1
(45) Date of Patent: *Aug. 7, 2001

(54) GENE ENCODING IGG FC REGION-BINDING PROTEIN

(75) Inventors: Minoru Morikawa, Chiba-ken; Naoki Harada, Saitama-ken, both of (JP)

(73) Assignee: Chugai Seiyaku Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/718,388

(22) PCT Filed: Apr. 3, 1995

(86) PCT No.: PCT/JP95/00638

§ 371 Date: Nov. 15, 1996

§ 102(e) Date: Nov. 15, 1996

(87) PCT Pub. No.: WO95/27057

PCT Pub. Date: Dec. 10, 1995

(30) Foreign Application Priority Data

Apr. 1, 1994 (JP) .................................................. 6-129487
Aug. 24, 1994 (JP) .................................................. 6-222547
Mar. 30, 1995 (JP) .................................................. 7-109927

(51) Int. Cl.[7] .............................. C07H 21/04; C12Q 1/68; C12P 21/06; C12N 15/00

(52) U.S. Cl. ........................... 536/23.5; 435/6; 435/69.1; 435/252.3; 435/320.1; 435/325

(58) Field of Search ....................... 536/23.5; 435/320.1, 435/326, 69.1, 6, 325; 530/387.1

(56) References Cited

U.S. PATENT DOCUMENTS 5,302,527 * 4/1994 Birkett et al .

FOREIGN PATENT DOCUMENTS

WO8905351A2  6/1989 (WO) .

OTHER PUBLICATIONS

Lazar et al (Molecular & cellular Bio. vol. 8 Mar. 1988 pp 1247–1252).*
Burgess et al (J. CF cell Bio. vol. III Nov. 1990 pp 2129–2138).*
Salgaller et al (Cancer Immunol. Immunother. vol. 39. 1994 pp 105–116).*
Reeck et al (Cell vol. 50, Aug. 28, 1997 p. 667).*
Kobayashi et al, The Journal of Immunology, vol. 143, No. 8, pp. 2567–2574 (Oct. 15, 1989).
Kobayashi et al, The Journal of Immunology, vol. 146, No. 1, pp. 68–74 (Jan. 1, 1991).
Hamada et al, Immunology, 74:298–303 (1991).
Kobayashi et al, Digestive Diseases and Sciences, vol. 39, No. 3, pp. 526–533 (1994).
van de Winkel et al., *Immunology Today*, vol. 14, No. 5, pp.215–221 (May 1993).

* cited by examiner

*Primary Examiner*—Albert Navarro
(74) *Attorney, Agent, or Firm*—Birch, Stewart, Kolasch & Birch, LLP.

(57) ABSTRACT

A gene encoding an IgG Fc region-binding protein (FCγBP); a recombinant vector containing this gene; host cells transformed by this recombinant vector; a process for producing a recombinant protein which is obtained by incubating these host cells; and a protein having a recombinant IgG Fc region-binding activity which is obtained by the above-mentioned process.

10 Claims, 17 Drawing Sheets

FIG. 10

| exon | conserved sequence CRGgt(a/g)agtn | intron | conserved sequence y$_n$agN | exon |
|---|---|---|---|---| exonI --GGG | gtaagtc--- intronI ---ttttctcaaccag | G-- exonII exonII --GGA | gtaagta--- intronII ---

---------GGATCCATACCCCCTGGCCCAATCTGCCCGACTTCTTT

CCCCACCTCAGCCTTCATGGTCCCAGGTGGCCCTTGTCATGAGAGTGGGCCCTTCTGCCCAGGACAGTCTCCAGCAGAGGCG

GTGGATCAGCCTTCTATGATCCTTTCTCTTTTCCTACTGCAGCCATGGGTGCCCTATGGAGCTGGTGGATACTCTGGGCTGGA
                                          1

GCAACCCTCCTGTGGGgtaagtcagaccaagaccctctccatgtccttgttccaatctggggaactctgcgtgggtccacgcc ttccatgtgtgcctcctccacatgtcacccccaggctagctgagactgaggagagaggcccttaggctctgcaggggatgtggta gaattc----------------Xkb-----------tgcctggcccatcagcattggagtttgagggccctgtct

FIGURE 11A aaggtgtttagattttgaaaaacaaagccaggaaggcttgtagacgaaagctgcatgaatcagaagaaagagagaag ggtggtgggggaaagcccaagttaatacttcaacatgtttctggtgcagagcaaaagtggggaggattggataagtggacc 101
cacaactgtatttctcaaccagGATTGACCCAGGAGGCTTCAGTGACCTCAAGAACACTGGCAGAGAGGAATTCCTCACA 201
GCCTTCCTGCAGAACTATCAGCTGGCCTACAGCAAGGCCTACCCCGCCTCCTTATCTCCAGTCTGTCAGAGAGCCCCGCT TCAGTCTCCATCCTCAGCCAGGCAGACAACACCTCAAAGAAGGTCACAGTGAGGCCCGGGAGTCGGTCATGGTCAACATCAG 301
TGCCAAGGCTGAGATGATAGGCAGCAAGATCTTCCAGCATGCGGTGGTGATCCATTCTGACTATGCCATTCTCTGTGCAGGCAG

FIGURE 11B

```
401
TAAATGCCAAGCCTGACACAGCGGAGCTGACACTGCTGCGGCCCATCCAGGCCCTAGGCACCGAGTATTTTGTGCTCACACCC

501
CCCGGCACCTCAGCCCAGGAATGTCAAGGAGTTTGCCGTGGTGGCCGGTGCCGCAGGTGCCTCGGTCAGTGTCACGCTGAAGGG

601
GTCAGTGACATTCAATGGCAAGTTCTATCCAGCCAGGCGATGTCCTAAGAGTGACTCTACAGCCCTACAATGTGGCCCAGCTA

CAGAGCTCAGTGGATCTCTCGGGGTCAAAGGTCACAGAGTAGCCCGTGGCTGTCCTCTCTGGCCACAGCTGTGCGCAGAA

701
ACATACGACCTGCAACCATGTGGTTGAGCAGCTGCTACCCACGTCTGCCTGGGGCACCCACTATGTAGTACCCACGCTGGCCT
```

FIGURE 11C

```
801
CCCAATCTCGCTATGATTTGGCCTTCGTTGTGGCCAGCCAGGCCACAAAGCTGACCTACAACCATGGGGTATCACTGGCTCC

901
CGTGGGCTCCAGGCAGGTGATGTGGTAGAGTTTGAGGTCCGGCCATCCTGGCCACTCTACCTGTCTGCAAATGTGGGCATCCA

1001
GGTCCTGTTGTTTGGCACAGGTGCCATAAGGAATGAAGTGACTTATGACCCCTACCTGTCCTGATCCCAGATGTGGCGGCCT

1101
ACTGCCCAGCCTATGTGGTCAAGAGTGTACCAGGCTGTGAGGGCGTGGCCCTGGTAGTGGCACAGACGAAGGCTATCAGGGGG

CTGACCATAGATGGGCATGCAGTGGGGGCCAAGCTCACCTGGGAGGCTGTGCCAGGCAGTGAGTTCTCGTATGCTGAAGTGG

1201
AGCTCGGCACAGCTGACATGATCCACAGGCCGAGGCCACCAACTTGGGACTGCTCACCTTCGGGCTGGCCAAGGCTATA
```

FIGURE 11D

```
1301
GGCTACGCAACAGCTGCTGATTGCGCCGGAgtaagtaatggaaatgtcccctggtcctgtccacctggtgaccgcttttcca cccacctactcctctgtggctttcgggatcctgattgtcctccctcacttctctttctccgcacatcctctcctcaagtcttc tcagcccctcccatccgcccagaaacaatattctaaatatttagcaaccagggagagctgggggcactaccagtcagaagagac agcagccaaagcactgtgacagggtcctgaagcccccatcatgctggcatcagcccctgtctgtgttggtttgttctggaaaggg ccc
```

FIGURE 11E

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
       (A) LENGTH: 908 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO: 1:

```
CTGCAGCCAT GGGTGCCCTA TGGAGCTGGT GGATACTCTG GCTGGAGCA ACCCTCCTGT      60
GGGGATTGAC CCAGGAGGCT TCAGTGGACC TCAAGAACAC TGGCAGAGAG GAATTCCTCA    120
CAGCCTTCCT GCAGAACTAT CAGCTGGCCT ACAGCAAGGC CTACCCCCGC CTCCTTATCT    180
CCAGTCTGTC AGAGAGCCCC GCTTCAGTCT CCATCCTCAG CCAGGCAGAC AACACCTCAA    240
AGAAGGTCAC AGTGAGGCCC GGGGAGTCGG TCATGGTCAA CATCAGTGCC AAGGCTGAGA    300
TGATAGGCAG CAAGATCTTC CAGCATGCGG TGGTGATCCA TTCTGACTAT GCCATCTCTG    360
TGCAGGCACT AAATGCCAAG CCTGACACAG CGGAGCTGAC ACTGCTGCGG CCCATCCAGG    420
CCCTAGGCAC CGAGTATTTT GTGCTCACAC CCCCGGCAC CTCAGCCAGG AATGTCAAGG    480
AGTTTGCCGT GGTGGCCGGT GCCGCAGGTG CCTCGGTCAG TGTCACGCTG AAGGGGTCAG    540
TGACATTCAA TGGCAAGTTC TATCCAGCAG GCGATGTCCT AAGAGTGACT CTACAGCCCT    600
ACAATGTGGC CCAGCTACAG AGCTCAGTGG ATCTCTCGGG GTCAAAGGTC ACAGCTAGTA    660
GCCCCGTGGC TGTCCTCTCT GGCCACAGCT GTGCGCAGAA ACATACGACC TGCAACCATG    720
TGGTTGAGCA GCTGCTACCC ACGTCTGCCT GGGGCACCCA CTATGTAGTA CCCACGCTGG    780
CCTCCCAATC TCGCTATGAT TTGGCCTTCG TTGTGGCCAG CCAGGCCACA AAGCTGACCT    840
ACAACCATGG GGGTATCACT GGCTCCCGTG GGCTCCAGGC AGGTGATGTG GTAGAGTTTG    900
AGGTCCGG                                                             908
```

(2) INFORMATION FOR SEQ ID NO: 2:

(i) SEQUENCE CHARACTERISTICS:
       (A) LENGTH: 1336 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO: 2:

```
GGCCTACAGC AAGGCCTACC CCGCCTCCT TATCTCCAGT CTGTCAGAGA GCCCCGCTTC      60
AGTCTCCATC CTCAGCCAGG CAGACAACAC CTCAAAGAAG GTCACAGTGA GGCCCGGGGA    120
GTCGGTCATG GTCAACATCA GTGCCAAGGC TGAGATGATA GGCAGCAAGA TCTTCCAGCA    180
TGCGGTGGTG ATCCATTCTG ACTATGCCAT CTCTGTGCAG GCACTAAATG CCAAGCCTGA    240
CACAGCGGAG CTGACACTGC TGCGGCCCAT CCAGGCCCTA GGCACCGAGT ATTTTGTGCT    300
CACACCCCCC GGCACCTCAG CCAGGAATGT CAAGGAGTTT GCCGTGGTGG CCGGTGCCGC    360
AGGTGCCTCG GTCAGTGTCA CGCTGAAGGG GTCAGTGACA TTCAATGGCA AGTTCTATCC    420
AGCAGGCGAT GTCCTAAGAG TGACTCTACA GCCCTACAAT GTGGCCCAGC TACAGAGCTC    480
```

```
AGTGGATCTC TCGGGGTCAA AGGTCACAGC TAGTAGCCCC GTGGCTGTCC TCTCTGGCCA    540

CAGCTGTGCG CAGAAACATA CGACCTGCAA CCATGTGGTT GAGCAGCTGC TACCCACGTC    600

TGCCTGGGGC ACCCACTATG TAGTACCCAC GCTGGCCTCC CAATCTCGCT ATGATTTGGC    660

CTTCGTTGTG GCCAGCCAGG CCACAAAGCT GACCTACAAC CATGGGGGTA TCACTGGCTC    720

CCGTGGGCTC CAGGCAGGTG ATGTGGTAGA GTTTGAGGTC CGGCCATCCT GGCCACTCTA    780

CCTGTCTGCA AATGTGGGCA TCCAGGTCCT GTTGTTTGGC ACAGGTGCCA TAAGGAATGA    840

AGTGACTTAT GACCCCTACC TGGTCCTGAT CCCAGATGTG GCGGCCTACT GCCCAGCCTA    900

TGTGGTCAAG AGTGTACCAG GCTGTGAGGG CGTGGCCCTG GTAGTGGCAC AGACGAAGGC    960

TATCAGCGGG CTGACCATAG ATGGGCATGC AGTGGGGGCC AAGCTCACCT GGGAGGCTGT   1020

GCCAGGCAGT GAGTTCTCGT ATGCTGAAGT GGAGCTCGGC ACAGCTGACA TGATCCACAC   1080

GGCCGAGGCC ACCACCAACT TGGGACTGCT CACCTTCGGG CTGGCCAAGG CTATAGGCTA   1140

CGCAACAGCT GCTGATTGCG GCCGGACTGT ACTGTCCCCA GTGGAGCCCT CCTGCGAAGG   1200

CATGCAGTGC GCAGCCGGGC AGCGCTGCCA GGTGGTAGGC GGGAAGGCCG GGTGTGTGGC   1260

GGAGTCCACC GCTGTCTGCC GCGCCCAGGG CGACCCCCAT TACACCACCT TCGACGGCCG   1320

TCGCTACGAC ATGATG                                                   1336

(2) INFORMATION FOR SEQ ID NO: 3:

(i) SEQUENCE CHARACTERISTICS:
        (A) LENGTH: 1878 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 3:

CCAAGCTCAC CTGGGAGGCT GTGCCAGGCA GTGAGTTCTC GTATGCTGAA GTGGAGCTCG     60

GCACAGCTGA CATGATCCAC ACGGCCGAGG CCACCACCAA CTTGGGACTG CTCACCTTCG    120

GGCTGGCCAA GGCTATAGGC TACGCAACAG CTGCTGATTG CGGCCGGACT GTACTGTCCC    180

CAGTGGAGCC CTCCTGCGAA GGCATGCAGT GCGCAGCCGG GCAGCGCTGC CAGGTGGTAG    240

GCGGGAAGGC CGGGTGTGTG GCGGAGTCCA CCGCTGTCTG CCGCGCCCAG GGCGACCCCC    300

ATTACACCAC CTTCGACGGC CGTCGCTACG ACATGATGGG CACCTGTTCG TACACGATGG    360

TGGAGCTGTG CAGCGAGGAC GACACCCTGC CCGCCTTCAG CGTGGAGGCC AAGAACGAGC    420

ACCGGGGCAG CCGCCGCGTC TCCTACGTGG GCCTCGTCAC TGTGCGCGCC TACAGCCACT    480

CTGTGTCGCT GACCCGCGGT GAAGTTGGCT TCGTCCTGGT TGACAACCAG CGCTCGCGCC    540

TGCCAGTCTC CCTGAGTGAG GGTCGCCTGC GTGTGTACCA GAGCGGACCA CGGGCCGTGG    600

TGGAGCTGGT CTTTGGGCTG GTGGTCACTT ATGACTGGGA CTGCCAGCTG GCACTCAGCC    660

TGCCTGCACG CTTCCAAGAC CAGGTGTGCG GGCTGTGTGG CAACTATAAT GGTGACCCAG    720

CAGACGACTT CCTCACGCCT GACGGGCTCT GGCTCCTGA CGCTGTGGAG TTCGCAAGTA    780

GCTGGAAGCT GGATGATGGG GACTACCTGT GTGAGGATGG CTGCCAGAAC AACTGTCCCG    840

CCTGCACCCC AGGCCAGGCC CAACACTATG AGGGCGACCG ACTCTGTGGC ATGCTGACCA    900

AGCTCGATGG CCCCTTCGCT GTCTGCCATG ACACCCTGGA CCCCAGGCCC TTCCTGGAGC    960

AGTGTGTATA TGACCTGTGT GTGGTCGGTG GGGAGCGGCT CAGCCTGTGC CGTGGCCTCA   1020

GCGCCTATGC CCAGGCCTGT CTGGAGCTTG GCATCTCGGT TGGGGACTGG AGATCACCAG   1080
```

-continued

```
CCAACTGCCC CCTGTCCTGC CCTGCCAACA GCCGCTATGA GCTCTGCGGC CCTGCTTGCC      1140

CGACCTCCTG CAACGGGGCT GCGGCGCCGT CCAACTGCTC CGGGCGCCCC TGCGTGGAGG      1200

GCTGCGTGTG CCTCCCAGGC TTCGTGGCCA GCGGCGGCGC CTGCGTGCCG GCCTCGTCGT      1260

GTGGCTGCAC CTTCCAGGGT CTCCAGCTCG CTCCGGGCCA GGAAGTGTGG GCGGACGAGT      1320

TGTGCCAAAG GCGCTGCACC TGCAACGGCG CCACCCATCA GGTCACCTGC CGCGACAAGC      1380

AGAGCTGCCC GGCGGGTGAG CGCTGCAGCG TCCAGAACGG CCTCCTGGGC TGCTACCCCG      1440

ATCGCTTCGG GACCTGCCAG GGGTCCGGGG ACCCACACTA TGTGAGCTTC GACGGCCGGC      1500

GCTTCGACTT CATGGGCACC TGCACGTACC TGCTGGTCGG CTCATGCGGC CAGAACGCAG      1560

CGCTGCCTGC CTTCCGGGTG CTGGTGGAAA ACGAGCATCG GGGCAGCCAG ACTGTGAGCT      1620

ACACGCGCGC CGTGCGGGTG GAGGCCCGCG GGGTGAAGGT GGCCGTGCGC CGGGAGTACC      1680

CCGGGCAAGT GCTGGTGGAT GACGTCCTTC AGTATCTGCC CTTCCAAGCA GCAGATGGGC      1740

AGGTGCAGGT GTTCCGACAG GGCAGGGATG CCGTCGTGCG CACGGACTTT GGCCTGACTG      1800

TCACTTATGA CTGGAATGCA CGAGTGACTG CCAAGGTGCC CAGCAGCTAT GCTGAGGCCC      1860

TGTGTGGACT CTGTGGGA                                                  1878
```

(2) INFORMATION FOR SEQ ID NO: 4:

(i) SEQUENCE CHARACTERISTICS:
        (A) LENGTH: 3247 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 4:

```
CTTCGACGGC CGTCGCTACG ACATGATGGG CACCTGTTCG TACACGATGG TGGAGCTGTG       60

CAGCGAGGAC GACACCCTGC CCGCCTTCAG CGTGGAGGCC AAGAACGAGC ACCGGGGCAG      120

CCGCCGCGTC TCCTACGTGG GCCTCGTCAC TGTGCGCGCC TACAGCCACT CTGTGTCGCT      180

GACCCGCGGT GAAGTTGGCT TCGTCCTGGT TGACAACCAG CGCTCGCGCC TGCCAGTCTC      240

CCTGAGTGAG GGTCGCCTGC GTGTGTACCA GAGCGGACCA CGGGCCGTGG TGGAGCTGGT      300

CTTTGGGCTG GTGGTCACTT ATGACTGGGA CTGCCAGCTG GCACTCAGCC TGCCTGCACG      360

CTTCCAAGAC CAGGTGTGCG GGCTGTGTGG CAACTATAAT GGTGACCCAG CAGACGACTT      420

CCTCACGCCT GACGGGGCTC TGGCTCCTGA CGCTGTGGAG TTCGCAAGTA GCTGGAAGCT      480

GGATGATGGG GACTACCTGT GTGAGGATGG CTGCCAGAAC AACTGTCCCG CCTGCACCCC      540

AGGCCAGGCC CAACACTATG AGGGCGACCG ACTCTGTGGC ATGCTGACCA AGCTCGATGG      600

CCCCTTCGCT GTCTGCCATG ACACCCTGGA CCCCAGGCCC TTCCTGGAGC AGTGTGTATA      660

TGACCTGTGT GTGGTCGGTG GGGAGCGGCT CAGCCTGTGC CGTGGCCTCA GCGCCTATGC      720

CCAGGCCTGT CTGGAGCTTG GCATCTCGGT TGGGGACTGG AGATCACCAG CCAACTGCCC      780

CCTGTCCTGC CCTGCCAACA GCCGCTATGA GCTCTGCGGC CCTGCTTGCC CGACCTCCTG      840

CAACGGGGCT GCGGCGCCGT CCAACTGCTC CGGGCGCCCC TGCGTGGAGG GCTGCGTGTG      900

CCTCCCAGGC TTCGTGGCCA GCGGCGGCGC CTGCGTGCCG GCCTCGTCGT GTGGCTGCAC      960

CTTCCAGGGT CTCCAGCTCG CTCCGGGCCA GGAAGTGTGG GCGGACGAGT TGTGCCAAAG     1020

GCGCTGCACC TGCAACGGCG CCACCCATCA GGTCACCTGC CGCGACAAGC AGAGCTGCCC     1080

GGCGGGTGAG CGCTGCAGCG TCCAGAACGG CCTCCTGGGC TGCTACCCCG ATCGCTTCGG     1140
```

```
GACCTGCCAG GGGTCCGGGG ACCCACACTA TGTGAGCTTC GACGGCCGGC GCTTCGACTT    1200

CATGGGCACC TGCACGTACC TGCTGGTCGG CTCATGCGGC CAGAACGCAG CGCTGCCTGC    1260

CTTCCGGGTG CTGGTGGAAA ACGAGCATCG GGGCAGCCAG ACTGTGAGCT ACACGCGCGC    1320

CGTGCGGGTG GAGGCCCGCG GGGTGAAGGT GGCCGTGCGC CGGGAGTACC CCGGGCAAGT    1380

GCTGGTGGAT GACGTCCTTC AGTATCTGCC CTTCCAAGCA GCAGATGGGC AGGTGCAGGT    1440

GTTCCGACAG GGCAGGGATG CCGTCGTGCG CACGGACTTT GGCCTGACTG TCACTTATGA    1500

CTGGAATGCA CGAGTGACTG CCAAGGTGCC CAGCAGCTAT GCTGAGGCCC TGTGTGGACT    1560

CTGTGGGAAC TTCAACGGGG ACCCAGCTGA TGACCTGGCT CTGCGGGGTG GGGTCAAGC    1620

TGCCAATGCA CTGGCCTTTG GAACAGCTG GCAAGAAGAG ACGAGGCCCG GCTGTGGAGC    1680

AACTGAACCG GGTGACTGTC CCAAGCTGGA CTCCCTGGTG GCCCAGCAGC TGCAGAGCAA    1740

GAATGAGTGT GGAATCCTTG CCGACCCCAA GGGGCCCTTC CGGGAGTGCC ATAGCAAGCT    1800

GGACCCCCAG GGTGCCGTGC GCGACTGTGT CTATGACCGC TGCCTGCTGC CAGGCCAGTC    1860

TGGGCCACTG TGTGACGCAC TGGCCACCTA TGCTGCTGCA TGCCAGGCTG CTGGAGCCAC    1920

AGTGCACCCC TGGAGGAGTG AAGAACTTTG CCCACTGAGC TGCCCACCCC ACAGCCACTA    1980

TGAGGCGTGT TCCTACGGCT GCCCGCTGTC CTGTGGAGAC CTCCCAGTGC CGGGGGCTG    2040

TGGCTCAGAA TGCCATGAGG GCTGCGTGTG CGATGAGGGC TTTGCGCTCA GTGGTGAGTC    2100

CTGCCTGCCC CTGGCCTCCT GTGGCTGCGT ACACCAGGGC ACCTACCACC CACCAGGCCA    2160

GACCTTCTAC CCTGGCCCCG GATGTGATTC CCTTTGCCAC TGCCAGGAGG GCGGCCTGGT    2220

GTCCTGTGAG TCCTCCAGCT GCGGACCGCA CGAGGCCTGC CAGCCATCCG GTGGCAGCTT    2280

GGGCTGTGTG GCCGTGGGCT CTAGCACCTG CCAGGCGTCA GGAGACCCCC ACTACACCAC    2340

CTTCGATGGC CGCCGCTTCG ACTTCATGGG CACCTGCGTG TATGTGCTGG CTCAGACCTG    2400

CGGCACCCGG CCTGGCCTGC ATCGGTTTGC CGTCCTGCAG GAGAACGTGG CCTGGGGTAA    2460

TGGGCGAGTC AGTGTGACCA GGGTGATCAC GGTCCAGGTG GCAAACTTCA CCCTGCGGCT    2520

GGAGCAGAGA CAGTGGAAGG TCACGGTGAA CGGTGTGGAC ATGAAGCTGC CCGTGGTGCT    2580

GGCCAACGGC CAGATCCGTG CCTCCCAGCA TGGTTCAGAT GTTGTGATTG AGACCGACTT    2640

CGGCCTGCGT GTGGCCTACG ACCTTGTGTA CTATGTGCGG GTCACCGTCC CCGGAAACTA    2700

CTACCAGCAG ATGTGTGGCC TGTGTGGGAA CTACAACGGC GACCCCAAGG ATGACTTCCA    2760

GAAGCCCAAT GGCTCACAGG CAGGCAACGC CAATGAGTTC GGCAACTCCT GGGAGGAGGT    2820

GGTGCCCGAC TCTCCCTGCC TGCCGCCCAC CCCTTGCCCG CCGGGGAGCG AGGACTGTAT    2880

CCCCAGCCAC AAGTGTCCTC CCGAGCTGGA GAAGAAGTAT CAGAAGGAGG AGTTCTGTGG    2940

GCTCCTCTCC AGCCCCACAG GGCCACTGTC CTCCTGCCAC AAGCTGGTGG ATCCCCAGGG    3000

TCCCTTGAAA GATTGCATCT TTGATCTCTG CCTGGGTGGT GGGAACCTGA GCATTCTCTG    3060

CAGCAACATC CATGCCTACG TGAGTGCTTG CCAGGCGGCT GGAGGCCACG TGGAGCCCTG    3120

GAGGACTGAA ACTTTCTGTC CCATGGAGTG CCCTCCGAAC AGTCACTACG AGCTCTGTGC    3180

GGACACCTGC TCCCTGGGCT GCTCAGCTCT CAGTGCCCCT CCACAGTGCC AGGATGGGTG    3240

TGCTGAG                                                             3247
```

(2) INFORMATION FOR SEQ ID NO: 5:

(i) SEQUENCE CHARACTERISTICS:
        (A) LENGTH: 3661 base pairs
        (B) TYPE: nucleic acid (C) STRANDEDNESS: single
(D) TOPOLOGY: linear (ii) MOLECULE TYPE: cDNA (xi) SEQUENCE DESCRIPTION: SEQ ID NO: 5:

```
CTATGTGCGG GTCACCGTCC CCGGAAACTA CTACCAGCAG ATGTGTGGCC TGTGTGGGAA      60

CTACAACGGC GACCCCAAGG ATGACTTCCA GAAGCCCAAT GGCTCACAGG CAGGCAACGC     120

CAATGAGTTC GGCAACTCCT GGGAGGAGGT GGTGCCCGAC TCTCCCTGCC TGCCGCCCAC     180

CCCTTGCCCG CCGGGGAGCG AGGACTGTAT CCCCAGCCAC AAGTGTCCTC CCGAGCTGGA     240

GAAGAAGTAT CAGAAGGAGG AGTTCTGTGG GCTCCTCTCC AGCCCCACAG GCCACTGTC     300

CTCCTGCCAC AAGCTGGTGG ATCCCCAGGG TCCCTTGAAA GATTGCATCT TTGATCTCTG     360

CCTGGGTGGT GGGAACCTGA GCATTCTCTG CAGCAACATC CATGCCTACG TGAGTGCTTG     420

CCAGGCGGCT GGAGGCCACG TGGAGCCCTG GAGGACTGAA ACTTTCTGTC CATGGAGTG     480

CCCTCCGAAC AGTCACTACG AGCTCTGTGC GGACACCTGC TCCCTGGGCT GCTCAGCTCT     540

CAGTGCCCCT CCACAGTGCC AGGATGGGTG TGCTGAGGGC TGCCAGTGTG ACTCCGGCTT     600

CCTCTACAAT GGCCAAGCCT GCGTGCCCAT CCAGCAATGC GGCTGCTACC ACAATGGTGT     660

CTACTATGAG CCGGAGCAGA CAGTCCTCAT TGACAACTGT CGGCAGCAGT GCACGTGCCA     720

TGCGGGTAAA GGCATGGTGT GCCAGGAACA CAGCTGCAAG CCGGGGCAGG TGTGCCAGCC     780

CTCCGGAGGC ATCCTGAGCT GCGTCACCAA AGACCCGTGC CACGGCGTGA CATGCCGGCC     840

ACAGGAGACA TGCAAGGAGC AGGGTGGCCA GGGCGTGTGC CTGCCCAACT ATGAGGCCAC     900

GTGCTGGCTG TGGGGCGACC CACACTACCA CTCCTTCGAT GGCCGGAAGT TTGACTTCCA     960

GGGCACCTGT AACTATGTGC TGGCAACAAC TGGCTGCCCG GGGGTCAGCA CCCAGGGCCT    1020

GACACCCTTC ACCGTCACCA CCAAGAACCA GAACCGGGGC AACCCTGCTG TGTCCTACGT    1080

GAGAGTCGTC ACCGTGGCTG CCCTCGGCAC CAACATCTCC ATCCACAAGG ACGAGATCGG    1140

CAAAGTCCGG GTGAACGGTG TGCTCACAGC CTTGCCTGTC TCTGTGGCCG ACGGGCGGAT    1200

TTCAGTGACC CAGGGTGCAT CGAAGGCACT GCTGGTGGCT GACTTTGGAC TGCAAGTCAG    1260

CTATGACTGG AACTGGCGGG TAGACGTGAC GCTGCCCAGC AGCTATCATG GCGCAGTGTG    1320

CGGGCTCTGC GGTAACATGG ACCGCAACCC CAACAATGAC CAGGTCTTCC CTAATGGCAC    1380

ACTGGCTCCC TCCATACCCA TCTGGGGCGG CAGCTGGCGA GCCCCAGGCT GGGACCCACT    1440

GTGTTGGGAC GAATGTCGGG GGTCCTGCCC AACGTGCCCT GAGGACCGGT TGGAGCAGTA    1500

CGAGGGCCCT GGCTTCTGCG GACCCCTGGC CCCCGGCACA GGGGGCCCTT TCACCACCTG    1560

CCATGCTCAT GTGCCACCTG AGAGCTTCTT CAAGGGCTGT GTTCTGGACG TCTGCATGGG    1620

TGGTGGGGAC CGTGACATTC TTTGCAAGGC TCTGGCTTCC TATGTGGCCG CCTGCCAGGC    1680

TGCTGGGGTT GTCATCGAAG ACTGGCGGGC ACAGGTTGGC TGTGAGATCA CCTGCCCAGA    1740

AAACAGCCAC TATGAGGTCT GTGGCCCACC CTGCCCGGCC AGCTGTCCGT CCCCTGCACC    1800

CCTTACGACG CCAGCCGTAT GTGAGGGCCC TGTGTGGAG GCTGCCAGT GCGACGCGGG    1860

TTTCGTGTTA AGTGCTGACC GCTGTGTTCC CCTCAACAAC GGCTGCGGCT GCTGGGCCAA    1920

TGGCACCTAC CACGAGGCGG GCAGTGAGTT TTGGGCTGAT GGCACCTGCT CCCAGTGGTG    1980

TCGCTGCGGG CCTGGGGGTG GCTCGCTGGT CTGCACACCT GCCAGCTGTG GCTGGGTGA    2040

AGTGTGTGGC CTCCTGCCAT CCGGCCAGCA CGGCTGCCAG CCCGTCAGCA CAGCTGAGTG    2100

CCAGGCGTGG GGTGACCCCC ATTACGTCAC TCTGGATGGG CACCGATTCA ATTTCCAAGG    2160
```

-continued

```
CACCTGCGAG TACCTGCTGA GTGCACCCTG CCACGGACCA CCCTTGGGGG CTGAGAACTT        2220

CACTGTCACT GTAGCCAATG AGCACCGGGG CAGCCAGGCT GTCAGCTACA CCCGCAGTGT        2280

CACCCTGCAA ATCTACAACC ACAGCCTGAC ACTGAGTGCC CGCTGGCCCC GGAAGCTACA        2340

GGTGGACGGC GTGTTCGTCA CTCTGCCCTT CCAGCTGGAC TCGCTCCTGC ACGCACACCT        2400

GAGCGGCGCC GACGTGGTGG TGACCACAAC CTCAGGGCTC TCGCTGGCTT TCGACGGGGA        2460

CAGCTTCGTG CGCCTGCGCG TGCCGGCGGC GTACGCGGGC TCTCTCTGTG GCTTATGCGG        2520

GAACTACAAC CAGGACCCCG CAGACGACCT GAAGGCGGTG GGCGGGAAGC CCGCCGGATG        2580

GCAGGTGGGC GGCGCCCAGG GCTGCGGGGA ATGTGTGTCC AAGCCATGCC CGTCGCCGTG        2640

CACCCCAGAG CAGCAAGAGT CCTTCGGCGG CCCGGACGCC TGCGGCGTGA TCTCCGCCAC        2700

CGACGGCCCG CTGGCGCCCT GCCACGGCCT TGTGCCGCCC GCGCAGTACT CCAGGGCTG         2760

CTTGCTGGAC GCCTGCCAAG TTCAGGGCCA TCCTGGAGGC CTCTGTCCTG CAGTGGCCAC        2820

CTACGTGGCA GCCTGTCAGG CCGCTGGGGC CCAGCTCCGC GAGTGGAGGC GGCCGGACTT        2880

CTGTCCCTTC CAGTGCCCTG CCCACAGCCA CTACAGCTC TGCGGTGACT CCTGTCCTGG         2940

GAGCTGCCCG AGCCTGTCGG CACCCGAGGG CTGTGAGTCG GCCTGCCGTG AAGGCTGTGT        3000

CTGCGATGCT GGCTTCGTGC TCAGTGGTGA CACGTGTGTA CCTGTGGGCC AGTGTGGCTG        3060

CCTCCACGAT GACCGCTACT ACCCACTGGG CCAGACCTTC TACCCTGGCC CTGGGTGTGA        3120

TTCCCTTTGC CGCTGCCGGG AGGGCGGTGA GGTGTCCTGT GAGCCCTCCA GCTGCGGCCC        3180

GCATGAGACC TGCCGGCCAT CCGGTGGCAG CTTGGGCTGC GTGGCCGTGG GCTCTACCAC        3240

CTGCCAGGCG TCGGGAGATC CCCACTACAC CACCTTCGAT GGCCGCCGCT TCGACTTCAT        3300

GGGCACCTGC GTGTATGTGC TGGCTCAGAC CTGCGGCACC CGGCCTGGCC TACATCGGTT        3360

TGCCGTCCTG CAGGAGAACG TGGCCTGGGG TAATGGGCGA GTCAGTGTGA CCAGGGTGAT        3420

CACGGTCCAG GTGGCAAACT TCACCCTGCG GCTGGAGCAG AGACAGTGGA AGGTCACGGT        3480

GAACGGTGTG GACATGAAGC TGCCCGTGGT GCTGGCCAAC GGCCAGATCC GTGCCTCCCA        3540

GCATGGTTCA GATGTTGTGA TTGAGACCGA CTTCGGCCTG CGTGTGGCCT ACGACCTTGT        3600

GTACTATGTG CGGGTCACCG TCCCTGGAAA CTACTACCAG CTGATGTGTG GCCTGTGTGG        3660

G                                                                      3661
```

(2) INFORMATION FOR SEQ ID NO: 6:

(i) SEQUENCE CHARACTERISTICS:
        (A) LENGTH: 7824 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 21..7802

(xi) SEQUENCE DESCRIPTION: SEQ ID NO: 6:

```
GGCCGCGGAT CCCTGCAGCC ATG GGT GCC CTA TGG AGC TGG TGG ATA CTC             50
                      Met Gly Ala Leu Trp Ser Trp Trp Ile Leu
                       1               5                  10

TGG GCT GGA GCA ACC CTC CTG TGG GGA TTG ACC CAG GAG GCT TCA GTG            98
Trp Ala Gly Ala Thr Leu Leu Trp Gly Leu Thr Gln Glu Ala Ser Val
             15                  20                  25

GAC CTC AAG AAC ACT GGC AGA GAG GAA TTC CTC ACA GCC TTC CTG CAG           146
Asp Leu Lys Asn Thr Gly Arg Glu Glu Phe Leu Thr Ala Phe Leu Gln
```

```
            30                  35                  40
AAC TAT CAG CTG GCC TAC AGC AAG GCC TAC CCC CGC CTC CTT ATC TCC      194
Asn Tyr Gln Leu Ala Tyr Ser Lys Ala Tyr Pro Arg Leu Leu Ile Ser
                45                  50                  55

AGT CTG TCA GAG AGC CCC GCT TCA GTC TCC ATC CTC AGC CAG GCA GAC      242
Ser Leu Ser Glu Ser Pro Ala Ser Val Ser Ile Leu Ser Gln Ala Asp
        60                  65                  70

AAC ACC TCA AAG AAG GTC ACA GTG AGG CCC GGG GAG TCG GTC ATG GTC      290
Asn Thr Ser Lys Lys Val Thr Val Arg Pro Gly Glu Ser Val Met Val
75                  80                  85                  90

AAC ATC AGT GCC AAG GCT GAG ATG ATA GGC AGC AAG ATC TTC CAG CAT      338
Asn Ile Ser Ala Lys Ala Glu Met Ile Gly Ser Lys Ile Phe Gln His
                95                  100                 105

GCG GTG GTG ATC CAT TCT GAC TAT GCC ATC TCT GTG CAG GCA CTA AAT      386
Ala Val Val Ile His Ser Asp Tyr Ala Ile Ser Val Gln Ala Leu Asn
            110                 115                 120

GCC AAG CCT GAC ACA GCG GAG CTG ACA CTG CTG CGG CCC ATC CAG GCC      434
Ala Lys Pro Asp Thr Ala Glu Leu Thr Leu Leu Arg Pro Ile Gln Ala
        125                 130                 135

CTA GGC ACC GAG TAT TTT GTG CTC ACA CCC CCC GGC ACC TCA GCC AGG      482
Leu Gly Thr Glu Tyr Phe Val Leu Thr Pro Pro Gly Thr Ser Ala Arg
    140                 145                 150

AAT GTC AAG GAG TTT GCC GTG GTG GCC GGT GCC GCA GGT GCC TCG GTC      530
Asn Val Lys Glu Phe Ala Val Val Ala Gly Ala Ala Gly Ala Ser Val
155                 160                 165                 170

AGT GTC ACG CTG AAG GGG TCA GTG ACA TTC AAT GGC AAG TTC TAT CCA      578
Ser Val Thr Leu Lys Gly Ser Val Thr Phe Asn Gly Lys Phe Tyr Pro
                175                 180                 185

GCA GGC GAT GTC CTA AGA GTG ACT CTA CAG CCC TAC AAT GTG GCC CAG      626
Ala Gly Asp Val Leu Arg Val Thr Leu Gln Pro Tyr Asn Val Ala Gln
            190                 195                 200

CTA CAG AGC TCA GTG GAT CTC TCG GGG TCA AAG GTC ACA GCT AGT AGC      674
Leu Gln Ser Ser Val Asp Leu Ser Gly Ser Lys Val Thr Ala Ser Ser
        205                 210                 215

CCC GTG GCT GTC CTC TCT GGC CAC AGC TGT GCG CAG AAA CAT ACG ACC      722
Pro Val Ala Val Leu Ser Gly His Ser Cys Ala Gln Lys His Thr Thr
    220                 225                 230

TGC AAC CAT GTG GTT GAG CAG CTG CTA CCC ACG TCT GCC TGG GGC ACC      770
Cys Asn His Val Val Glu Gln Leu Leu Pro Thr Ser Ala Trp Gly Thr
235                 240                 245                 250

CAC TAT GTA GTA CCC ACG CTG GCC TCC CAA TCT CGC TAT GAT TTG GCC      818
His Tyr Val Val Pro Thr Leu Ala Ser Gln Ser Arg Tyr Asp Leu Ala
                255                 260                 265

TTC GTT GTG GCC AGC CAG GCC ACA AAG CTG ACC TAC AAC CAT GGG GGT      866
Phe Val Val Ala Ser Gln Ala Thr Lys Leu Thr Tyr Asn His Gly Gly
            270                 275                 280

ATC ACT GGC TCC CGT GGG CTC CAG GCA GGT GAT GTG GTA GAG TTT GAG      914
Ile Thr Gly Ser Arg Gly Leu Gln Ala Gly Asp Val Val Glu Phe Glu
        285                 290                 295

GTC CGG CCA TCC TGG CCA CTC TAC CTG TCT GCA AAT GTG GGC ATC CAG      962
Val Arg Pro Ser Trp Pro Leu Tyr Leu Ser Ala Asn Val Gly Ile Gln
    300                 305                 310

GTC CTG TTG TTT GGC ACA GGT GCC ATA AGG AAT GAA GTG ACT TAT GAC      1010
Val Leu Leu Phe Gly Thr Gly Ala Ile Arg Asn Glu Val Thr Tyr Asp
315                 320                 325                 330

CCC TAC CTG GTC CTG ATC CCA GAT GTG GCG GCC TAC TGC CCA GCC TAT      1058
Pro Tyr Leu Val Leu Ile Pro Asp Val Ala Ala Tyr Cys Pro Ala Tyr
                335                 340                 345

GTG GTC AAG AGT GTA CCA GGC TGT GAG GGC GTG GCC CTG GTA GTG GCA      1106
```

-continued

```
                Val Val Lys Ser Val Pro Gly Cys Glu Gly Val Ala Leu Val Val Ala
                            350                 355                 360

CAG ACG AAG GCT ATC AGC GGG CTG ACC ATA GAT GGG CAT GCA GTG GGG            1154
Gln Thr Lys Ala Ile Ser Gly Leu Thr Ile Asp Gly His Ala Val Gly
            365                 370                 375

GCC AAG CTC ACC TGG GAG GCT GTG CCA GGC AGT GAG TTC TCG TAT GCT            1202
Ala Lys Leu Thr Trp Glu Ala Val Pro Gly Ser Glu Phe Ser Tyr Ala
        380                 385                 390

GAA GTG GAG CTC GGC ACA GCT GAC ATG ATC CAC ACG GCC GAG GCC ACC            1250
Glu Val Glu Leu Gly Thr Ala Asp Met Ile His Thr Ala Glu Ala Thr
395                 400                 405                 410

ACC AAC TTG GGA CTG CTC ACC TTC GGG CTG GCC AAG GCT ATA GGC TAC            1298
Thr Asn Leu Gly Leu Leu Thr Phe Gly Leu Ala Lys Ala Ile Gly Tyr
            415                 420                 425

GCA ACA GCT GCT GAT TGC GGC CGG ACT GTA CTG TCC CCA GTG GAG CCC            1346
Ala Thr Ala Ala Asp Cys Gly Arg Thr Val Leu Ser Pro Val Glu Pro
            430                 435                 440

TCC TGC GAA GGC ATG CAG TGC GCA GCC GGG CAG CGC TGC CAG GTG GTA            1394
Ser Cys Glu Gly Met Gln Cys Ala Ala Gly Gln Arg Cys Gln Val Val
            445                 450                 455

GGC GGG AAG GCC GGG TGT GTG GCG GAG TCC ACC GCT GTC TGC CGC GCC            1442
Gly Gly Lys Ala Gly Cys Val Ala Glu Ser Thr Ala Val Cys Arg Ala
        460                 465                 470

CAG GGC GAC CCC CAT TAC ACC ACC TTC GAC GGC CGT CGC TAC GAC ATG            1490
Gln Gly Asp Pro His Tyr Thr Thr Phe Asp Gly Arg Arg Tyr Asp Met
475                 480                 485                 490

ATG GGC ACC TGT TCG TAC ACG ATG GTG GAG CTG TGC AGC GAG GAC GAC            1538
Met Gly Thr Cys Ser Tyr Thr Met Val Glu Leu Cys Ser Glu Asp Asp
            495                 500                 505

ACC CTG CCC GCC TTC AGC GTG GAG GCC AAG AAC GAG CAC CGG GGC AGC            1586
Thr Leu Pro Ala Phe Ser Val Glu Ala Lys Asn Glu His Arg Gly Ser
        510                 515                 520

CGC CGC GTC TCC TAC GTG GGC CTC GTC ACT GTG CGC GCC TAC AGC CAC            1634
Arg Arg Val Ser Tyr Val Gly Leu Val Thr Val Arg Ala Tyr Ser His
        525                 530                 535

TCT GTG TCG CTG ACC CGC GGT GAA GTT GGC TTC GTC CTG GTT GAC AAC            1682
Ser Val Ser Leu Thr Arg Gly Glu Val Gly Phe Val Leu Val Asp Asn
        540                 545                 550

CAG CGC TCG CGC CTG CCA GTC TCC CTG AGT GAG GGT CGC CTG CGT GTG            1730
Gln Arg Ser Arg Leu Pro Val Ser Leu Ser Glu Gly Arg Leu Arg Val
555                 560                 565                 570

TAC CAG AGC GGA CCA CGG GCC GTG GTG GAG CTG GTC TTT GGG CTG GTG            1778
Tyr Gln Ser Gly Pro Arg Ala Val Val Glu Leu Val Phe Gly Leu Val
            575                 580                 585

GTC ACT TAT GAC TGG GAC TGC CAG CTG GCA CTC AGC CTG CCT GCA CGC            1826
Val Thr Tyr Asp Trp Asp Cys Gln Leu Ala Leu Ser Leu Pro Ala Arg
            590                 595                 600

TTC CAA GAC CAG GTG TGC GGG CTG TGT GGC AAC TAT AAT GGT GAC CCA            1874
Phe Gln Asp Gln Val Cys Gly Leu Cys Gly Asn Tyr Asn Gly Asp Pro
            605                 610                 615

GCA GAC GAC TTC CTC ACG CCT GAC GGG GCT CTG GCT CCT GAC GCT GTG            1922
Ala Asp Asp Phe Leu Thr Pro Asp Gly Ala Leu Ala Pro Asp Ala Val
            620                 625                 630

GAG TTC GCA AGT AGC TGG AAG CTG GAT GAT GGG GAC TAC CTG TGT GAG            1970
Glu Phe Ala Ser Ser Trp Lys Leu Asp Asp Gly Asp Tyr Leu Cys Glu
635                 640                 645                 650

GAT GGC TGC CAG AAC AAC TGT CCC GCC TGC ACC CCA GGC CAG GCC CAA            2018
Asp Gly Cys Gln Asn Asn Cys Pro Ala Cys Thr Pro Gly Gln Ala Gln
            655                 660                 665
```

```
CAC TAT GAG GGC GAC CGA CTC TGT GGC ATG CTG ACC AAG CTC GAT GGC       2066
His Tyr Glu Gly Asp Arg Leu Cys Gly Met Leu Thr Lys Leu Asp Gly
            670                 675                 680

CCC TTC GCT GTC TGC CAT GAC ACC CTG GAC CCC AGG CCC TTC CTG GAG       2114
Pro Phe Ala Val Cys His Asp Thr Leu Asp Pro Arg Pro Phe Leu Glu
        685                 690                 695

CAG TGT GTA TAT GAC CTG TGT GTG GTC GGT GGG GAG CGG CTC AGC CTG       2162
Gln Cys Val Tyr Asp Leu Cys Val Val Gly Gly Glu Arg Leu Ser Leu
    700                 705                 710

TGC CGT GGC CTC AGC GCC TAT GCC CAG GCC TGT CTG GAG CTT GGC ATC       2210
Cys Arg Gly Leu Ser Ala Tyr Ala Gln Ala Cys Leu Glu Leu Gly Ile
715                 720                 725                 730

TCG GTT GGG GAC TGG AGA TCA CCA GCC AAC TGC CCC CTG TCC TGC CCT       2258
Ser Val Gly Asp Trp Arg Ser Pro Ala Asn Cys Pro Leu Ser Cys Pro
                735                 740                 745

GCC AAC AGC CGC TAT GAG CTC TGC GGC CCT GCT TGC CCG ACC TCC TGC       2306
Ala Asn Ser Arg Tyr Glu Leu Cys Gly Pro Ala Cys Pro Thr Ser Cys
            750                 755                 760

AAC GGG GCT GCG GCG CCG TCC AAC TGC TCC GGG CGC CCC TGC GTG GAG       2354
Asn Gly Ala Ala Ala Pro Ser Asn Cys Ser Gly Arg Pro Cys Val Glu
        765                 770                 775

GGC TGC GTG TGC CTC CCA GGC TTC GTG GCC AGC GGC GGC GCC TGC GTG       2402
Gly Cys Val Cys Leu Pro Gly Phe Val Ala Ser Gly Gly Ala Cys Val
    780                 785                 790

CCG GCC TCG TCG TGT GGC TGC ACC TTC CAG GGT CTC CAG CTC GCT CCG       2450
Pro Ala Ser Ser Cys Gly Cys Thr Phe Gln Gly Leu Gln Leu Ala Pro
795                 800                 805                 810

GGC CAG GAA GTG TGG GCG GAC GAG TTG TGC CAA AGG CGC TGC ACC TGC       2498
Gly Gln Glu Val Trp Ala Asp Glu Leu Cys Gln Arg Arg Cys Thr Cys
                815                 820                 825

AAC GGC GCC ACC CAT CAG GTC ACC TGC CGC GAC AAG CAG AGC TGC CCG       2546
Asn Gly Ala Thr His Gln Val Thr Cys Arg Asp Lys Gln Ser Cys Pro
            830                 835                 840

GCG GGT GAG CGC TGC AGC GTC CAG AAC GGC CTC CTG GGC TGC TAC CCC       2594
Ala Gly Glu Arg Cys Ser Val Gln Asn Gly Leu Leu Gly Cys Tyr Pro
        845                 850                 855

GAT CGC TTC GGG ACC TGC CAG GGG TCC GGG GAC CCA CAC TAT GTG AGC       2642
Asp Arg Phe Gly Thr Cys Gln Gly Ser Gly Asp Pro His Tyr Val Ser
    860                 865                 870

TTC GAC GGC CGG CGC TTC GAC TTC ATG GGC ACC TGC ACG TAC CTG CTG       2690
Phe Asp Gly Arg Arg Phe Asp Phe Met Gly Thr Cys Thr Tyr Leu Leu
875                 880                 885                 890

GTC GGC TCA TGC GGC CAG AAC GCA GCG CTG CCT GCC TTC CGG GTG CTG       2738
Val Gly Ser Cys Gly Gln Asn Ala Ala Leu Pro Ala Phe Arg Val Leu
                895                 900                 905

GTG GAA AAC GAG CAT CGG GGC AGC CAG ACT GTG AGC TAC ACG CGC GCC       2786
Val Glu Asn Glu His Arg Gly Ser Gln Thr Val Ser Tyr Thr Arg Ala
            910                 915                 920

GTG CGG GTG GAG GCC CGC GGG GTG AAG GTG GCC GTG CGC CGG GAG TAC       2834
Val Arg Val Glu Ala Arg Gly Val Lys Val Ala Val Arg Arg Glu Tyr
        925                 930                 935

CCC GGG CAA GTG CTG GTG GAT GAC GTC CTT CAG TAT CTG CCC TTC CAA       2882
Pro Gly Gln Val Leu Val Asp Asp Val Leu Gln Tyr Leu Pro Phe Gln
    940                 945                 950

GCA GCA GAT GGG CAG GTG CAG GTG TTC CGA CAG GGC AGG GAT GCC GTC       2930
Ala Ala Asp Gly Gln Val Gln Val Phe Arg Gln Gly Arg Asp Ala Val
955                 960                 965                 970

GTG CGC ACG GAC TTT GGC CTG ACT GTC ACT TAT GAC TGG AAT GCA CGA       2978
Val Arg Thr Asp Phe Gly Leu Thr Val Thr Tyr Asp Trp Asn Ala Arg
                975                 980                 985
```

-continued

```
GTG ACT GCC AAG GTG CCC AGC AGC TAT GCT GAG GCC CTG TGT GGA CTC    3026
Val Thr Ala Lys Val Pro Ser Ser Tyr Ala Glu Ala Leu Cys Gly Leu
        990             995                 1000

TGT GGG AAC TTC AAC GGG GAC CCA GCT GAT GAC CTG GCT CTG CGG GGT    3074
Cys Gly Asn Phe Asn Gly Asp Pro Ala Asp Asp Leu Ala Leu Arg Gly
            1005                1010                1015

GGG GGT CAA GCT GCC AAT GCA CTG GCC TTT GGG AAC AGC TGG CAA GAA    3122
Gly Gly Gln Ala Ala Asn Ala Leu Ala Phe Gly Asn Ser Trp Gln Glu
        1020                1025                1030

GAG ACG AGG CCC GGC TGT GGA GCA ACT GAA CCG GGT GAC TGT CCC AAG    3170
Glu Thr Arg Pro Gly Cys Gly Ala Thr Glu Pro Gly Asp Cys Pro Lys
1035                1040                1045                1050

CTG GAC TCC CTG GTG GCC CAG CAG CTG CAG AGC AAG AAT GAG TGT GGA    3218
Leu Asp Ser Leu Val Ala Gln Gln Leu Gln Ser Lys Asn Glu Cys Gly
                1055                1060                1065

ATC CTT GCC GAC CCC AAG GGG CCC TTC CGG GAG TGC CAT AGC AAG CTG    3266
Ile Leu Ala Asp Pro Lys Gly Pro Phe Arg Glu Cys His Ser Lys Leu
            1070                1075                1080

GAC CCC CAG GGT GCC GTG CGC GAC TGT GTC TAT GAC CGC TGC CTG CTG    3314
Asp Pro Gln Gly Ala Val Arg Asp Cys Val Tyr Asp Arg Cys Leu Leu
        1085                1090                1095

CCA GGC CAG TCT GGG CCA CTG TGT GAC GCA CTG GCC ACC TAT GCT GCT    3362
Pro Gly Gln Ser Gly Pro Leu Cys Asp Ala Leu Ala Thr Tyr Ala Ala
    1100                1105                1110

GCA TGC CAG GCT GCT GGA GCC ACA GTG CAC CCC TGG AGG AGT GAA GAA    3410
Ala Cys Gln Ala Ala Gly Ala Thr Val His Pro Trp Arg Ser Glu Glu
1115                1120                1125                1130

CTT TGC CCA CTG AGC TGC CCA CCC CAC AGC CAC TAT GAG GCG TGT TCC    3458
Leu Cys Pro Leu Ser Cys Pro Pro His Ser His Tyr Glu Ala Cys Ser
                1135                1140                1145

TAC GGC TGC CCG CTG TCC TGT GGA GAC CTC CCA GTG CCC GGG GGC TGT    3506
Tyr Gly Cys Pro Leu Ser Cys Gly Asp Leu Pro Val Pro Gly Gly Cys
            1150                1155                1160

GGC TCA GAA TGC CAT GAG GGC TGC GTG TGC GAT GAG GGC TTT GCG CTC    3554
Gly Ser Glu Cys His Glu Gly Cys Val Cys Asp Glu Gly Phe Ala Leu
        1165                1170                1175

AGT GGT GAG TCC TGC CTG CCC CTG GCC TCC TGT GGC TGC GTA CAC CAG    3602
Ser Gly Glu Ser Cys Leu Pro Leu Ala Ser Cys Gly Cys Val His Gln
    1180                1185                1190

GGC ACC TAC CAC CCA CCA GGC CAG ACC TTC TAC CCT GGC CCC GGA TGT    3650
Gly Thr Tyr His Pro Pro Gly Gln Thr Phe Tyr Pro Gly Pro Gly Cys
1195                1200                1205                1210

GAT TCC CTT TGC CAC TGC CAG GAG GGC GGC CTG GTG TCC TGT GAG TCC    3698
Asp Ser Leu Cys His Cys Gln Glu Gly Gly Leu Val Ser Cys Glu Ser
                1215                1220                1225

TCC AGC TGC GGA CCG CAC GAG GCC TGC CAG CCA TCC GGT GGC AGC TTG    3746
Ser Ser Cys Gly Pro His Glu Ala Cys Gln Pro Ser Gly Gly Ser Leu
            1230                1235                1240

GGC TGT GTG GCC GTG GGC TCT AGC ACC TGC CAG GCG TCA GGA GAC CCC    3794
Gly Cys Val Ala Val Gly Ser Ser Thr Cys Gln Ala Ser Gly Asp Pro
        1245                1250                1255

CAC TAC ACC ACC TTC GAT GGC CGC CGC TTC GAC TTC ATG GGC ACC TGC    3842
His Tyr Thr Thr Phe Asp Gly Arg Arg Phe Asp Phe Met Gly Thr Cys
    1260                1265                1270

GTG TAT GTG CTG GCT CAG ACC TGC GGC ACC CGG CCT GGC CTG CAT CGG    3890
Val Tyr Val Leu Ala Gln Thr Cys Gly Thr Arg Pro Gly Leu His Arg
1275                1280                1285                1290

TTT GCC GTC CTG CAG GAG AAC GTG GCC TGG GGT AAT GGG CGA GTC AGT    3938
Phe Ala Val Leu Gln Glu Asn Val Ala Trp Gly Asn Gly Arg Val Ser
```

```
                1295                1300                1305
GTG ACC AGG GTG ATC ACG GTC CAG GTG GCA AAC TTC ACC CTG CGG CTG        3986
Val Thr Arg Val Ile Thr Val Gln Val Ala Asn Phe Thr Leu Arg Leu
            1310                1315                1320

GAG CAG AGA CAG TGG AAG GTC ACG GTG AAC GGT GTG GAC ATG AAG CTG        4034
Glu Gln Arg Gln Trp Lys Val Thr Val Asn Gly Val Asp Met Lys Leu
            1325                1330                1335

CCC GTG GTG CTG GCC AAC GGC CAG ATC CGT GCC TCC CAG CAT GGT TCA        4082
Pro Val Val Leu Ala Asn Gly Gln Ile Arg Ala Ser Gln His Gly Ser
        1340                1345                1350

GAT GTT GTG ATT GAG ACC GAC TTC GGC CTG CGT GTG GCC TAC GAC CTT        4130
Asp Val Val Ile Glu Thr Asp Phe Gly Leu Arg Val Ala Tyr Asp Leu
1355                1360                1365                1370

GTG TAC TAT GTG CGG GTC ACC GTC CCC GGA AAC TAC TAC CAG CAG ATG        4178
Val Tyr Tyr Val Arg Val Thr Val Pro Gly Asn Tyr Tyr Gln Gln Met
            1375                1380                1385

TGT GGC CTG TGT GGG AAC TAC AAC GGC GAC CCC AAG GAT GAC TTC CAG        4226
Cys Gly Leu Cys Gly Asn Tyr Asn Gly Asp Pro Lys Asp Asp Phe Gln
            1390                1395                1400

AAG CCC AAT GGC TCA CAG GCA GGC AAC GCC AAT GAG TTC GGC AAC TCC        4274
Lys Pro Asn Gly Ser Gln Ala Gly Asn Ala Asn Glu Phe Gly Asn Ser
        1405                1410                1415

TGG GAG GAG GTG GTG CCC GAC TCT CCC TGC CTG CCG CCC ACC CCT TGC        4322
Trp Glu Glu Val Val Pro Asp Ser Pro Cys Leu Pro Pro Thr Pro Cys
        1420                1425                1430

CCG CCG GGG AGC GAG GAC TGT ATC CCC AGC CAC AAG TGT CCT CCC GAG        4370
Pro Pro Gly Ser Glu Asp Cys Ile Pro Ser His Lys Cys Pro Pro Glu
1435                1440                1445                1450

CTG GAG AAG AAG TAT CAG AAG GAG GAG TTC TGT GGG CTC CTC TCC AGC        4418
Leu Glu Lys Lys Tyr Gln Lys Glu Glu Phe Cys Gly Leu Leu Ser Ser
            1455                1460                1465

CCC ACA GGG CCA CTG TCC TCC TGC CAC AAG CTG GTG GAT CCC CAG GGT        4466
Pro Thr Gly Pro Leu Ser Ser Cys His Lys Leu Val Asp Pro Gln Gly
            1470                1475                1480

CCC TTG AAA GAT TGC ATC TTT GAT CTC TGC CTG GGT GGT GGG AAC CTG        4514
Pro Leu Lys Asp Cys Ile Phe Asp Leu Cys Leu Gly Gly Gly Asn Leu
        1485                1490                1495

AGC ATT CTC TGC AGC AAC ATC CAT GCC TAC GTG AGT GCT TGC CAG GCG        4562
Ser Ile Leu Cys Ser Asn Ile His Ala Tyr Val Ser Ala Cys Gln Ala
        1500                1505                1510

GCT GGA GGC CAC GTG GAG CCC TGG AGG ACT GAA ACT TTC TGT CCC ATG        4610
Ala Gly Gly His Val Glu Pro Trp Arg Thr Glu Thr Phe Cys Pro Met
1515                1520                1525                1530

GAG TGC CCT CCG AAC AGT CAC TAC GAG CTC TGT GCG GAC ACC TGC TCC        4658
Glu Cys Pro Pro Asn Ser His Tyr Glu Leu Cys Ala Asp Thr Cys Ser
            1535                1540                1545

CTG GGC TGC TCA GCT CTC AGT GCC CCT CCA CAG TGC CAG GAT GGG TGT        4706
Leu Gly Cys Ser Ala Leu Ser Ala Pro Pro Gln Cys Gln Asp Gly Cys
        1550                1555                1560

GCT GAG GGC TGC CAG TGT GAC TCC GGC TTC CTC TAC AAT GGC CAA GCC        4754
Ala Glu Gly Cys Gln Cys Asp Ser Gly Phe Leu Tyr Asn Gly Gln Ala
        1565                1570                1575

TGC GTG CCC ATC CAG CAA TGC GGC TGC TAC CAC AAT GGT GTC TAC TAT        4802
Cys Val Pro Ile Gln Gln Cys Gly Cys Tyr His Asn Gly Val Tyr Tyr
        1580                1585                1590

GAG CCG GAG CAG ACA GTC CTC ATT GAC AAC TGT CGG CAG CAG TGC ACG        4850
Glu Pro Glu Gln Thr Val Leu Ile Asp Asn Cys Arg Gln Gln Cys Thr
1595                1600                1605                1610

TGC CAT GCG GGT AAA GGC ATG GTG TGC CAG GAA CAC AGC TGC AAG CCG        4898
```

```
                Cys His Ala Gly Lys Gly Met Val Cys Gln Glu His Ser Cys Lys Pro
                                1615                1620                1625

GGG CAG GTG TGC CAG CCC TCC GGA GGC ATC CTG AGC TGC GTC ACC AAA           4946
Gly Gln Val Cys Gln Pro Ser Gly Gly Ile Leu Ser Cys Val Thr Lys
            1630                1635                1640

GAC CCG TGC CAC GGC GTG ACA TGC CGG CCA CAG GAG ACA TGC AAG GAG           4994
Asp Pro Cys His Gly Val Thr Cys Arg Pro Gln Glu Thr Cys Lys Glu
            1645                1650                1655

CAG GGT GGC CAG GGC GTG TGC CTG CCC AAC TAT GAG GCC ACG TGC TGG           5042
Gln Gly Gly Gln Gly Val Cys Leu Pro Asn Tyr Glu Ala Thr Cys Trp
            1660                1665                1670

CTG TGG GGC GAC CCA CAC TAC CAC TCC TTC GAT GGC CGG AAG TTT GAC           5090
Leu Trp Gly Asp Pro His Tyr His Ser Phe Asp Gly Arg Lys Phe Asp
1675                1680                1685                1690

TTC CAG GGC ACC TGT AAC TAT GTG CTG GCA ACA ACT GGC TGC CCG GGG           5138
Phe Gln Gly Thr Cys Asn Tyr Val Leu Ala Thr Thr Gly Cys Pro Gly
                1695                1700                1705

GTC AGC ACC CAG GGC CTG ACA CCC TTC ACC GTC ACC ACC AAG AAC CAG           5186
Val Ser Thr Gln Gly Leu Thr Pro Phe Thr Val Thr Thr Lys Asn Gln
            1710                1715                1720

AAC CGG GGC AAC CCT GCT GTG TCC TAC GTG AGA GTC GTC ACC GTG GCT           5234
Asn Arg Gly Asn Pro Ala Val Ser Tyr Val Arg Val Val Thr Val Ala
            1725                1730                1735

GCC CTC GGC ACC AAC ATC TCC ATC CAC AAG GAC GAG ATC GGC AAA GTC           5282
Ala Leu Gly Thr Asn Ile Ser Ile His Lys Asp Glu Ile Gly Lys Val
            1740                1745                1750

CGG GTG AAC GGT GTG CTC ACA GCC TTG CCT GTC TCT GTG GCC GAC GGG           5330
Arg Val Asn Gly Val Leu Thr Ala Leu Pro Val Ser Val Ala Asp Gly
1755                1760                1765                1770

CGG ATT TCA GTG ACC CAG GGT GCA TCG AAG GCA CTG CTG GTG GCT GAC           5378
Arg Ile Ser Val Thr Gln Gly Ala Ser Lys Ala Leu Leu Val Ala Asp
                1775                1780                1785

TTT GGA CTG CAA GTC AGC TAT GAC TGG AAC TGG CGG GTA GAC GTG ACG           5426
Phe Gly Leu Gln Val Ser Tyr Asp Trp Asn Trp Arg Val Asp Val Thr
            1790                1795                1800

CTG CCC AGC AGC TAT CAT GGC GCA GTG TGC GGG CTC TGC GGT AAC ATG           5474
Leu Pro Ser Ser Tyr His Gly Ala Val Cys Gly Leu Cys Gly Asn Met
            1805                1810                1815

GAC CGC AAC CCC AAC AAT GAC CAG GTC TTC CCT AAT GGC ACA CTG GCT           5522
Asp Arg Asn Pro Asn Asn Asp Gln Val Phe Pro Asn Gly Thr Leu Ala
            1820                1825                1830

CCC TCC ATA CCC ATC TGG GGC GGC AGC TGG CGA GCC CCA GGC TGG GAC           5570
Pro Ser Ile Pro Ile Trp Gly Gly Ser Trp Arg Ala Pro Gly Trp Asp
1835                1840                1845                1850

CCA CTG TGT TGG GAC GAA TGT CGG GGG TCC TGC CCA ACG TGC CCT GAG           5618
Pro Leu Cys Trp Asp Glu Cys Arg Gly Ser Cys Pro Thr Cys Pro Glu
                1855                1860                1865

GAC CGG TTG GAG CAG TAC GAG GGC CCT GGC TTC TGC GGA CCC CTG GCC           5666
Asp Arg Leu Glu Gln Tyr Glu Gly Pro Gly Phe Cys Gly Pro Leu Ala
            1870                1875                1880

CCC GGC ACA GGG GGC CCT TTC ACC ACC TGC CAT GCT CAT GTG CCA CCT           5714
Pro Gly Thr Gly Gly Pro Phe Thr Thr Cys His Ala His Val Pro Pro
            1885                1890                1895

GAG AGC TTC TTC AAG GGC TGT GTT CTG GAC GTC TGC ATG GGT GGT GGG           5762
Glu Ser Phe Phe Lys Gly Cys Val Leu Asp Val Cys Met Gly Gly Gly
            1900                1905                1910

GAC CGT GAC ATT CTT TGC AAG GCT CTG GCT TCC TAT GTG GCC GCC TGC           5810
Asp Arg Asp Ile Leu Cys Lys Ala Leu Ala Ser Tyr Val Ala Ala Cys
1915                1920                1925                1930
```

-continued

| | |
|---|---|
| CAG GCT GCT GGG GTT GTC ATC GAA GAC TGG CGG GCA CAG GTT GGC TGT<br>Gln Ala Ala Gly Val Val Ile Glu Asp Trp Arg Ala Gln Val Gly Cys<br>　　　　　　　　　1935　　　　　　　　　1940　　　　　　　　　1945 | 5858 |
| GAG ATC ACC TGC CCA GAA AAC AGC CAC TAT GAG GTC TGT GGC CCA CCC<br>Glu Ile Thr Cys Pro Glu Asn Ser His Tyr Glu Val Cys Gly Pro Pro<br>　　　　　1950　　　　　　　　　1955　　　　　　　　　1960 | 5906 |
| TGC CCG GCC AGC TGT CCG TCC CCT GCA CCC CTT ACG ACG CCA GCC GTA<br>Cys Pro Ala Ser Cys Pro Ser Pro Ala Pro Leu Thr Thr Pro Ala Val<br>　　　　　　　1965　　　　　　　　　1970　　　　　　　　　1975 | 5954 |
| TGT GAG GGC CCC TGT GTG GAG GGC TGC CAG TGC GAC GCG GGT TTC GTG<br>Cys Glu Gly Pro Cys Val Glu Gly Cys Gln Cys Asp Ala Gly Phe Val<br>　　1980　　　　　　　　　1985　　　　　　　　　1990 | 6002 |
| TTA AGT GCT GAC CGC TGT GTT CCC CTC AAC AAC GGC TGC GGC TGC TGG<br>Leu Ser Ala Asp Arg Cys Val Pro Leu Asn Asn Gly Cys Gly Cys Trp<br>1995　　　　　　　　　2000　　　　　　　　　2005　　　　　　　　　2010 | 6050 |
| GCC AAT GGC ACC TAC CAC GAG GCG GGC AGT GAG TTT TGG GCT GAT GGC<br>Ala Asn Gly Thr Tyr His Glu Ala Gly Ser Glu Phe Trp Ala Asp Gly<br>　　　　　　　　　2015　　　　　　　　　2020　　　　　　　　　2025 | 6098 |
| ACC TGC TCC CAG TGG TGT CGC TGC GGG CCT GGG GGT GGC TCG CTG GTC<br>Thr Cys Ser Gln Trp Cys Arg Cys Gly Pro Gly Gly Gly Ser Leu Val<br>　　　　　　2030　　　　　　　　　2035　　　　　　　　　2040 | 6146 |
| TGC ACA CCT GCC AGC TGT GGG CTG GGT GAA GTG TGT GGC CTC CTG CCA<br>Cys Thr Pro Ala Ser Cys Gly Leu Gly Glu Val Cys Gly Leu Leu Pro<br>　　　　　　　2045　　　　　　　　　2050　　　　　　　　　2055 | 6194 |
| TCC GGC CAG CAC GGC TGC CAG CCC GTC AGC ACA GCT GAG TGC CAG GCG<br>Ser Gly Gln His Gly Cys Gln Pro Val Ser Thr Ala Glu Cys Gln Ala<br>　　2060　　　　　　　　　2065　　　　　　　　　2070 | 6242 |
| TGG GGT GAC CCC CAT TAC GTC ACT CTG GAT GGG CAC CGA TTC AAT TTC<br>Trp Gly Asp Pro His Tyr Val Thr Leu Asp Gly His Arg Phe Asn Phe<br>2075　　　　　　　　　2080　　　　　　　　　2085　　　　　　　　　2090 | 6290 |
| CAA GGC ACC TGC GAG TAC CTG CTG AGT GCA CCC TGC CAC GGA CCA CCC<br>Gln Gly Thr Cys Glu Tyr Leu Leu Ser Ala Pro Cys His Gly Pro Pro<br>　　　　　　　　　2095　　　　　　　　　2100　　　　　　　　　2105 | 6338 |
| TTG GGG GCT GAG AAC TTC ACT GTC ACT GTA GCC AAT GAG CAC CGG GGC<br>Leu Gly Ala Glu Asn Phe Thr Val Thr Val Ala Asn Glu His Arg Gly<br>　　　　　　　　　2110　　　　　　　　　2115　　　　　　　　　2120 | 6386 |
| AGC CAG GCT GTC AGC TAC ACC CGC AGT GTC ACC CTG CAA ATC TAC AAC<br>Ser Gln Ala Val Ser Tyr Thr Arg Ser Val Thr Leu Gln Ile Tyr Asn<br>　　　　　　2125　　　　　　　　　2130　　　　　　　　　2135 | 6434 |
| CAC AGC CTG ACA CTG AGT GCC CGC TGG CCC CGG AAG CTA CAG GTG GAC<br>His Ser Leu Thr Leu Ser Ala Arg Trp Pro Arg Lys Leu Gln Val Asp<br>　　　2140　　　　　　　　　2145　　　　　　　　　2150 | 6482 |
| GGC GTG TTC GTC ACT CTG CCC TTC CAG CTG GAC TCG CTC CTG CAC GCA<br>Gly Val Phe Val Thr Leu Pro Phe Gln Leu Asp Ser Leu Leu His Ala<br>2155　　　　　　　　　2160　　　　　　　　　2165　　　　　　　　　2170 | 6530 |
| CAC CTG AGC GGC GCC GAC GTG GTG GTG ACC ACA ACC TCA GGG CTC TCG<br>His Leu Ser Gly Ala Asp Val Val Val Thr Thr Thr Ser Gly Leu Ser<br>　　　　　　　　　2175　　　　　　　　　2180　　　　　　　　　2185 | 6578 |
| CTG GCT TTC GAC GGG GAC AGC TTC GTG CGC CTG CGC GTG CCG GCG GCG<br>Leu Ala Phe Asp Gly Asp Ser Phe Val Arg Leu Arg Val Pro Ala Ala<br>　　　　　　　2190　　　　　　　　　2195　　　　　　　　　2200 | 6626 |
| TAC GCG GGC TCT CTC TGT GGC TTA TGC GGG AAC TAC AAC CAG GAC CCC<br>Tyr Ala Gly Ser Leu Cys Gly Leu Cys Gly Asn Tyr Asn Gln Asp Pro<br>　　　　　　　　　2205　　　　　　　　　2210　　　　　　　　　2215 | 6674 |
| GCA GAC GAC CTG AAG GCG GTG GGC GGG AAG CCC GCC GGA TGG CAG GTG<br>Ala Asp Asp Leu Lys Ala Val Gly Gly Lys Pro Ala Gly Trp Gln Val<br>　　2220　　　　　　　　　2225　　　　　　　　　2230 | 6722 |
| GGC GGC GCC CAG GGC TGC GGG GAA TGT GTG TCC AAG CCA TGC CCG TCG<br>Gly Gly Ala Gln Gly Cys Gly Glu Cys Val Ser Lys Pro Cys Pro Ser<br>2235　　　　　　　　　2240　　　　　　　　　2245　　　　　　　　　2250 | 6770 |

```
CCG TGC ACC CCA GAG CAG CAA GAG TCC TTC GGC GGC CCG GAC GCC TGC      6818
Pro Cys Thr Pro Glu Gln Gln Glu Ser Phe Gly Gly Pro Asp Ala Cys
            2255                2260                2265

GGC GTG ATC TCC GCC ACC GAC GGC CCG CTG GCG CCC TGC CAC GGC CTT      6866
Gly Val Ile Ser Ala Thr Asp Gly Pro Leu Ala Pro Cys His Gly Leu
            2270                2275                2280

GTG CCG CCC GCG CAG TAC TTC CAG GGC TGC TTG CTG GAC GCC TGC CAA      6914
Val Pro Pro Ala Gln Tyr Phe Gln Gly Cys Leu Leu Asp Ala Cys Gln
            2285                2290                2295

GTT CAG GGC CAT CCT GGA GGC CTC TGT CCT GCA GTG GCC ACC TAC GTG      6962
Val Gln Gly His Pro Gly Gly Leu Cys Pro Ala Val Ala Thr Tyr Val
            2300                2305                2310

GCA GCC TGT CAG GCC GCT GGG GCC CAG CTC CGC GAG TGG AGG CGG CCG      7010
Ala Ala Cys Gln Ala Ala Gly Ala Gln Leu Arg Glu Trp Arg Arg Pro
2315                2320                2325                2330

GAC TTC TGT CCC TTC CAG TGC CCT GCC CAC AGC CAC TAC GAG CTC TGC      7058
Asp Phe Cys Pro Phe Gln Cys Pro Ala His Ser His Tyr Glu Leu Cys
            2335                2340                2345

GGT GAC TCC TGT CCT GGG AGC TGC CCG AGC CTG TCG GCA CCC GAG GGC      7106
Gly Asp Ser Cys Pro Gly Ser Cys Pro Ser Leu Ser Ala Pro Glu Gly
            2350                2355                2360

TGT GAG TCG GCC TGC CGT GAA GGC TGT GTC TGC GAT GCT GGC TTC GTG      7154
Cys Glu Ser Ala Cys Arg Glu Gly Cys Val Cys Asp Ala Gly Phe Val
            2365                2370                2375

CTC AGT GGT GAC ACG TGT GTA CCT GTG GGC CAG TGT GGC TGC CTC CAC      7202
Leu Ser Gly Asp Thr Cys Val Pro Val Gly Gln Cys Gly Cys Leu His
            2380                2385                2390

GAT GAC CGC TAC TAC CCA CTG GGC CAG ACC TTC TAC CCT GGC CCT GGG      7250
Asp Asp Arg Tyr Tyr Pro Leu Gly Gln Thr Phe Tyr Pro Gly Pro Gly
2395                2400                2405                2410

TGT GAT TCC CTT TGC CGC TGC CGG GAG GGC GGT GAG GTG TCC TGT GAG      7298
Cys Asp Ser Leu Cys Arg Cys Arg Glu Gly Gly Glu Val Ser Cys Glu
            2415                2420                2425

CCC TCC AGC TGC GGC CCG CAT GAG ACC TGC CGG CCA TCC GGT GGC AGC      7346
Pro Ser Ser Cys Gly Pro His Glu Thr Cys Arg Pro Ser Gly Gly Ser
            2430                2435                2440

TTG GGC TGC GTG GCC GTG GGC TCT ACC ACC TGC CAG GCG TCG GGA GAT      7394
Leu Gly Cys Val Ala Val Gly Ser Thr Thr Cys Gln Ala Ser Gly Asp
            2445                2450                2455

CCC CAC TAC ACC ACC TTC GAT GGC CGC CGC TTC GAC TTC ATG GGC ACC      7442
Pro His Tyr Thr Thr Phe Asp Gly Arg Arg Phe Asp Phe Met Gly Thr
            2460                2465                2470

TGC GTG TAT GTG CTG GCT CAG ACC TGC GGC ACC CGG CCT GGC CTA CAT      7490
Cys Val Tyr Val Leu Ala Gln Thr Cys Gly Thr Arg Pro Gly Leu His
2475                2480                2485                2490

CGG TTT GCC GTC CTG CAG GAG AAC GTG GCC TGG GGT AAT GGG CGA GTC      7538
Arg Phe Ala Val Leu Gln Glu Asn Val Ala Trp Gly Asn Gly Arg Val
            2495                2500                2505

AGT GTG ACC AGG GTG ATC ACG GTC CAG GTG GCA AAC TTC ACC CTG CGG      7586
Ser Val Thr Arg Val Ile Thr Val Gln Val Ala Asn Phe Thr Leu Arg
            2510                2515                2520

CTG GAG CAG AGA CAG TGG AAG GTC ACG GTG AAC GGT GTG GAC ATG AAG      7634
Leu Glu Gln Arg Gln Trp Lys Val Thr Val Asn Gly Val Asp Met Lys
            2525                2530                2535

CTG CCC GTG GTG CTG GCC AAC GGC CAG ATC CGT GCC TCC CAG CAT GGT      7682
Leu Pro Val Val Leu Ala Asn Gly Gln Ile Arg Ala Ser Gln His Gly
            2540                2545                2550

TCA GAT GTT GTG ATT GAG ACC GAC TTC GGC CTG CGT GTG GCC TAC GAC      7730
Ser Asp Val Val Ile Glu Thr Asp Phe Gly Leu Arg Val Ala Tyr Asp
```

```
                    2555                2560                2565                2570
CTT GTG TAC TAT GTG CGG GTC ACC GTC CCT GGA AAC TAC TAC CAG CTG                      7778
Leu Val Tyr Tyr Val Arg Val Thr Val Pro Gly Asn Tyr Tyr Gln Leu
                    2575                2580                2585

ATG TGT GGC CTG TGT GGG GGA TCC ACTAGTTAGT TAGTTAGGGT AC                             7824
Met Cys Gly Leu Cys Gly Gly Ser
                    2590
```

(2) INFORMATION FOR SEQ ID NO: 7:

(i) SEQUENCE CHARACTERISTICS:
        (A) LENGTH: 2594 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Gly Ala Leu Trp Ser Trp Trp Ile Leu Trp Ala Gly Ala Thr Leu
  1               5                  10                  15

Leu Trp Gly Leu Thr Gln Glu Ala Ser Val Asp Leu Lys Asn Thr Gly
             20                  25                  30

Arg Glu Glu Phe Leu Thr Ala Phe Leu Gln Asn Tyr Gln Leu Ala Tyr
         35                  40                  45

Ser Lys Ala Tyr Pro Arg Leu Leu Ile Ser Ser Leu Ser Glu Ser Pro
     50                  55                  60

Ala Ser Val Ser Ile Leu Ser Gln Ala Asp Asn Thr Ser Lys Lys Val
 65                  70                  75                  80

Thr Val Arg Pro Gly Glu Ser Val Met Val Asn Ile Ser Ala Lys Ala
                 85                  90                  95

Glu Met Ile Gly Ser Lys Ile Phe Gln His Ala Val Val Ile His Ser
            100                 105                 110

Asp Tyr Ala Ile Ser Val Gln Ala Leu Asn Ala Lys Pro Asp Thr Ala
        115                 120                 125

Glu Leu Thr Leu Leu Arg Pro Ile Gln Ala Leu Gly Thr Glu Tyr Phe
    130                 135                 140

Val Leu Thr Pro Pro Gly Thr Ser Ala Arg Asn Val Lys Glu Phe Ala
145                 150                 155                 160

Val Val Ala Gly Ala Ala Gly Ala Ser Val Ser Val Thr Leu Lys Gly
                165                 170                 175

Ser Val Thr Phe Asn Gly Lys Phe Tyr Pro Ala Gly Asp Val Leu Arg
            180                 185                 190

Val Thr Leu Gln Pro Tyr Asn Val Ala Gln Leu Gln Ser Ser Val Asp
        195                 200                 205

Leu Ser Gly Ser Lys Val Thr Ala Ser Pro Val Ala Val Leu Ser
    210                 215                 220

Gly His Ser Cys Ala Gln Lys His Thr Thr Cys Asn His Val Val Glu
225                 230                 235                 240

Gln Leu Leu Pro Thr Ser Ala Trp Gly Thr His Tyr Val Val Pro Thr
                245                 250                 255

Leu Ala Ser Gln Ser Arg Tyr Asp Leu Ala Phe Val Val Ala Ser Gln
            260                 265                 270

Ala Thr Lys Leu Thr Tyr Asn His Gly Gly Ile Thr Gly Ser Arg Gly
        275                 280                 285

Leu Gln Ala Gly Asp Val Val Glu Phe Glu Val Arg Pro Ser Trp Pro
    290                 295                 300
```

-continued

```
Leu Tyr Leu Ser Ala Asn Val Gly Ile Gln Val Leu Phe Gly Thr
305                 310                 315                 320

Gly Ala Ile Arg Asn Glu Val Thr Tyr Asp Pro Tyr Leu Val Leu Ile
            325                 330                 335

Pro Asp Val Ala Ala Tyr Cys Pro Ala Tyr Val Val Lys Ser Val Pro
            340                 345                 350

Gly Cys Glu Gly Val Ala Leu Val Val Ala Gln Thr Lys Ala Ile Ser
            355                 360                 365

Gly Leu Thr Ile Asp Gly His Ala Val Gly Ala Lys Leu Thr Trp Glu
            370                 375                 380

Ala Val Pro Gly Ser Glu Phe Ser Tyr Ala Glu Val Glu Leu Gly Thr
385                 390                 395                 400

Ala Asp Met Ile His Thr Ala Glu Ala Thr Thr Asn Leu Gly Leu Leu
                405                 410                 415

Thr Phe Gly Leu Ala Lys Ala Ile Gly Tyr Ala Thr Ala Ala Asp Cys
                420                 425                 430

Gly Arg Thr Val Leu Ser Pro Val Glu Pro Ser Cys Glu Gly Met Gln
            435                 440                 445

Cys Ala Ala Gly Gln Arg Cys Gln Val Val Gly Gly Lys Ala Gly Cys
450                 455                 460

Val Ala Glu Ser Thr Ala Val Cys Arg Ala Gln Gly Asp Pro His Tyr
465                 470                 475                 480

Thr Thr Phe Asp Gly Arg Arg Tyr Asp Met Met Gly Thr Cys Ser Tyr
                485                 490                 495

Thr Met Val Glu Leu Cys Ser Glu Asp Asp Thr Leu Pro Ala Phe Ser
                500                 505                 510

Val Glu Ala Lys Asn Glu His Arg Gly Ser Arg Val Ser Tyr Val
            515                 520                 525

Gly Leu Val Thr Val Arg Ala Tyr Ser His Ser Val Ser Leu Thr Arg
            530                 535                 540

Gly Glu Val Gly Phe Val Leu Val Asp Asn Gln Arg Ser Arg Leu Pro
545                 550                 555                 560

Val Ser Leu Ser Glu Gly Arg Leu Arg Val Tyr Gln Ser Gly Pro Arg
                565                 570                 575

Ala Val Val Glu Leu Val Phe Gly Leu Val Val Thr Tyr Asp Trp Asp
                580                 585                 590

Cys Gln Leu Ala Leu Ser Leu Pro Ala Arg Phe Gln Asp Gln Val Cys
            595                 600                 605

Gly Leu Cys Gly Asn Tyr Asn Gly Asp Pro Ala Asp Asp Phe Leu Thr
610                 615                 620

Pro Asp Gly Ala Leu Ala Pro Asp Ala Val Glu Phe Ala Ser Ser Trp
625                 630                 635                 640

Lys Leu Asp Asp Gly Asp Tyr Leu Cys Glu Asp Gly Cys Gln Asn Asn
                645                 650                 655

Cys Pro Ala Cys Thr Pro Gly Gln Ala Gln His Tyr Glu Gly Asp Arg
            660                 665                 670

Leu Cys Gly Met Leu Thr Lys Leu Asp Gly Pro Phe Ala Val Cys His
            675                 680                 685

Asp Thr Leu Asp Pro Arg Pro Phe Leu Glu Gln Cys Val Tyr Asp Leu
            690                 695                 700

Cys Val Val Gly Gly Glu Arg Leu Ser Leu Cys Arg Gly Leu Ser Ala
705                 710                 715                 720

Tyr Ala Gln Ala Cys Leu Glu Leu Gly Ile Ser Val Gly Asp Trp Arg
```

-continued

```
                725                 730                 735
Ser Pro Ala Asn Cys Pro Leu Ser Cys Pro Ala Asn Ser Arg Tyr Glu
                740                 745                 750

Leu Cys Gly Pro Ala Cys Pro Thr Ser Cys Asn Gly Ala Ala Ala Pro
                755                 760                 765

Ser Asn Cys Ser Gly Arg Pro Cys Val Glu Gly Cys Val Cys Leu Pro
770                 775                 780

Gly Phe Val Ala Ser Gly Ala Cys Val Pro Ala Ser Ser Cys Gly
785                 790                 795                 800

Cys Thr Phe Gln Gly Leu Gln Leu Ala Pro Gly Gln Glu Val Trp Ala
                805                 810                 815

Asp Glu Leu Cys Gln Arg Arg Cys Thr Cys Asn Gly Ala Thr His Gln
                820                 825                 830

Val Thr Cys Arg Asp Lys Gln Ser Cys Pro Ala Gly Glu Arg Cys Ser
                835                 840                 845

Val Gln Asn Gly Leu Leu Gly Cys Tyr Pro Asp Arg Phe Gly Thr Cys
850                 855                 860

Gln Gly Ser Gly Asp Pro His Tyr Val Ser Phe Asp Gly Arg Arg Phe
865                 870                 875                 880

Asp Phe Met Gly Thr Cys Thr Tyr Leu Leu Val Gly Ser Cys Gly Gln
                885                 890                 895

Asn Ala Ala Leu Pro Ala Phe Arg Val Leu Val Glu Asn Glu His Arg
                900                 905                 910

Gly Ser Gln Thr Val Ser Tyr Thr Arg Ala Val Arg Val Glu Ala Arg
                915                 920                 925

Gly Val Lys Val Ala Val Arg Arg Glu Tyr Pro Gly Gln Val Leu Val
                930                 935                 940

Asp Asp Val Leu Gln Tyr Leu Pro Phe Gln Ala Ala Asp Gly Gln Val
945                 950                 955                 960

Gln Val Phe Arg Gln Gly Arg Asp Ala Val Val Arg Thr Asp Phe Gly
                965                 970                 975

Leu Thr Val Thr Tyr Asp Trp Asn Ala Arg Val Thr Ala Lys Val Pro
                980                 985                 990

Ser Ser Tyr Ala Glu Ala Leu Cys Gly Leu Cys Gly Asn Phe Asn Gly
                995                 1000                1005

Asp Pro Ala Asp Asp Leu Ala Leu Arg Gly Gly Gln Ala Ala Asn
                1010                1015                1020

Ala Leu Ala Phe Gly Asn Ser Trp Gln Glu Glu Thr Arg Pro Gly Cys
1025                1030                1035                1040

Gly Ala Thr Glu Pro Gly Asp Cys Pro Lys Leu Asp Ser Leu Val Ala
                1045                1050                1055

Gln Gln Leu Gln Ser Lys Asn Glu Cys Gly Ile Leu Ala Asp Pro Lys
                1060                1065                1070

Gly Pro Phe Arg Glu Cys His Ser Lys Leu Asp Pro Gln Gly Ala Val
                1075                1080                1085

Arg Asp Cys Val Tyr Asp Arg Cys Leu Leu Pro Gly Gln Ser Gly Pro
                1090                1095                1100

Leu Cys Asp Ala Leu Ala Thr Tyr Ala Ala Ala Cys Gln Ala Ala Gly
1105                1110                1115                1120

Ala Thr Val His Pro Trp Arg Ser Glu Glu Leu Cys Pro Leu Ser Cys
                1125                1130                1135

Pro Pro His Ser His Tyr Glu Ala Cys Ser Tyr Gly Cys Pro Leu Ser
                1140                1145                1150
```

-continued

```
Cys Gly Asp Leu Pro Val Pro Gly Gly Cys Ser Glu Cys His Glu
        1155                1160                1165
Gly Cys Val Cys Asp Glu Gly Phe Ala Leu Ser Gly Glu Ser Cys Leu
    1170                1175                1180
Pro Leu Ala Ser Cys Gly Cys Val His Gln Gly Thr Tyr His Pro Pro
1185                1190                1195                1200
Gly Gln Thr Phe Tyr Pro Gly Pro Gly Cys Asp Ser Leu Cys His Cys
                1205                1210                1215
Gln Glu Gly Gly Leu Val Ser Cys Glu Ser Ser Cys Gly Pro His
        1220                1225                1230
Glu Ala Cys Gln Pro Ser Gly Gly Ser Leu Gly Cys Val Ala Val Gly
        1235                1240                1245
Ser Ser Thr Cys Gln Ala Ser Gly Asp Pro His Tyr Thr Thr Phe Asp
    1250                1255                1260
Gly Arg Arg Phe Asp Phe Met Gly Thr Cys Val Tyr Val Leu Ala Gln
1265                1270                1275                1280
Thr Cys Gly Thr Arg Pro Gly Leu His Arg Phe Ala Val Leu Gln Glu
        1285                1290                1295
Asn Val Ala Trp Gly Asn Gly Arg Val Ser Val Thr Arg Val Ile Thr
        1300                1305                1310
Val Gln Val Ala Asn Phe Thr Leu Arg Leu Glu Gln Arg Gln Trp Lys
    1315                1320                1325
Val Thr Val Asn Gly Val Asp Met Lys Leu Pro Val Val Leu Ala Asn
        1330                1335                1340
Gly Gln Ile Arg Ala Ser Gln His Gly Ser Asp Val Val Ile Glu Thr
1345                1350                1355                1360
Asp Phe Gly Leu Arg Val Ala Tyr Asp Leu Val Tyr Tyr Val Arg Val
                1365                1370                1375
Thr Val Pro Gly Asn Tyr Tyr Gln Gln Met Cys Gly Leu Cys Gly Asn
                1380                1385                1390
Tyr Asn Gly Asp Pro Lys Asp Asp Phe Gln Lys Pro Asn Gly Ser Gln
        1395                1400                1405
Ala Gly Asn Ala Asn Glu Phe Gly Asn Ser Trp Glu Glu Val Val Pro
    1410                1415                1420
Asp Ser Pro Cys Leu Pro Pro Thr Pro Cys Pro Pro Gly Ser Glu Asp
1425                1430                1435                1440
Cys Ile Pro Ser His Lys Cys Pro Pro Glu Leu Glu Lys Lys Tyr Gln
                1445                1450                1455
Lys Glu Glu Phe Cys Gly Leu Leu Ser Ser Pro Thr Gly Pro Leu Ser
                1460                1465                1470
Ser Cys His Lys Leu Val Asp Pro Gln Gly Pro Leu Lys Asp Cys Ile
        1475                1480                1485
Phe Asp Leu Cys Leu Gly Gly Gly Asn Leu Ser Ile Leu Cys Ser Asn
        1490                1495                1500
Ile His Ala Tyr Val Ser Ala Cys Gln Ala Gly Gly His Val Glu
1505                1510                1515                1520
Pro Trp Arg Thr Glu Thr Phe Cys Pro Met Glu Cys Pro Pro Asn Ser
                1525                1530                1535
His Tyr Glu Leu Cys Ala Asp Thr Cys Ser Leu Gly Cys Ser Ala Leu
        1540                1545                1550
Ser Ala Pro Pro Gln Cys Gln Asp Gly Cys Ala Glu Gly Cys Gln Cys
        1555                1560                1565
```

```
-continued

Asp Ser Gly Phe Leu Tyr Asn Gly Gln Ala Cys Val Pro Ile Gln Gln
    1570                1575                1580

Cys Gly Cys Tyr His Asn Gly Val Tyr Tyr Glu Pro Glu Gln Thr Val
1585                1590                1595                1600

Leu Ile Asp Asn Cys Arg Gln Cys Thr Cys His Ala Gly Lys Gly
                1605                1610                1615

Met Val Cys Gln Glu His Ser Cys Lys Pro Gly Gln Val Cys Gln Pro
    1620                1625                1630

Ser Gly Gly Ile Leu Ser Cys Val Thr Lys Asp Pro Cys His Gly Val
                1635                1640                1645

Thr Cys Arg Pro Gln Glu Thr Cys Lys Glu Gln Gly Gly Gln Gly Val
    1650                1655                1660

Cys Leu Pro Asn Tyr Glu Ala Thr Cys Trp Leu Trp Gly Asp Pro His
1665                1670                1675                1680

Tyr His Ser Phe Asp Gly Arg Lys Phe Asp Phe Gln Gly Thr Cys Asn
                1685                1690                1695

Tyr Val Leu Ala Thr Thr Gly Cys Pro Gly Val Ser Thr Gln Gly Leu
            1700                1705                1710

Thr Pro Phe Thr Val Thr Thr Lys Asn Gln Asn Arg Gly Asn Pro Ala
    1715                1720                1725

Val Ser Tyr Val Arg Val Val Thr Val Ala Ala Leu Gly Thr Asn Ile
        1730                1735                1740

Ser Ile His Lys Asp Glu Ile Gly Lys Val Arg Val Asn Gly Val Leu
1745                1750                1755                1760

Thr Ala Leu Pro Val Ser Val Ala Asp Gly Arg Ile Ser Val Thr Gln
                1765                1770                1775

Gly Ala Ser Lys Ala Leu Leu Val Ala Asp Phe Gly Leu Gln Val Ser
        1780                1785                1790

Tyr Asp Trp Asn Trp Arg Val Asp Val Thr Leu Pro Ser Ser Tyr His
        1795                1800                1805

Gly Ala Val Cys Gly Leu Cys Gly Asn Met Asp Arg Asn Pro Asn Asn
    1810                1815                1820

Asp Gln Val Phe Pro Asn Gly Thr Leu Ala Pro Ser Ile Pro Ile Trp
1825                1830                1835                1840

Gly Gly Ser Trp Arg Ala Pro Gly Trp Asp Pro Leu Cys Trp Asp Glu
            1845                1850                1855

Cys Arg Gly Ser Cys Pro Thr Cys Pro Glu Asp Arg Leu Glu Gln Tyr
        1860                1865                1870

Glu Gly Pro Gly Phe Cys Gly Pro Leu Ala Pro Gly Thr Gly Pro
        1875                1880                1885

Phe Thr Thr Cys His Ala His Val Pro Pro Glu Ser Phe Phe Lys Gly
    1890                1895                1900

Cys Val Leu Asp Val Cys Met Gly Gly Gly Asp Arg Asp Ile Leu Cys
1905                1910                1915                1920

Lys Ala Leu Ala Ser Tyr Val Ala Ala Cys Gln Ala Ala Gly Val Val
                1925                1930                1935

Ile Glu Asp Trp Arg Ala Gln Val Gly Cys Glu Ile Thr Cys Pro Glu
        1940                1945                1950

Asn Ser His Tyr Glu Val Cys Gly Pro Pro Cys Pro Ala Ser Cys Pro
        1955                1960                1965

Ser Pro Ala Pro Leu Thr Thr Pro Ala Val Cys Glu Gly Pro Cys Val
    1970                1975                1980

Glu Gly Cys Gln Cys Asp Ala Gly Phe Val Leu Ser Ala Asp Arg Cys
```

-continued

```
1985              1990              1995              2000
Val Pro Leu Asn Asn Gly Cys Gly Cys Trp Ala Asn Gly Thr Tyr His
              2005              2010              2015
Glu Ala Gly Ser Glu Phe Trp Ala Asp Gly Thr Cys Ser Gln Trp Cys
              2020              2025              2030
Arg Cys Gly Pro Gly Gly Ser Leu Val Cys Thr Pro Ala Ser Cys
              2035              2040              2045
Gly Leu Gly Glu Val Cys Gly Leu Leu Pro Ser Gly Gln His Gly Cys
              2050              2055              2060
Gln Pro Val Ser Thr Ala Glu Cys Gln Ala Trp Gly Asp Pro His Tyr
2065              2070              2075              2080
Val Thr Leu Asp Gly His Arg Phe Asn Phe Gln Gly Thr Cys Glu Tyr
              2085              2090              2095
Leu Leu Ser Ala Pro Cys His Gly Pro Pro Leu Gly Ala Glu Asn Phe
              2100              2105              2110
Thr Val Thr Val Ala Asn Glu His Arg Gly Ser Gln Ala Val Ser Tyr
              2115              2120              2125
Thr Arg Ser Val Thr Leu Gln Ile Tyr Asn His Ser Leu Thr Leu Ser
              2130              2135              2140
Ala Arg Trp Pro Arg Lys Leu Gln Val Asp Gly Val Phe Val Thr Leu
2145              2150              2155              2160
Pro Phe Gln Leu Asp Ser Leu Leu His Ala His Leu Ser Gly Ala Asp
              2165              2170              2175
Val Val Val Thr Thr Thr Ser Gly Leu Ser Leu Ala Phe Asp Gly Asp
              2180              2185              2190
Ser Phe Val Arg Leu Arg Val Pro Ala Ala Tyr Ala Gly Ser Leu Cys
              2195              2200              2205
Gly Leu Cys Gly Asn Tyr Asn Gln Asp Pro Ala Asp Asp Leu Lys Ala
              2210              2215              2220
Val Gly Gly Lys Pro Ala Gly Trp Gln Val Gly Gly Ala Gln Gly Cys
2225              2230              2235              2240
Gly Glu Cys Val Ser Lys Pro Cys Pro Ser Pro Cys Thr Pro Glu Gln
              2245              2250              2255
Gln Glu Ser Phe Gly Gly Pro Asp Ala Cys Gly Val Ile Ser Ala Thr
              2260              2265              2270
Asp Gly Pro Leu Ala Pro Cys His Gly Leu Val Pro Pro Ala Gln Tyr
              2275              2280              2285
Phe Gln Gly Cys Leu Leu Asp Ala Cys Gln Val Gln Gly His Pro Gly
              2290              2295              2300
Gly Leu Cys Pro Ala Val Ala Thr Tyr Val Ala Ala Cys Gln Ala Ala
2305              2310              2315              2320
Gly Ala Gln Leu Arg Glu Trp Arg Arg Pro Asp Phe Cys Pro Phe Gln
              2325              2330              2335
Cys Pro Ala His Ser His Tyr Glu Leu Cys Gly Asp Ser Cys Pro Gly
              2340              2345              2350
Ser Cys Pro Ser Leu Ser Ala Pro Glu Gly Cys Glu Ser Ala Cys Arg
              2355              2360              2365
Glu Gly Cys Val Cys Asp Ala Gly Phe Val Leu Ser Gly Asp Thr Cys
              2370              2375              2380
Val Pro Val Gly Gln Cys Gly Cys Leu His Asp Asp Arg Tyr Tyr Pro
2385              2390              2395              2400
Leu Gly Gln Thr Phe Tyr Pro Gly Pro Gly Cys Asp Ser Leu Cys Arg
              2405              2410              2415
```

```
Cys Arg Glu Gly Gly Glu Val Ser Cys Glu Pro Ser Ser Cys Gly Pro
        2420                2425                2430

His Glu Thr Cys Arg Pro Ser Gly Gly Ser Leu Gly Cys Val Ala Val
        2435                2440                2445

Gly Ser Thr Thr Cys Gln Ala Ser Gly Asp Pro His Tyr Thr Thr Phe
        2450                2455                2460

Asp Gly Arg Arg Phe Asp Phe Met Gly Thr Cys Val Tyr Val Leu Ala
2465                2470                2475                2480

Gln Thr Cys Gly Thr Arg Pro Gly Leu His Arg Phe Ala Val Leu Gln
        2485                2490                2495

Glu Asn Val Ala Trp Gly Asn Gly Arg Val Ser Val Thr Arg Val Ile
        2500                2505                2510

Thr Val Gln Val Ala Asn Phe Thr Leu Arg Leu Glu Gln Arg Gln Trp
        2515                2520                2525

Lys Val Thr Val Asn Gly Val Asp Met Lys Leu Pro Val Val Leu Ala
        2530                2535                2540

Asn Gly Gln Ile Arg Ala Ser Gln His Gly Ser Asp Val Val Ile Glu
2545                2550                2555                2560

Thr Asp Phe Gly Leu Arg Val Ala Tyr Asp Leu Val Tyr Tyr Val Arg
        2565                2570                2575

Val Thr Val Pro Gly Asn Tyr Tyr Gln Leu Met Cys Gly Leu Cys Gly
        2580                2585                2590

Gly Ser
```

(2) INFORMATION FOR SEQ ID NO: 8:

(i) SEQUENCE CHARACTERISTICS:
        (A) LENGTH: 16382 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 9..16223

(xi) SEQUENCE DESCRIPTION: SEQ ID NO: 8:

```
CTGCAGCC ATG GGT GCC CTA TGG AGC TGG TGG ATA CTC TGG GCT GGA GCA      50
         Met Gly Ala Leu Trp Ser Trp Trp Ile Leu Trp Ala Gly Ala
         2595                2600                2605

ACC CTC CTG TGG GGA TTG ACC CAG GAG GCT TCA GTG GAC CTC AAG AAC       98
Thr Leu Leu Trp Gly Leu Thr Gln Glu Ala Ser Val Asp Leu Lys Asn
2610                2615                2620

ACT GGC AGA GAG GAA TTC CTC ACA GCC TTC CTG CAG AAC TAT CAG CTG      146
Thr Gly Arg Glu Glu Phe Leu Thr Ala Phe Leu Gln Asn Tyr Gln Leu
2625                2630                2635                2640

GCC TAC AGC AAG GCC TAC CCC CGC CTC CTT ATC TCC AGT CTG TCA GAG      194
Ala Tyr Ser Lys Ala Tyr Pro Arg Leu Leu Ile Ser Ser Leu Ser Glu
        2645                2650                2655

AGC CCC GCT TCA GTC TCC ATC CTC AGC CAG GCA GAC AAC ACC TCA AAG      242
Ser Pro Ala Ser Val Ser Ile Leu Ser Gln Ala Asp Asn Thr Ser Lys
        2660                2665                2670

AAG GTC ACA GTG AGG CCC GGG GAG TCG GTC ATG GTC AAC ATC AGT GCC      290
Lys Val Thr Val Arg Pro Gly Glu Ser Val Met Val Asn Ile Ser Ala
        2675                2680                2685

AAG GCT GAG ATG ATA GGC AGC AAG ATC TTC CAG CAT GCG GTG GTG ATC      338
Lys Ala Glu Met Ile Gly Ser Lys Ile Phe Gln His Ala Val Val Ile
```

-continued

```
         2690                2695                2700
CAT TCT GAC TAT GCC ATC TCT GTG CAG GCA CTA AAT GCC AAG CCT GAC      386
His Ser Asp Tyr Ala Ile Ser Val Gln Ala Leu Asn Ala Lys Pro Asp
2705                2710                2715                2720

ACA GCG GAG CTG ACA CTG CTG CGG CCC ATC CAG GCC CTA GGC ACC GAG      434
Thr Ala Glu Leu Thr Leu Leu Arg Pro Ile Gln Ala Leu Gly Thr Glu
            2725                2730                2735

TAT TTT GTG CTC ACA CCC CCC GGC ACC TCA GCC AGG AAT GTC AAG GAG      482
Tyr Phe Val Leu Thr Pro Pro Gly Thr Ser Ala Arg Asn Val Lys Glu
        2740                2745                2750

TTT GCC GTG GTG GCC GGT GCC GCA GGT GCC TCG GTC AGT GTC ACG CTG      530
Phe Ala Val Val Ala Gly Ala Ala Gly Ala Ser Val Ser Val Thr Leu
            2755                2760                2765

AAG GGG TCA GTG ACA TTC AAT GGC AAG TTC TAT CCA GCA GGC GAT GTC      578
Lys Gly Ser Val Thr Phe Asn Gly Lys Phe Tyr Pro Ala Gly Asp Val
        2770                2775                2780

CTA AGA GTG ACT CTA CAG CCC TAC AAT GTG GCC CAG CTA CAG AGC TCA      626
Leu Arg Val Thr Leu Gln Pro Tyr Asn Val Ala Gln Leu Gln Ser Ser
2785                2790                2795                2800

GTG GAT CTC TCG GGG TCA AAG GTC ACA GCT AGT AGC CCC GTG GCT GTC      674
Val Asp Leu Ser Gly Ser Lys Val Thr Ala Ser Ser Pro Val Ala Val
            2805                2810                2815

CTC TCT GGC CAC AGC TGT GCG CAG AAA CAT ACG ACC TGC AAC CAT GTG      722
Leu Ser Gly His Ser Cys Ala Gln Lys His Thr Thr Cys Asn His Val
        2820                2825                2830

GTT GAG CAG CTG CTA CCC ACG TCT GCC TGG GGC ACC CAC TAT GTA GTA      770
Val Glu Gln Leu Leu Pro Thr Ser Ala Trp Gly Thr His Tyr Val Val
            2835                2840                2845

CCC ACG CTG GCC TCC CAA TCT CGC TAT GAT TTG GCC TTC GTT GTG GCC      818
Pro Thr Leu Ala Ser Gln Ser Arg Tyr Asp Leu Ala Phe Val Val Ala
        2850                2855                2860

AGC CAG GCC ACA AAG CTG ACC TAC AAC CAT GGG GGT ATC ACT GGC TCC      866
Ser Gln Ala Thr Lys Leu Thr Tyr Asn His Gly Gly Ile Thr Gly Ser
2865                2870                2875                2880

CGT GGG CTC CAG GCA GGT GAT GTG GTA GAG TTT GAG GTC CGG CCA TCC      914
Arg Gly Leu Gln Ala Gly Asp Val Val Glu Phe Glu Val Arg Pro Ser
            2885                2890                2895

TGG CCA CTC TAC CTG TCT GCA AAT GTG GGC ATC CAG GTC CTG TTG TTT      962
Trp Pro Leu Tyr Leu Ser Ala Asn Val Gly Ile Gln Val Leu Leu Phe
        2900                2905                2910

GGC ACA GGT GCC ATA AGG AAT GAA GTG ACT TAT GAC CCC TAC CTG GTC     1010
Gly Thr Gly Ala Ile Arg Asn Glu Val Thr Tyr Asp Pro Tyr Leu Val
            2915                2920                2925

CTG ATC CCA GAT GTG GCG GCC TAC TGC CCA GCC TAT GTG GTC AAG AGT     1058
Leu Ile Pro Asp Val Ala Ala Tyr Cys Pro Ala Tyr Val Val Lys Ser
        2930                2935                2940

GTA CCA GGC TGT GAG GGC GTG GCC CTG GTA GTG GCA CAG ACG AAG GCT     1106
Val Pro Gly Cys Glu Gly Val Ala Leu Val Val Ala Gln Thr Lys Ala
2945                2950                2955                2960

ATC AGC GGG CTG ACC ATA GAT GGG CAT GCA GTG GGG GCC AAG CTC ACC     1154
Ile Ser Gly Leu Thr Ile Asp Gly His Ala Val Gly Ala Lys Leu Thr
            2965                2970                2975

TGG GAG GCT GTG CCA GGC AGT GAG TTC TCG TAT GCT GAA GTG GAG CTC     1202
Trp Glu Ala Val Pro Gly Ser Glu Phe Ser Tyr Ala Glu Val Glu Leu
        2980                2985                2990

GGC ACA GCT GAC ATG ATC CAC ACG GCC GAG GCC ACC ACC AAC TTG GGA     1250
Gly Thr Ala Asp Met Ile His Thr Ala Glu Ala Thr Thr Asn Leu Gly
            2995                3000                3005

CTG CTC ACC TTC GGG CTG GCC AAG GCT ATA GGC TAC GCA ACA GCT GCT     1298
```

```
                                                                -continued

Leu Leu Thr Phe Gly Leu Ala Lys Ala Ile Gly Tyr Ala Thr Ala Ala
    3010                3015                3020

GAT TGC GGC CGG ACT GTA CTG TCC CCA GTG GAG CCC TCC TGC GAA GGC      1346
Asp Cys Gly Arg Thr Val Leu Ser Pro Val Glu Pro Ser Cys Glu Gly
3025                3030                3035                3040

ATG CAG TGC GCA GCC GGG CAG CGC TGC CAG GTG GTA GGC GGG AAG GCC      1394
Met Gln Cys Ala Ala Gly Gln Arg Cys Gln Val Val Gly Gly Lys Ala
                3045                3050                3055

GGG TGT GTG GCG GAG TCC ACC GCT GTC TGC CGC GCC CAG GGC GAC CCC      1442
Gly Cys Val Ala Glu Ser Thr Ala Val Cys Arg Ala Gln Gly Asp Pro
            3060                3065                3070

CAT TAC ACC ACC TTC GAC GGC CGT CGC TAC GAC ATG ATG GGC ACC TGT      1490
His Tyr Thr Thr Phe Asp Gly Arg Arg Tyr Asp Met Met Gly Thr Cys
        3075                3080                3085

TCG TAC ACG ATG GTG GAG CTG TGC AGC GAG GAC GAC ACC CTG CCC GCC      1538
Ser Tyr Thr Met Val Glu Leu Cys Ser Glu Asp Asp Thr Leu Pro Ala
    3090                3095                3100

TTC AGC GTG GAG GCC AAG AAC GAG CAC CGG GGC AGC CGC CGC GTC TCC      1586
Phe Ser Val Glu Ala Lys Asn Glu His Arg Gly Ser Arg Arg Val Ser
3105                3110                3115                3120

TAC GTG GGC CTC GTC ACT GTG CGC GCC TAC AGC CAC TCT GTG TCG CTG      1634
Tyr Val Gly Leu Val Thr Val Arg Ala Tyr Ser His Ser Val Ser Leu
                3125                3130                3135

ACC CGC GGT GAA GTT GGC TTC GTC CTG GTT GAC AAC CAG CGC TCG CGC      1682
Thr Arg Gly Glu Val Gly Phe Val Leu Val Asp Asn Gln Arg Ser Arg
            3140                3145                3150

CTG CCA GTC TCC CTG AGT GAG GGT CGC CTG CGT GTG TAC CAG AGC GGA      1730
Leu Pro Val Ser Leu Ser Glu Gly Arg Leu Arg Val Tyr Gln Ser Gly
        3155                3160                3165

CCA CGG GCC GTG GTG GAG CTG GTC TTT GGG CTG GTG GTC ACT TAT GAC      1778
Pro Arg Ala Val Val Glu Leu Val Phe Gly Leu Val Val Thr Tyr Asp
    3170                3175                3180

TGG GAC TGC CAG CTG GCA CTC AGC CTG CCT GCA CGC TTC CAA GAC CAG      1826
Trp Asp Cys Gln Leu Ala Leu Ser Leu Pro Ala Arg Phe Gln Asp Gln
3185                3190                3195                3200

GTG TGC GGG CTG TGT GGC AAC TAT AAT GGT GAC CCA GCA GAC GAC TTC      1874
Val Cys Gly Leu Cys Gly Asn Tyr Asn Gly Asp Pro Ala Asp Asp Phe
                3205                3210                3215

CTC ACG CCT GAC GGG GCT CTG GCT CCT GAC GCT GTG GAG TTC GCA AGT      1922
Leu Thr Pro Asp Gly Ala Leu Ala Pro Asp Ala Val Glu Phe Ala Ser
            3220                3225                3230

AGC TGG AAG CTG GAT GAT GGG GAC TAC CTG TGT GAG GAT GGC TGC CAG      1970
Ser Trp Lys Leu Asp Asp Gly Asp Tyr Leu Cys Glu Asp Gly Cys Gln
        3235                3240                3245

AAC AAC TGT CCC GCC TGC ACC CCA GGC CAG GCC CAA CAC TAT GAG GGC      2018
Asn Asn Cys Pro Ala Cys Thr Pro Gly Gln Ala Gln His Tyr Glu Gly
    3250                3255                3260

GAC CGA CTC TGT GGC ATG CTG ACC AAG CTC GAT GGC CCC TTC GCT GTC      2066
Asp Arg Leu Cys Gly Met Leu Thr Lys Leu Asp Gly Pro Phe Ala Val
3265                3270                3275                3280

TGC CAT GAC ACC CTG GAC CCC AGG CCC TTC CTG GAG CAG TGT GTA TAT      2114
Cys His Asp Thr Leu Asp Pro Arg Pro Phe Leu Glu Gln Cys Val Tyr
                3285                3290                3295

GAC CTG TGT GTG GTC GGT GGG GAG CGG CTC AGC CTG TGC CGT GGC CTC      2162
Asp Leu Cys Val Val Gly Gly Glu Arg Leu Ser Leu Cys Arg Gly Leu
            3300                3305                3310

AGC GCC TAT GCC CAG GCC TGT CTG GAG CTT GGC ATC TCG GTT GGG GAC      2210
Ser Ala Tyr Ala Gln Ala Cys Leu Glu Leu Gly Ile Ser Val Gly Asp
        3315                3320                3325
```

```
                              -continued

TGG AGA TCA CCA GCC AAC TGC CCC CTG TCC TGC CCT GCC AAC AGC CGC      2258
Trp Arg Ser Pro Ala Asn Cys Pro Leu Ser Cys Pro Ala Asn Ser Arg
        3330                3335                3340

TAT GAG CTC TGC GGC CCT GCT TGC CCG ACC TCC TGC AAC GGG GCT GCG      2306
Tyr Glu Leu Cys Gly Pro Ala Cys Pro Thr Ser Cys Asn Gly Ala Ala
3345                3350                3355                3360

GCG CCG TCC AAC TGC TCC GGG CGC CCC TGC GTG GAG GGC TGC GTG TGC      2354
Ala Pro Ser Asn Cys Ser Gly Arg Pro Cys Val Glu Gly Cys Val Cys
                3365                3370                3375

CTC CCA GGC TTC GTG GCC AGC GGC GGC GCC TGC GTG CCG GCC TCG TCG      2402
Leu Pro Gly Phe Val Ala Ser Gly Gly Ala Cys Val Pro Ala Ser Ser
        3380                3385                3390

TGT GGC TGC ACC TTC CAG GGT CTC CAG CTC GCT CCG GGC CAG GAA GTG      2450
Cys Gly Cys Thr Phe Gln Gly Leu Gln Leu Ala Pro Gly Gln Glu Val
        3395                3400                3405

TGG GCG GAC GAG TTG TGC CAA AGG CGC TGC ACC TGC AAC GGC GCC ACC      2498
Trp Ala Asp Glu Leu Cys Gln Arg Arg Cys Thr Cys Asn Gly Ala Thr
        3410                3415                3420

CAT CAG GTC ACC TGC CGC GAC AAG CAG AGC TGC CCG GCG GGT GAG CGC      2546
His Gln Val Thr Cys Arg Asp Lys Gln Ser Cys Pro Ala Gly Glu Arg
3425                3430                3435                3440

TGC AGC GTC CAG AAC GGC CTC CTG GGC TGC TAC CCC GAT CGC TTC GGG      2594
Cys Ser Val Gln Asn Gly Leu Leu Gly Cys Tyr Pro Asp Arg Phe Gly
                3445                3450                3455

ACC TGC CAG GGG TCC GGG GAC CCA CAC TAT GTG AGC TTC GAC GGC CGG      2642
Thr Cys Gln Gly Ser Gly Asp Pro His Tyr Val Ser Phe Asp Gly Arg
                3460                3465                3470

CGC TTC GAC TTC ATG GGC ACC TGC ACG TAC CTG CTG GTC GGC TCA TGC      2690
Arg Phe Asp Phe Met Gly Thr Cys Thr Tyr Leu Leu Val Gly Ser Cys
                3475                3480                3485

GGC CAG AAC GCA GCG CTG CCT GCC TTC CGG GTG CTG GTG GAA AAC GAG      2738
Gly Gln Asn Ala Ala Leu Pro Ala Phe Arg Val Leu Val Glu Asn Glu
        3490                3495                3500

CAT CGG GGC AGC CAG ACT GTG AGC TAC ACG CGC GCC GTG CGG GTG GAG      2786
His Arg Gly Ser Gln Thr Val Ser Tyr Thr Arg Ala Val Arg Val Glu
3505                3510                3515                3520

GCC CGC GGG GTG AAG GTG GCC GTG CGC CGG GAG TAC CCC GGG CAA GTG      2834
Ala Arg Gly Val Lys Val Ala Val Arg Arg Glu Tyr Pro Gly Gln Val
                3525                3530                3535

CTG GTG GAT GAC GTC CTT CAG TAT CTG CCC TTC CAA GCA GCA GAT GGG      2882
Leu Val Asp Asp Val Leu Gln Tyr Leu Pro Phe Gln Ala Ala Asp Gly
                3540                3545                3550

CAG GTG CAG GTG TTC CGA CAG GGC AGG GAT GCC GTC GTG CGC ACG GAC      2930
Gln Val Gln Val Phe Arg Gln Gly Arg Asp Ala Val Val Arg Thr Asp
        3555                3560                3565

TTT GGC CTG ACT GTC ACT TAT GAC TGG AAT GCA CGA GTG ACT GCC AAG      2978
Phe Gly Leu Thr Val Thr Tyr Asp Trp Asn Ala Arg Val Thr Ala Lys
        3570                3575                3580

GTG CCC AGC AGC TAT GCT GAG GCC CTG TGT GGA CTC TGT GGG AAC TTC      3026
Val Pro Ser Ser Tyr Ala Glu Ala Leu Cys Gly Leu Cys Gly Asn Phe
3585                3590                3595                3600

AAC GGG GAC CCA GCT GAT GAC CTG GCT CTG CGG GGT GGG GGT CAA GCT      3074
Asn Gly Asp Pro Ala Asp Asp Leu Ala Leu Arg Gly Gly Gly Gln Ala
                3605                3610                3615

GCC AAT GCA CTG GCC TTT GGG AAC AGC TGG CAA GAA GAG ACG AGG CCC      3122
Ala Asn Ala Leu Ala Phe Gly Asn Ser Trp Gln Glu Glu Thr Arg Pro
        3620                3625                3630

GGC TGT GGA GCA ACT GAA CCG GGT GAC TGT CCC AAG CTG GAC TCC CTG      3170
Gly Cys Gly Ala Thr Glu Pro Gly Asp Cys Pro Lys Leu Asp Ser Leu
        3635                3640                3645
```

```
GTG GCC CAG CAG CTG CAG AGC AAG AAT GAG TGT GGA ATC CTT GCC GAC      3218
Val Ala Gln Gln Leu Gln Ser Lys Asn Glu Cys Gly Ile Leu Ala Asp
        3650                3655                3660

CCC AAG GGG CCC TTC CGG GAG TGC CAT AGC AAG CTG GAC CCC CAG GGT      3266
Pro Lys Gly Pro Phe Arg Glu Cys His Ser Lys Leu Asp Pro Gln Gly
3665            3670                3675                3680

GCC GTG CGC GAC TGT GTC TAT GAC CGC TGC CTG CTG CCA GGC CAG TCT      3314
Ala Val Arg Asp Cys Val Tyr Asp Arg Cys Leu Leu Pro Gly Gln Ser
                3685                3690                3695

GGG CCA CTG TGT GAC GCA CTG GCC ACC TAT GCT GCT GCA TGC CAG GCT      3362
Gly Pro Leu Cys Asp Ala Leu Ala Thr Tyr Ala Ala Ala Cys Gln Ala
        3700                3705                3710

GCT GGA GCC ACA GTG CAC CCC TGG AGG AGT GAA GAA CTT TGC CCA CTG      3410
Ala Gly Ala Thr Val His Pro Trp Arg Ser Glu Glu Leu Cys Pro Leu
3715            3720                3725

AGC TGC CCA CCC CAC AGC CAC TAT GAG GCG TGT TCC TAC GGC TGC CCG      3458
Ser Cys Pro Pro His Ser His Tyr Glu Ala Cys Ser Tyr Gly Cys Pro
                3730                3735                3740

CTG TCC TGT GGA GAC CTC CCA GTG CCC GGG GGC TGT GGC TCA GAA TGC      3506
Leu Ser Cys Gly Asp Leu Pro Val Pro Gly Gly Cys Gly Ser Glu Cys
3745            3750                3755                3760

CAT GAG GGC TGC GTG TGC GAT GAG GGC TTT GCG CTC AGT GGT GAG TCC      3554
His Glu Gly Cys Val Cys Asp Glu Gly Phe Ala Leu Ser Gly Glu Ser
                3765                3770                3775

TGC CTG CCC CTG GCC TCC TGT GGC TGC GTA CAC CAG GGC ACC TAC CAC      3602
Cys Leu Pro Leu Ala Ser Cys Gly Cys Val His Gln Gly Thr Tyr His
        3780                3785                3790

CCA CCA GGC CAG ACC TTC TAC CCT GGC CCC GGA TGT GAT TCC CTT TGC      3650
Pro Pro Gly Gln Thr Phe Tyr Pro Gly Pro Gly Cys Asp Ser Leu Cys
            3795                3800                3805

CAC TGC CAG GAG GGC GGC CTG GTG TCC TGT GAG TCC TCC AGC TGC GGA      3698
His Cys Gln Glu Gly Gly Leu Val Ser Cys Glu Ser Ser Ser Cys Gly
        3810                3815                3820

CCG CAC GAG GCC TGC CAG CCA TCC GGT GGC AGC TTG GGC TGT GTG GCC      3746
Pro His Glu Ala Cys Gln Pro Ser Gly Gly Ser Leu Gly Cys Val Ala
3825            3830                3835                3840

GTG GGC TCT AGC ACC TGC CAG GCG TCA GGA GAC CCC CAC TAC ACC ACC      3794
Val Gly Ser Ser Thr Cys Gln Ala Ser Gly Asp Pro His Tyr Thr Thr
                3845                3850                3855

TTC GAT GGC CGC CGC TTC GAC TTC ATG GGC ACC TGC GTG TAT GTG CTG      3842
Phe Asp Gly Arg Arg Phe Asp Phe Met Gly Thr Cys Val Tyr Val Leu
        3860                3865                3870

GCT CAG ACC TGC GGC ACC CGG CCT GGC CTG CAT CGG TTT GCC GTC CTG      3890
Ala Gln Thr Cys Gly Thr Arg Pro Gly Leu His Arg Phe Ala Val Leu
    3875                3880                3885

CAG GAG AAC GTG GCC TGG GGT AAT GGG CGA GTC AGT GTG ACC AGG GTG      3938
Gln Glu Asn Val Ala Trp Gly Asn Gly Arg Val Ser Val Thr Arg Val
    3890                3895                3900

ATC ACG GTC CAG GTG GCA AAC TTC ACC CTG CGG CTG GAG CAG AGA CAG      3986
Ile Thr Val Gln Val Ala Asn Phe Thr Leu Arg Leu Glu Gln Arg Gln
3905                3910                3915                3920

TGG AAG GTC ACG GTG AAC GGT GTG GAC ATG AAG CTG CCC GTG GTG CTG      4034
Trp Lys Val Thr Val Asn Gly Val Asp Met Lys Leu Pro Val Val Leu
            3925                3930                3935

GCC AAC GGC CAG ATC CGT GCC TCC CAG CAT GGT TCA GAT GTT GTG ATT      4082
Ala Asn Gly Gln Ile Arg Ala Ser Gln His Gly Ser Asp Val Val Ile
        3940                3945                3950

GAG ACC GAC TTC GGC CTG CGT GTG GCC TAC GAC CTT GTG TAC TAT GTG      4130
Glu Thr Asp Phe Gly Leu Arg Val Ala Tyr Asp Leu Val Tyr Tyr Val
```

-continued

```
              3955                3960                3965
CGG GTC ACC GTC CCC GGA AAC TAC TAC CAG CAG ATG TGT GGC CTG TGT        4178
Arg Val Thr Val Pro Gly Asn Tyr Tyr Gln Gln Met Cys Gly Leu Cys
          3970                3975                3980

GGG AAC TAC AAC GGC GAC CCC AAG GAT GAC TTC CAG AAG CCC AAT GGC        4226
Gly Asn Tyr Asn Gly Asp Pro Lys Asp Asp Phe Gln Lys Pro Asn Gly
3985                3990                3995                4000

TCA CAG GCA GGC AAC GCC AAT GAG TTC GGC AAC TCC TGG GAG GAG GTG        4274
Ser Gln Ala Gly Asn Ala Asn Glu Phe Gly Asn Ser Trp Glu Glu Val
              4005                4010                4015

GTG CCC GAC TCT CCC TGC CTG CCG CCC ACC CCT TGC CCG CCG GGG AGC        4322
Val Pro Asp Ser Pro Cys Leu Pro Pro Thr Pro Cys Pro Pro Gly Ser
              4020                4025                4030

GAG GAC TGT ATC CCC AGC CAC AAG TGT CCT CCC GAG CTG GAG AAG AAG        4370
Glu Asp Cys Ile Pro Ser His Lys Cys Pro Pro Glu Leu Glu Lys Lys
              4035                4040                4045

TAT CAG AAG GAG GAG TTC TGT GGG CTC CTC TCC AGC CCC ACA GGG CCA        4418
Tyr Gln Lys Glu Glu Phe Cys Gly Leu Leu Ser Ser Pro Thr Gly Pro
          4050                4055                4060

CTG TCC TCC TGC CAC AAG CTG GTG GAT CCC CAG GGT CCC TTG AAA GAT        4466
Leu Ser Ser Cys His Lys Leu Val Asp Pro Gln Gly Pro Leu Lys Asp
4065                4070                4075                4080

TGC ATC TTT GAT CTC TGC CTG GGT GGT GGG AAC CTG AGC ATT CTC TGC        4514
Cys Ile Phe Asp Leu Cys Leu Gly Gly Gly Asn Leu Ser Ile Leu Cys
              4085                4090                4095

AGC AAC ATC CAT GCC TAC GTG AGT GCT TGC CAG GCG GCT GGA GGC CAC        4562
Ser Asn Ile His Ala Tyr Val Ser Ala Cys Gln Ala Ala Gly Gly His
              4100                4105                4110

GTG GAG CCC TGG AGG ACT GAA ACT TTC TGT CCC ATG GAG TGC CCT CCG        4610
Val Glu Pro Trp Arg Thr Glu Thr Phe Cys Pro Met Glu Cys Pro Pro
          4115                4120                4125

AAC AGT CAC TAC GAG CTC TGT GCG GAC ACC TGC TCC CTG GGC TGC TCA        4658
Asn Ser His Tyr Glu Leu Cys Ala Asp Thr Cys Ser Leu Gly Cys Ser
          4130                4135                4140

GCT CTC AGT GCC CCT CCA CAG TGC CAG GAT GGG TGT GCT GAG GGC TGC        4706
Ala Leu Ser Ala Pro Pro Gln Cys Gln Asp Gly Cys Ala Glu Gly Cys
4145                4150                4155                4160

CAG TGT GAC TCC GGC TTC CTC TAC AAT GGC CAA GCC TGC GTG CCC ATC        4754
Gln Cys Asp Ser Gly Phe Leu Tyr Asn Gly Gln Ala Cys Val Pro Ile
              4165                4170                4175

CAG CAA TGC GGC TGC TAC CAC AAT GGT GTC TAC TAT GAG CCG GAG CAG        4802
Gln Gln Cys Gly Cys Tyr His Asn Gly Val Tyr Tyr Glu Pro Glu Gln
              4180                4185                4190

ACA GTC CTC ATT GAC AAC TGT CGG CAG CAG TGC ACG TGC CAT GCG GGT        4850
Thr Val Leu Ile Asp Asn Cys Arg Gln Gln Cys Thr Cys His Ala Gly
          4195                4200                4205

AAA GGC ATG GTG TGC CAG GAA CAC AGC TGC AAG CCG GGG CAG GTG TGC        4898
Lys Gly Met Val Cys Gln Glu His Ser Cys Lys Pro Gly Gln Val Cys
          4210                4215                4220

CAG CCC TCC GGA GGC ATC CTG AGC TGC GTC ACC AAA GAC CCG TGC CAC        4946
Gln Pro Ser Gly Gly Ile Leu Ser Cys Val Thr Lys Asp Pro Cys His
4225                4230                4235                4240

GGC GTG ACA TGC CGG CCA CAG GAG ACA TGC AAG GAG CAG GGT GGC CAG        4994
Gly Val Thr Cys Arg Pro Gln Glu Thr Cys Lys Glu Gln Gly Gly Gln
              4245                4250                4255

GGC GTG TGC CTG CCC AAC TAT GAG GCC ACG TGC TGG CTG TGG GGC GAC        5042
Gly Val Cys Leu Pro Asn Tyr Glu Ala Thr Cys Trp Leu Trp Gly Asp
              4260                4265                4270

CCA CAC TAC CAC TCC TTC GAT GGC CGG AAG TTT GAC TTC CAG GGC ACC        5090
```

```
Pro His Tyr His Ser Phe Asp Gly Arg Lys Phe Asp Phe Gln Gly Thr
        4275                4280                4285

TGT AAC TAT GTG CTG GCA ACA ACT GGC TGC CCG GGG GTC AGC ACC CAG      5138
Cys Asn Tyr Val Leu Ala Thr Thr Gly Cys Pro Gly Val Ser Thr Gln
    4290                4295                4300

GGC CTG ACA CCC TTC ACC GTC ACC ACC AAG AAC CAG AAC CGG GGC AAC      5186
Gly Leu Thr Pro Phe Thr Val Thr Thr Lys Asn Gln Asn Arg Gly Asn
4305                4310                4315                4320

CCT GCT GTG TCC TAC GTG AGA GTC GTC ACC GTG GCT GCC CTC GGC ACC      5234
Pro Ala Val Ser Tyr Val Arg Val Val Thr Val Ala Ala Leu Gly Thr
                4325                4330                4335

AAC ATC TCC ATC CAC AAG GAC GAG ATC GGC AAA GTC CGG GTG AAC GGT      5282
Asn Ile Ser Ile His Lys Asp Glu Ile Gly Lys Val Arg Val Asn Gly
            4340                4345                4350

GTG CTC ACA GCC TTG CCT GTC TCT GTG GCC GAC GGG CGG ATT TCA GTG      5330
Val Leu Thr Ala Leu Pro Val Ser Val Ala Asp Gly Arg Ile Ser Val
        4355                4360                4365

ACC CAG GGT GCA TCG AAG GCA CTG CTG GTG GCT GAC TTT GGA CTG CAA      5378
Thr Gln Gly Ala Ser Lys Ala Leu Leu Val Ala Asp Phe Gly Leu Gln
    4370                4375                4380

GTC AGC TAT GAC TGG AAC TGG CGG GTA GAC GTG ACG CTG CCC AGC AGC      5426
Val Ser Tyr Asp Trp Asn Trp Arg Val Asp Val Thr Leu Pro Ser Ser
4385                4390                4395                4400

TAT CAT GGC GCA GTG TGC GGG CTC TGC GGT AAC ATG GAC CGC AAC CCC      5474
Tyr His Gly Ala Val Cys Gly Leu Cys Gly Asn Met Asp Arg Asn Pro
                4405                4410                4415

AAC AAT GAC CAG GTC TTC CCT AAT GGC ACA CTG GCT CCC TCC ATA CCC      5522
Asn Asn Asp Gln Val Phe Pro Asn Gly Thr Leu Ala Pro Ser Ile Pro
            4420                4425                4430

ATC TGG GGC GGC AGC TGG CGA GCC CCA GGC TGG GAC CCA CTG TGT TGG      5570
Ile Trp Gly Gly Ser Trp Arg Ala Pro Gly Trp Asp Pro Leu Cys Trp
        4435                4440                4445

GAC GAA TGT CGG GGG TCC TGC CCA ACG TGC CCT GAG GAC CGG TTG GAG      5618
Asp Glu Cys Arg Gly Ser Cys Pro Thr Cys Pro Glu Asp Arg Leu Glu
    4450                4455                4460

CAG TAC GAG GGC CCT GGC TTC TGC GGA CCC CTG GCC CCC GGC ACA GGG      5666
Gln Tyr Glu Gly Pro Gly Phe Cys Gly Pro Leu Ala Pro Gly Thr Gly
4465                4470                4475                4480

GGC CCT TTC ACC ACC TGC CAT GCT CAT GTG CCA CCT GAG AGC TTC TTC      5714
Gly Pro Phe Thr Thr Cys His Ala His Val Pro Pro Glu Ser Phe Phe
                4485                4490                4495

AAG GGC TGT GTT CTG GAC GTC TGC ATG GGT GGT GGG GAC CGT GAC ATT      5762
Lys Gly Cys Val Leu Asp Val Cys Met Gly Gly Gly Asp Arg Asp Ile
            4500                4505                4510

CTT TGC AAG GCT CTG GCT TCC TAT GTG GCC GCC TGC CAG GCT GCT GGG      5810
Leu Cys Lys Ala Leu Ala Ser Tyr Val Ala Ala Cys Gln Ala Ala Gly
        4515                4520                4525

GTT GTC ATC GAA GAC TGG CGG GCA CAG GTT GGC TGT GAG ATC ACC TGC      5858
Val Val Ile Glu Asp Trp Arg Ala Gln Val Gly Cys Glu Ile Thr Cys
    4530                4535                4540

CCA GAA AAC AGC CAC TAT GAG GTC TGT GGC CCA CCC TGC CCG GCC AGC      5906
Pro Glu Asn Ser His Tyr Glu Val Cys Gly Pro Pro Cys Pro Ala Ser
4545                4550                4555                4560

TGT CCG TCC CCT GCA CCC CTT ACG ACG CCA GCC GTA TGT GAG GGC CCC      5954
Cys Pro Ser Pro Ala Pro Leu Thr Thr Pro Ala Val Cys Glu Gly Pro
                4565                4570                4575

TGT GTG GAG GGC TGC CAG TGC GAC GCG GGT TTC GTG TTA AGT GCT GAC      6002
Cys Val Glu Gly Cys Gln Cys Asp Ala Gly Phe Val Leu Ser Ala Asp
            4580                4585                4590
```

```
                                                          -continued

CGC TGT GTT CCC CTC AAC AAC GGC TGC GGC TGC TGG GCC AAT GGC ACC     6050
Arg Cys Val Pro Leu Asn Asn Gly Cys Gly Cys Trp Ala Asn Gly Thr
        4595                4600                4605

TAC CAC GAG GCG GGC AGT GAG TTT TGG GCT GAT GGC ACC TGC TCC CAG     6098
Tyr His Glu Ala Gly Ser Glu Phe Trp Ala Asp Gly Thr Cys Ser Gln
    4610                4615                4620

TGG TGT CGC TGC GGG CCT GGG GGT GGC TCG CTG GTC TGC ACA CCT GCC     6146
Trp Cys Arg Cys Gly Pro Gly Gly Gly Ser Leu Val Cys Thr Pro Ala
4625                4630                4635                4640

AGC TGT GGG CTG GGT GAA GTG TGT GGC CTC CTG CCA TCC GGC CAG CAC     6194
Ser Cys Gly Leu Gly Glu Val Cys Gly Leu Leu Pro Ser Gly Gln His
            4645                4650                4655

GGC TGC CAG CCC GTC AGC ACA GCT GAG TGC CAG GCG TGG GGT GAC CCC     6242
Gly Cys Gln Pro Val Ser Thr Ala Glu Cys Gln Ala Trp Gly Asp Pro
        4660                4665                4670

CAT TAC GTC ACT CTG GAT GGG CAC CGA TTC AAT TTC CAA GGC ACC TGC     6290
His Tyr Val Thr Leu Asp Gly His Arg Phe Asn Phe Gln Gly Thr Cys
    4675                4680                4685

GAG TAC CTG CTG AGT GCA CCC TGC CAC GGA CCA CCC TTG GGG GCT GAG     6338
Glu Tyr Leu Leu Ser Ala Pro Cys His Gly Pro Pro Leu Gly Ala Glu
4690                4695                4700

AAC TTC ACT GTC ACT GTA GCC AAT GAG CAC CGG GGC AGC CAG GCT GTC     6386
Asn Phe Thr Val Thr Val Ala Asn Glu His Arg Gly Ser Gln Ala Val
4705                4710                4715                4720

AGC TAC ACC CGC AGT GTC ACC CTG CAA ATC TAC AAC CAC AGC CTG ACA     6434
Ser Tyr Thr Arg Ser Val Thr Leu Gln Ile Tyr Asn His Ser Leu Thr
        4725                4730                4735

CTG AGT GCC CGC TGG CCC CGG AAG CTA CAG GTG GAC GGC GTG TTC GTC     6482
Leu Ser Ala Arg Trp Pro Arg Lys Leu Gln Val Asp Gly Val Phe Val
        4740                4745                4750

ACT CTG CCC TTC CAG CTG GAC TCG CTC CTG CAC GCA CAC CTG AGC GGC     6530
Thr Leu Pro Phe Gln Leu Asp Ser Leu Leu His Ala His Leu Ser Gly
        4755                4760                4765

GCC GAC GTG GTG GTG ACC ACA ACC TCA GGG CTC TCG CTG GCT TTC GAC     6578
Ala Asp Val Val Val Thr Thr Thr Ser Gly Leu Ser Leu Ala Phe Asp
        4770                4775                4780

GGG GAC AGC TTC GTG CGC CTG CGC GTG CCG GCG GCG TAC GCG GGC TCT     6626
Gly Asp Ser Phe Val Arg Leu Arg Val Pro Ala Ala Tyr Ala Gly Ser
4785                4790                4795                4800

CTC TGT GGC TTA TGC GGG AAC TAC AAC CAG GAC CCC GCA GAC GAC CTG     6674
Leu Cys Gly Leu Cys Gly Asn Tyr Asn Gln Asp Pro Ala Asp Asp Leu
            4805                4810                4815

AAG GCG GTG GGC GGG AAG CCC GCC GGA TGG CAG GTG GGC GGC GCC CAG     6722
Lys Ala Val Gly Gly Lys Pro Ala Gly Trp Gln Val Gly Gly Ala Gln
            4820                4825                4830

GGC TGC GGG GAA TGT GTG TCC AAG CCA TGC CCG TCG CCG TGC ACC CCA     6770
Gly Cys Gly Glu Cys Val Ser Lys Pro Cys Pro Ser Pro Cys Thr Pro
        4835                4840                4845

GAG CAG CAA GAG TCC TTC GGC GGC CCG GAC GCC TGC GGC GTG ATC TCC     6818
Glu Gln Gln Glu Ser Phe Gly Gly Pro Asp Ala Cys Gly Val Ile Ser
    4850                4855                4860

GCC ACC GAC GGC CCG CTG GCG CCC TGC CAC GGC CTT GTG CCG CCC GCG     6866
Ala Thr Asp Gly Pro Leu Ala Pro Cys His Gly Leu Val Pro Pro Ala
4865                4870                4875                4880

CAG TAC TTC CAG GGC TGC TTG CTG GAC GCC TGC CAA GTT CAG GGC CAT     6914
Gln Tyr Phe Gln Gly Cys Leu Leu Asp Ala Cys Gln Val Gln Gly His
            4885                4890                4895

CCT GGA GGC CTC TGT CCT GCA GTG GCC ACC TAC GTG GCA GCC TGT CAG     6962
Pro Gly Gly Leu Cys Pro Ala Val Ala Thr Tyr Val Ala Ala Cys Gln
            4900                4905                4910
```

```
GCC GCT GGG GCC CAG CTC CGC GAG TGG AGG CGG CCG GAC TTC TGT CCC        7010
Ala Ala Gly Ala Gln Leu Arg Glu Trp Arg Arg Pro Asp Phe Cys Pro
            4915                4920                4925

TTC CAG TGC CCT GCC CAC AGC CAC TAC GAG CTC TGC GGT GAC TCC TGT        7058
Phe Gln Cys Pro Ala His Ser His Tyr Glu Leu Cys Gly Asp Ser Cys
        4930                4935                4940

CCT GGG AGC TGC CCG AGC CTG TCG GCA CCC GAG GGC TGT GAG TCG GCC        7106
Pro Gly Ser Cys Pro Ser Leu Ser Ala Pro Glu Gly Cys Glu Ser Ala
4945                4950                4955                4960

TGC CGT GAA GGC TGT GTC TGC GAT GCT GGC TTC GTG CTC AGT GGT GAC        7154
Cys Arg Glu Gly Cys Val Cys Asp Ala Gly Phe Val Leu Ser Gly Asp
                4965                4970                4975

ACG TGT GTA CCT GTG GGC CAG TGT GGC TGC CTC CAC GAT GAC CGC TAC        7202
Thr Cys Val Pro Val Gly Gln Cys Gly Cys Leu His Asp Asp Arg Tyr
            4980                4985                4990

TAC CCA CTG GGC CAG ACC TTC TAC CCT GGC CCT GGG TGT GAT TCC CTT        7250
Tyr Pro Leu Gly Gln Thr Phe Tyr Pro Gly Pro Gly Cys Asp Ser Leu
        4995                5000                5005

TGC CGC TGC CGG GAG GGC GGT GAG GTG TCC TGT GAG CCC TCC AGC TGC        7298
Cys Arg Cys Arg Glu Gly Gly Glu Val Ser Cys Glu Pro Ser Ser Cys
5010                5015                5020

GGC CCG CAT GAG ACC TGC CGG CCA TCC GGT GGC AGC TTG GGC TGC GTG        7346
Gly Pro His Glu Thr Cys Arg Pro Ser Gly Gly Ser Leu Gly Cys Val
5025                5030                5035                5040

GCC GTG GGC TCT ACC ACC TGC CAG GCG TCG GGA GAT CCC CAC TAC ACC        7394
Ala Val Gly Ser Thr Thr Cys Gln Ala Ser Gly Asp Pro His Tyr Thr
                5045                5050                5055

ACC TTC GAT GGC CGC CGC TTC GAC TTC ATG GGC ACC TGC GTG TAT GTG        7442
Thr Phe Asp Gly Arg Arg Phe Asp Phe Met Gly Thr Cys Val Tyr Val
        5060                5065                5070

CTG GCT CAG ACC TGC GGC ACC CGG CCT GGC CTA CAT CGG TTT GCC GTC        7490
Leu Ala Gln Thr Cys Gly Thr Arg Pro Gly Leu His Arg Phe Ala Val
            5075                5080                5085

CTG CAG GAG AAC GTG GCC TGG GGT AAT GGG CGA GTC AGT GTG ACC AGG        7538
Leu Gln Glu Asn Val Ala Trp Gly Asn Gly Arg Val Ser Val Thr Arg
        5090                5095                5100

GTG ATC ACG GTC CAG GTG GCA AAC TTC ACC CTG CGG CTG GAG CAG AGA        7586
Val Ile Thr Val Gln Val Ala Asn Phe Thr Leu Arg Leu Glu Gln Arg
5105                5110                5115                5120

CAG TGG AAG GTC ACG GTG AAC GGT GTG GAC ATG AAG CTG CCC GTG GTG        7634
Gln Trp Lys Val Thr Val Asn Gly Val Asp Met Lys Leu Pro Val Val
                5125                5130                5135

CTG GCC AAC GGC CAG ATC CGT GCC TCC CAG CAT GGT TCA GAT GTT GTG        7682
Leu Ala Asn Gly Gln Ile Arg Ala Ser Gln His Gly Ser Asp Val Val
        5140                5145                5150

ATT GAG ACC GAC TTC GGC CTG CGT GTG GCC TAC GAC CTT GTG TAC TAT        7730
Ile Glu Thr Asp Phe Gly Leu Arg Val Ala Tyr Asp Leu Val Tyr Tyr
            5155                5160                5165

GTG CGG GTC ACC GTC CCT GGA AAC TAC TAC CAG CTG ATG TGT GGC CTG        7778
Val Arg Val Thr Val Pro Gly Asn Tyr Tyr Gln Leu Met Cys Gly Leu
        5170                5175                5180

TGT GGG AAC TAC AAC GGC GAC CCC AAG GAT GAC TTC CAG AAG CCC AAT        7826
Cys Gly Asn Tyr Asn Gly Asp Pro Lys Asp Asp Phe Gln Lys Pro Asn
5185                5190                5195                5200

GGC TCG CAG GCA GGC AAC GCC AAT GAG TTC GGC AAC TCC TGG GAG GAG        7874
Gly Ser Gln Ala Gly Asn Ala Asn Glu Phe Gly Asn Ser Trp Glu Glu
                5205                5210                5215

GTG GTG CCC GAC TCT CCC TGC CTG CCG CCG CCC ACC TGC CCG CCG GGG        7922
Val Val Pro Asp Ser Pro Cys Leu Pro Pro Pro Thr Cys Pro Pro Gly
```

```
                  5220                5225                5230
AGC GAG GGC TGT ATC CCC AGC GAG GAG TGT CCT CCC GAG CTG GAG AAG     7970
Ser Glu Gly Cys Ile Pro Ser Glu Glu Cys Pro Pro Glu Leu Glu Lys
            5235                5240                5245

AAG TAT CAG AAG GAG GAG TTC TGT GGG CTC CTC TCC AGC CCC ACA GGG     8018
Lys Tyr Gln Lys Glu Glu Phe Cys Gly Leu Leu Ser Ser Pro Thr Gly
        5250                5255                5260

CCA CTG TCC TCC TGC CAC AAG CTG GTG GAT CCC CAG GGT CCC TTG AAA     8066
Pro Leu Ser Ser Cys His Lys Leu Val Asp Pro Gln Gly Pro Leu Lys
5265                5270                5275                5280

GAT TGC ATC TTT GAT CTC TGC CTG GGT GGT GGG AAC CTG AGC ATT CTC     8114
Asp Cys Ile Phe Asp Leu Cys Leu Gly Gly Gly Asn Leu Ser Ile Leu
            5285                5290                5295

TGC AGC AAC ATC CAT GCC TAC GTG AGT GCT TGC CAG GCG GCT GGA GGC     8162
Cys Ser Asn Ile His Ala Tyr Val Ser Ala Cys Gln Ala Ala Gly Gly
        5300                5305                5310

CAC GTG GAG CCC TGG AGG AAT GAA ACT TTC TGT CCC ATG GAA TGC CCT     8210
His Val Glu Pro Trp Arg Asn Glu Thr Phe Cys Pro Met Glu Cys Pro
    5315                5320                5325

CAG AAC AGT CAC TAC GAG CTC TGT GCG GAC ACC TGC TCC CTG GGC TGC     8258
Gln Asn Ser His Tyr Glu Leu Cys Ala Asp Thr Cys Ser Leu Gly Cys
        5330                5335                5340

TCG GCT CTC AGT GCC CCT CTG CAG TGC CCA GAT GGG TGT GCT GAG GGC     8306
Ser Ala Leu Ser Ala Pro Leu Gln Cys Pro Asp Gly Cys Ala Glu Gly
5345                5350                5355                5360

TGC CAG TGT GAC TCC GGC TTC CTC TAC AAC GGC CAA GCC TGC GTG CCC     8354
Cys Gln Cys Asp Ser Gly Phe Leu Tyr Asn Gly Gln Ala Cys Val Pro
            5365                5370                5375

ATC CAG CAA TGT GGC TGC TAC CAC AAT GGT GCC TAC TAT GAG CCG GAG     8402
Ile Gln Gln Cys Gly Cys Tyr His Asn Gly Ala Tyr Tyr Glu Pro Glu
        5380                5385                5390

CAG ACA GTC CTC ATT GAC AAC TGT CGG CAG CAG TGC ACG TGC CAT GCG     8450
Gln Thr Val Leu Ile Asp Asn Cys Arg Gln Gln Cys Thr Cys His Ala
    5395                5400                5405

GGT AAA GTC GTG GTG TGC CAG GAA CAC AGC TGC AAG CCG GGG CAG GTG     8498
Gly Lys Val Val Val Cys Gln Glu His Ser Cys Lys Pro Gly Gln Val
        5410                5415                5420

TGC CAG CCC TCC GGA GGC ATC CTG AGC TGC GTC ACC AAA GAC CCG TGC     8546
Cys Gln Pro Ser Gly Gly Ile Leu Ser Cys Val Thr Lys Asp Pro Cys
5425                5430                5435                5440

CAC GGC GTG ACA TGC CGG CCA CAG GAG ACA TGC AAG GAG CAG GGT GGC     8594
His Gly Val Thr Cys Arg Pro Gln Glu Thr Cys Lys Glu Gln Gly Gly
            5445                5450                5455

CAG GGT GTG TGC CTG CCC AAC TAT GAG GCC ACG TGC TGG CTG TGG GGC     8642
Gln Gly Val Cys Leu Pro Asn Tyr Glu Ala Thr Cys Trp Leu Trp Gly
        5460                5465                5470

GAC CCA CAC TAC CAC TCC TTC GAT GGC CGG AAG TTT GAC TTC CAG GGC     8690
Asp Pro His Tyr His Ser Phe Asp Gly Arg Lys Phe Asp Phe Gln Gly
    5475                5480                5485

ACC TGT AAC TAT GTG CTG GCA ACA ACT GGC TGC CCG GGG TCA GCC ACC     8738
Thr Cys Asn Tyr Val Leu Ala Thr Thr Gly Cys Pro Gly Val Ser Thr
        5490                5495                5500

CAG GGC CTG ACA CCC TTC ACC GTC ACC ACC AAG AAC CAG AAC CGG GGC     8786
Gln Gly Leu Thr Pro Phe Thr Val Thr Thr Lys Asn Gln Asn Arg Gly
5505                5510                5515                5520

AAC CCT GCT GTA TCC TAC GTG AGA GTC GTC ACC GTG GCT GCC CTC GGC     8834
Asn Pro Ala Val Ser Tyr Val Arg Val Val Thr Val Ala Ala Leu Gly
            5525                5530                5535

ACC AAC ATC TCC ATC CAC AAG GAC GAG ATC GGC AAA GTC CGG GTG AAC     8882
```

```
                                                      -continued

Thr Asn Ile Ser Ile His Lys Asp Glu Ile Gly Lys Val Arg Val Asn
        5540                5545                5550

GGT GTG CTC ACA GCC TTG CCT GTC TCC GTG GCC GAC GGG CGG ATT TCA         8930
Gly Val Leu Thr Ala Leu Pro Val Ser Val Ala Asp Gly Arg Ile Ser
    5555                5560                5565

GTG GCC CAG GGT GCA TCG AAG GCA CTG CTG GTG GCT GAC TTT GGA CTG         8978
Val Ala Gln Gly Ala Ser Lys Ala Leu Leu Val Ala Asp Phe Gly Leu
5570                5575                5580

CAA GTC AGC TAT GAC TGG AAC TGG CGG GTA GAC GTG ACG CTC CCC AGC         9026
Gln Val Ser Tyr Asp Trp Asn Trp Arg Val Asp Val Thr Leu Pro Ser
5585                5590                5595                5600

AGC TAT CAT GGC GCA GTG TGC GGG CTC TGC GGT AAC ATG GAC CGC AAC         9074
Ser Tyr His Gly Ala Val Cys Gly Leu Cys Gly Asn Met Asp Arg Asn
            5605                5610                5615

CCC AAC AAT GAC CAG GTC TTC CCT AAT GGC ACA CTG GCT CCC TCC ATA         9122
Pro Asn Asn Asp Gln Val Phe Pro Asn Gly Thr Leu Ala Pro Ser Ile
        5620                5625                5630

CCC ATC TGG GGC GGC AGC TGG CGA GCC CCA GGC TGG GAC CCA CTG TGT         9170
Pro Ile Trp Gly Gly Ser Trp Arg Ala Pro Gly Trp Asp Pro Leu Cys
    5635                5640                5645

TGG GAC GAA TGT CGG GGG TCC TGC CCA ACG TGC CCT GAG GAC CGG TTG         9218
Trp Asp Glu Cys Arg Gly Ser Cys Pro Thr Cys Pro Glu Asp Arg Leu
    5650                5655                5660

GAG CAG TAC GAG GGC CCT GGC TTC TGC GGA CCC CTG GCC CCC GGC ACA         9266
Glu Gln Tyr Glu Gly Pro Gly Phe Cys Gly Pro Leu Ala Pro Gly Thr
5665                5670                5675                5680

GGG GGC CCT TTC ACC ACC TGC CAT GCT CAT GTG CCA CCT GAG AGC TTC         9314
Gly Gly Pro Phe Thr Thr Cys His Ala His Val Pro Pro Glu Ser Phe
            5685                5690                5695

TTC AAG GGC TGT GTT CTG GAC GTC TGC ATG GGT GGT GGG GAC CAT GAC         9362
Phe Lys Gly Cys Val Leu Asp Val Cys Met Gly Gly Gly Asp His Asp
        5700                5705                5710

ATT CTT TGC AAG GCT CTG GCT TCC TAC GTG GCC GCC TGC CAG GCC GCT         9410
Ile Leu Cys Lys Ala Leu Ala Ser Tyr Val Ala Ala Cys Gln Ala Ala
            5715                5720                5725

GGG GTT GTC ATC GAA GAC TGG CGG GCA CAG GTT GGC TGT GAG ATC ACC         9458
Gly Val Val Ile Glu Asp Trp Arg Ala Gln Val Gly Cys Glu Ile Thr
        5730                5735                5740

TGC CCA GAA AAC AGC CAC TAT GAG GTC TGT GGC CCA CCC TGC CCG GCC         9506
Cys Pro Glu Asn Ser His Tyr Glu Val Cys Gly Pro Pro Cys Pro Ala
5745                5750                5755                5760

AGC TGT CCG TCC CCT GCA CCC CTT ACG ACG CCA GCC GTA TGT GAG GGC         9554
Ser Cys Pro Ser Pro Ala Pro Leu Thr Thr Pro Ala Val Cys Glu Gly
            5765                5770                5775

CCC TGT GTG GAG GGC TGC CAG TGC GAC GCG GGT TTC GTG TTA AGT GCT         9602
Pro Cys Val Glu Gly Cys Gln Cys Asp Ala Gly Phe Val Leu Ser Ala
        5780                5785                5790

GAC CGC TGT GTT CCC CTC AAC AAC GGC TGC GGC TGC TGG GCC AAT GGC         9650
Asp Arg Cys Val Pro Leu Asn Asn Gly Cys Gly Cys Trp Ala Asn Gly
        5795                5800                5805

ACC TAC CAC GAG GCG GGC AGT GAG TTT TGG GCT GAT GGC ACC TGC TCC         9698
Thr Tyr His Glu Ala Gly Ser Glu Phe Trp Ala Asp Gly Thr Cys Ser
        5810                5815                5820

CAG TGG TGT CGC TGC GGG CCT GGG GGT GGC TCG CTG GTC TGC ACA CCT         9746
Gln Trp Cys Arg Cys Gly Pro Gly Gly Gly Ser Leu Val Cys Thr Pro
5825                5830                5835                5840

GCC AGC TGT GGG CTG GGT GAA GTG TGT GGC CTC CTG CCA TCC GGC CAG         9794
Ala Ser Cys Gly Leu Gly Glu Val Cys Gly Leu Leu Pro Ser Gly Gln
            5845                5850                5855
```

```
CAC GGC TGC CAG CCC GTC AGC ACA GCT GAG TGC CAG GCG TGG GGT GAC                     9842
His Gly Cys Gln Pro Val Ser Thr Ala Glu Cys Gln Ala Trp Gly Asp
            5860                5865                5870

CCC CAT TAC GTC ACT CTG GAT GGG CAC CGA TTC GAT TTC CAA GGC ACC                     9890
Pro His Tyr Val Thr Leu Asp Gly His Arg Phe Asp Phe Gln Gly Thr
            5875                5880                5885

TGC GAG TAC CTG CTG AGT GCA CCC TGC CAC GGA CCA CCC TTG GGG GCT                     9938
Cys Glu Tyr Leu Leu Ser Ala Pro Cys His Gly Pro Pro Leu Gly Ala
    5890                5895                5900

GAG AAC TTC ACT GTC ACT GTA GCC AAT GAG CAC CGG GGC AGC CAG GCT                     9986
Glu Asn Phe Thr Val Thr Val Ala Asn Glu His Arg Gly Ser Gln Ala
5905                5910                5915                5920

GTC AGC TAC ACC CGC AGT GTC ACC CTG CAA ATC TAC AAC CAC AGC CTG                    10034
Val Ser Tyr Thr Arg Ser Val Thr Leu Gln Ile Tyr Asn His Ser Leu
                5925                5930                5935

ACA CTG AGT GCC CGC TGG CCC CGG AAG CTA CAG GTG GAC GGC GTG TTC                    10082
Thr Leu Ser Ala Arg Trp Pro Arg Lys Leu Gln Val Asp Gly Val Phe
            5940                5945                5950

GTC ACT CTG CCC TTC CAG CTG GAC TCG CTC CTG CAC GCA CAC CTG AGC                    10130
Val Thr Leu Pro Phe Gln Leu Asp Ser Leu Leu His Ala His Leu Ser
            5955                5960                5965

GGC GCC GAC GTG GTG GTG ACC ACA ACC TCA GGG CTC TCG CTG GCT TTC                    10178
Gly Ala Asp Val Val Val Thr Thr Thr Ser Gly Leu Ser Leu Ala Phe
    5970                5975                5980

GAC GGG GAC AGC TTC GTG CGC CTG CGC GTG CCG GCG GCG TAC GCG GGC                    10226
Asp Gly Asp Ser Phe Val Arg Leu Arg Val Pro Ala Ala Tyr Ala Gly
5985                5990                5995                6000

TCT CTC TGT GGC TTA TGC GGG AAC TAC AAC CAG GAC CCC GCA GAC GAC                    10274
Ser Leu Cys Gly Leu Cys Gly Asn Tyr Asn Gln Asp Pro Ala Asp Asp
            6005                6010                6015

CTG AAG GCG GTG GGC GGG AAG CCC GCC GGA TGG CAG GTG GGC GGC GCC                    10322
Leu Lys Ala Val Gly Gly Lys Pro Ala Gly Trp Gln Val Gly Gly Ala
            6020                6025                6030

CAG GGC TGC GGG GAA TGT GTG TCC AAG CCA TGC CCG TCG CCG TGC ACC                    10370
Gln Gly Cys Gly Glu Cys Val Ser Lys Pro Cys Pro Ser Pro Cys Thr
            6035                6040                6045

CCA GAG CAG CAA GAG TCC TTC GGC GGC CCG GAC GCC TGC GGC GTG ATC                    10418
Pro Glu Gln Gln Glu Ser Phe Gly Gly Pro Asp Ala Cys Gly Val Ile
    6050                6055                6060

TCC GCC ACC GAC GGC CCG CTG GCG CCC TGC CAC GGC CTT GTG CCG CCC                    10466
Ser Ala Thr Asp Gly Pro Leu Ala Pro Cys His Gly Leu Val Pro Pro
6065                6070                6075                6080

GCG CAG TAC TTC CAG GGC TGC TTG CTG GAC GCC TGC CAA GTT CAG GGC                    10514
Ala Gln Tyr Phe Gln Gly Cys Leu Leu Asp Ala Cys Gln Val Gln Gly
            6085                6090                6095

CAT CCT GGA GGC CTC TGT CCT GCA GTG GCC ACC TAC GTG GCA GCC TGT                    10562
His Pro Gly Gly Leu Cys Pro Ala Val Ala Thr Tyr Val Ala Ala Cys
            6100                6105                6110

CAG GCC GCT GGG GCC CAG CTC CGC GAG TGG AGG CGG CCG GAC TTC TGT                    10610
Gln Ala Ala Gly Ala Gln Leu Arg Glu Trp Arg Arg Pro Asp Phe Cys
            6115                6120                6125

CCC TTC CAG TGC CCT GCC CAC AGC CAC TAC GAG CTC TGC GGT GAC TCC                    10658
Pro Phe Gln Cys Pro Ala His Ser His Tyr Glu Leu Cys Gly Asp Ser
        6130                6135                6140

TGT CCT GGG AGC TGC CCG AGC CTG TCG GCA CCC GAG GGC TGT GAG TCG                    10706
Cys Pro Gly Ser Cys Pro Ser Leu Ser Ala Pro Glu Gly Cys Glu Ser
6145                6150                6155                6160

GCC TGC CGT GAA GGC TGT GTC TGC GAT GCT GGC TTC GTG CTC AGT GGT                    10754
Ala Cys Arg Glu Gly Cys Val Cys Asp Ala Gly Phe Val Leu Ser Gly
            6165                6170                6175
```

```
GAC ACG TGT GTA CCT GTG GGC CAG TGT GGC TGC CTC CAC GAT GAC CGC      10802
Asp Thr Cys Val Pro Val Gly Gln Cys Gly Cys Leu His Asp Asp Arg
        6180                6185                6190

TAC TAC CCA CTG GGC CAG ACC TTC TAC CCT GGC CCT GGG TGT GAT TCC      10850
Tyr Tyr Pro Leu Gly Gln Thr Phe Tyr Pro Gly Pro Gly Cys Asp Ser
        6195                6200                6205

CTT TGC CGC TGC CGG GAG GGC GGT GAG GTG TCC TGT GAG CCC TCC AGC      10898
Leu Cys Arg Cys Arg Glu Gly Gly Glu Val Ser Cys Glu Pro Ser Ser
6210                6215                6220

TGC GGC CCG CAT GAG ACC TGC CGG CCA TCC GGT GGC AGC TTG GGC TGC      10946
Cys Gly Pro His Glu Thr Cys Arg Pro Ser Gly Gly Ser Leu Gly Cys
6225                6230                6235                6240

GTG GCC GTG GGC TCT ACC ACC TGC CAG GCG TCG GGA GAT CCC CAC TAC      10994
Val Ala Val Gly Ser Thr Thr Cys Gln Ala Ser Gly Asp Pro His Tyr
                6245                6250                6255

ACC ACC TTC GAT GGC CGC CGC TTC GAC TTC ATG GGC ACC TGC GTG TAT      11042
Thr Thr Phe Asp Gly Arg Arg Phe Asp Phe Met Gly Thr Cys Val Tyr
                6260                6265                6270

GTG CTG GCT CAG ACC TGC GGC ACC CGG CCT GGC CTA CAT CGG TTT GCC      11090
Val Leu Ala Gln Thr Cys Gly Thr Arg Pro Gly Leu His Arg Phe Ala
        6275                6280                6285

GTC CTG CAG GAG AAC GTG GCC TGG GGT AAT GGG CGA GTC AGT GTG ACC      11138
Val Leu Gln Glu Asn Val Ala Trp Gly Asn Gly Arg Val Ser Val Thr
        6290                6295                6300

AGG GTG ATC ACG GTC CAG GTG GCA AAC TTC ACC CTG CGG CTG GAG CAG      11186
Arg Val Ile Thr Val Gln Val Ala Asn Phe Thr Leu Arg Leu Glu Gln
6305                6310                6315                6320

AGA CAG TGG AAG GTC ACG GTG AAC GGT GTG GAC ATG AAG CTG CCC GTG      11234
Arg Gln Trp Lys Val Thr Val Asn Gly Val Asp Met Lys Leu Pro Val
                6325                6330                6335

GTG CTG GCC AAC GGC CAG ATC CGT GCC TCC CAG CAT GGT TCA GAT GTT      11282
Val Leu Ala Asn Gly Gln Ile Arg Ala Ser Gln His Gly Ser Asp Val
        6340                6345                6350

GTG ATT GAG ACC GAC TTC GGC CTG CGT GTG GCC TAC GAC CTT GTG TAC      11330
Val Ile Glu Thr Asp Phe Gly Leu Arg Val Ala Tyr Asp Leu Val Tyr
        6355                6360                6365

TAT GTG CGG GTC ACC GTC CCT GGA AAC TAC TAC CAG CTG ATG TGT GGC      11378
Tyr Val Arg Val Thr Val Pro Gly Asn Tyr Tyr Gln Leu Met Cys Gly
        6370                6375                6380

CTG TGT GGG AAC TAC AAC GGC GAC CCC AAG GAT GAC TTC CAG AAG CCC      11426
Leu Cys Gly Asn Tyr Asn Gly Asp Pro Lys Asp Asp Phe Gln Lys Pro
6385                6390                6395                6400

AAT GGC TCG CAG GCA GGC AAC GCC AAT GAG TTC GGC AAC TCC TGG GAG      11474
Asn Gly Ser Gln Ala Gly Asn Ala Asn Glu Phe Gly Asn Ser Trp Glu
                6405                6410                6415

GAG GTG GTG CCC GAC TCT CCC TGC CTG CCG CCG CCC ACC TGC CCG CCG      11522
Glu Val Val Pro Asp Ser Pro Cys Leu Pro Pro Pro Thr Cys Pro Pro
                6420                6425                6430

GGG AGC GAG GGC TGT ATC CCC AGC GAG GAG TGT CCT CCC GAG CTG GAG      11570
Gly Ser Glu Gly Cys Ile Pro Ser Glu Glu Cys Pro Pro Glu Leu Glu
        6435                6440                6445

AAG AAG TAT CAG AAG GAG GAG TTC TGT GGG CTC CTC TCC AGC CCC ACA      11618
Lys Lys Tyr Gln Lys Glu Glu Phe Cys Gly Leu Leu Ser Ser Pro Thr
        6450                6455                6460

GGG CCA CTG TCC TCC TGC CAC AAG CTG GTG GAT CCC CAG GGT CCC TTG      11666
Gly Pro Leu Ser Ser Cys His Lys Leu Val Asp Pro Gln Gly Pro Leu
6465                6470                6475                6480

AAA GAT TGC ATC TTT GAT CTC TGC CTG GGT GGT GGG AAC CTG AGC ATT      11714
Lys Asp Cys Ile Phe Asp Leu Cys Leu Gly Gly Gly Asn Leu Ser Ile
```

-continued

| | | | | |
|---|---|---|---|---|
| | 6485 | 6490 | 6495 | |
| CTC TGC AGC AAC ATC CAT GCC TAC GTG AGT GCT TGC CAG GCG GCT GGA | | | | 11762 |
| Leu Cys Ser Asn Ile His Ala Tyr Val Ser Ala Cys Gln Ala Ala Gly | | | | |
| 6500 6505 6510 | | | | |
| GGC CAC GTG GAG CCC TGG AGG AAT GAA ACT TTC TGT CCC ATG GAA TGC | | | | 11810 |
| Gly His Val Glu Pro Trp Arg Asn Glu Thr Phe Cys Pro Met Glu Cys | | | | |
| 6515 6520 6525 | | | | |
| CCT CAG AAC AGT CAC TAC GAG CTC TGT GCG GAC ACC TGC TCC CTG GGC | | | | 11858 |
| Pro Gln Asn Ser His Tyr Glu Leu Cys Ala Asp Thr Cys Ser Leu Gly | | | | |
| 6530 6535 6540 | | | | |
| TGC TCG GCT CTC AGT GCC CCT CTG CAG TGC CCA GAT GGG TGT GCT GAG | | | | 11906 |
| Cys Ser Ala Leu Ser Ala Pro Leu Gln Cys Pro Asp Gly Cys Ala Glu | | | | |
| 6545 6550 6555 6560 | | | | |
| GGC TGC CAG TGT GAC TCC GGC TTC CTC TAC AAC GGC CAA GCC TGC GTG | | | | 11954 |
| Gly Cys Gln Cys Asp Ser Gly Phe Leu Tyr Asn Gly Gln Ala Cys Val | | | | |
| 6565 6570 6575 | | | | |
| CCC ATC CAG CAA TGT GGC TGC TAC CAC AAT GGT GTC TAC TAT GAG CCG | | | | 12002 |
| Pro Ile Gln Gln Cys Gly Cys Tyr His Asn Gly Val Tyr Tyr Glu Pro | | | | |
| 6580 6585 6590 | | | | |
| GAG CAG ACA GTC CTC ATT GAC AAC TGT CGG CAG CAG TGC ACG TGC CAT | | | | 12050 |
| Glu Gln Thr Val Leu Ile Asp Asn Cys Arg Gln Gln Cys Thr Cys His | | | | |
| 6595 6600 6605 | | | | |
| GTG GGT AAA GTC GTG GTG TGC CAG GAA CAC AGC TGC AAG CCG GGG CAG | | | | 12098 |
| Val Gly Lys Val Val Val Cys Gln Glu His Ser Cys Lys Pro Gly Gln | | | | |
| 6610 6615 6620 | | | | |
| GTG TGC CAG CCC TCC GGA GGC ATC CTG AGC TGC GTC AAC AAA GAC CCG | | | | 12146 |
| Val Cys Gln Pro Ser Gly Gly Ile Leu Ser Cys Val Asn Lys Asp Pro | | | | |
| 6625 6630 6635 6640 | | | | |
| TGC CAC GGC GTG ACA TGC CGG CCA CAG GAG ACA TGC AAG GAG CAG GGT | | | | 12194 |
| Cys His Gly Val Thr Cys Arg Pro Gln Glu Thr Cys Lys Glu Gln Gly | | | | |
| 6645 6650 6655 | | | | |
| GGC CAG GGT GTG TGC CTG CCC AAC TAT GAG GCC ACG TGC TGG CTG TGG | | | | 12242 |
| Gly Gln Gly Val Cys Leu Pro Asn Tyr Glu Ala Thr Cys Trp Leu Trp | | | | |
| 6660 6665 6670 | | | | |
| GGC GAC CCA CAC TAC CAC TCC TTC GAT GGC CGG AAG TTT GAC TTC CAG | | | | 12290 |
| Gly Asp Pro His Tyr His Ser Phe Asp Gly Arg Lys Phe Asp Phe Gln | | | | |
| 6675 6680 6685 | | | | |
| GGC ACC TGT AAC TAT GTG CTG GCA ACA ACT GGC TGC CCG GGG GTC AGC | | | | 12338 |
| Gly Thr Cys Asn Tyr Val Leu Ala Thr Thr Gly Cys Pro Gly Val Ser | | | | |
| 6690 6695 6700 | | | | |
| ACC CAG GGC CTG ACA CCC TTC ACC GTC ACC ACC AAG AAC CAG AAC CGG | | | | 12386 |
| Thr Gln Gly Leu Thr Pro Phe Thr Val Thr Thr Lys Asn Gln Asn Arg | | | | |
| 6705 6710 6715 6720 | | | | |
| GGC AAC CCT GCT GTA TCC TAC GTG AGA GTC GTC ACC GTG GCT GCC CTC | | | | 12434 |
| Gly Asn Pro Ala Val Ser Tyr Val Arg Val Val Thr Val Ala Ala Leu | | | | |
| 6725 6730 6735 | | | | |
| GGC ACC AAC ATC TCC ATC CAC AAG GAC GAG ATC GGC AAA GTC CGG GTG | | | | 12482 |
| Gly Thr Asn Ile Ser Ile His Lys Asp Glu Ile Gly Lys Val Arg Val | | | | |
| 6740 6745 6750 | | | | |
| AAC GGT GTG CTC ACA GCC TTG CCT GTC TCC GTG GCC GAC GGG CGG ATT | | | | 12530 |
| Asn Gly Val Leu Thr Ala Leu Pro Val Ser Val Ala Asp Gly Arg Ile | | | | |
| 6755 6760 6765 | | | | |
| TCA GTG GCC CAG GGT GCA TCG AAG GCA CTG CTG GTG GCT GAC TTT GGA | | | | 12578 |
| Ser Val Ala Gln Gly Ala Ser Lys Ala Leu Leu Val Ala Asp Phe Gly | | | | |
| 6770 6775 6780 | | | | |
| CTG CAA GTC AGC TAT GAC TGG AAC TGG CGG GTA GAC GTG ACG CTC CCC | | | | 12626 |
| Leu Gln Val Ser Tyr Asp Trp Asn Trp Arg Val Asp Val Thr Leu Pro | | | | |
| 6785 6790 6795 6800 | | | | |
| AGC AGC TAT CAT GGC GCA GTG TGC GGG CTC TGC GGT AAC ATG GAC CGC | | | | 12674 |

```
                Ser Ser Tyr His Gly Ala Val Cys Gly Leu Cys Gly Asn Met Asp Arg
                                6805                6810                6815

AAC CCC AAC AAT GAC CAG GTC TTC CCT AAT GGC ACA CTG GCT CCC TCC        12722
Asn Pro Asn Asn Asp Gln Val Phe Pro Asn Gly Thr Leu Ala Pro Ser
            6820                6825                6830

ATA CCC ATC TGG GGC GGC AGC TGG CGA GCC CCA GGC TGG GAC CCA CTG        12770
Ile Pro Ile Trp Gly Gly Ser Trp Arg Ala Pro Gly Trp Asp Pro Leu
            6835                6840                6845

TGT TGG GAC GAA TGT CGG GGG TCC TGC CCA ACG TGC CCT GAG GAC CGG        12818
Cys Trp Asp Glu Cys Arg Gly Ser Cys Pro Thr Cys Pro Glu Asp Arg
            6850                6855                6860

TTG GAG CAG TAC GAG GGG CCT GGC TTC TGC GGA CCC CTG GCA TCT GGC        12866
Leu Glu Gln Tyr Glu Gly Pro Gly Phe Cys Gly Pro Leu Ala Ser Gly
6865                6870                6875                6880

ACA GGG GGC CCC TTC ACC ACC TGC CAT GCT CAT GTG CCA CCT GAG AGC        12914
Thr Gly Gly Pro Phe Thr Thr Cys His Ala His Val Pro Pro Glu Ser
                6885                6890                6895

TTC TTC AAG GGC TGT GTT CTG GAC GTC TGC ATG GGT GGT GGG GAC CAT        12962
Phe Phe Lys Gly Cys Val Leu Asp Val Cys Met Gly Gly Gly Asp His
            6900                6905                6910

GAC ATT CTT TGC AAG GCT CTG GCT TCC TAC GTG GCC GCC TGC CAG GCC        13010
Asp Ile Leu Cys Lys Ala Leu Ala Ser Tyr Val Ala Ala Cys Gln Ala
            6915                6920                6925

GCT GGG GTT GTC ATC GAA GAC TGG CGG GCA CAG GTT GGC TGT GAG ATC        13058
Ala Gly Val Val Ile Glu Asp Trp Arg Ala Gln Val Gly Cys Glu Ile
            6930                6935                6940

ACC TGC CCA GAA AAC AGC CAC TAT GAG GTC TGT GGC CCA CCC TGC CCG        13106
Thr Cys Pro Glu Asn Ser His Tyr Glu Val Cys Gly Pro Pro Cys Pro
6945                6950                6955                6960

GCC AGC TGT CCG TCC CCT GCA CCC CTT ACG ACG CCA GCC GTA TGT GAG        13154
Ala Ser Cys Pro Ser Pro Ala Pro Leu Thr Thr Pro Ala Val Cys Glu
                6965                6970                6975

GGC CCC TGT GTG GAG GGC TGC CAG TGC GAC GCG GGT TTC GTG TTA AGT        13202
Gly Pro Cys Val Glu Gly Cys Gln Cys Asp Ala Gly Phe Val Leu Ser
            6980                6985                6990

GCT GAC CGC TGT GTT CCC CTC AAC AAC GGC TGC GGC TGC TGG GCC AAT        13250
Ala Asp Arg Cys Val Pro Leu Asn Asn Gly Cys Gly Cys Trp Ala Asn
            6995                7000                7005

GGC ACC TAC CAC GAG GCG GGC AGT GAG TTT TGG GCT GAT GGC ACC TGC        13298
Gly Thr Tyr His Glu Ala Gly Ser Glu Phe Trp Ala Asp Gly Thr Cys
            7010                7015                7020

TCC CAG TGG TGT CGC TGC GGG CCT GGG GGT GGC TCG CTG GTC TGC ACA        13346
Ser Gln Trp Cys Arg Cys Gly Pro Gly Gly Gly Ser Leu Val Cys Thr
7025                7030                7035                7040

CCT GCC AGC TGT GGG CTG GGT GAA GTG TGT GGC CTC CTG CCA TCC GGC        13394
Pro Ala Ser Cys Gly Leu Gly Glu Val Cys Gly Leu Leu Pro Ser Gly
                7045                7050                7055

CAG CAC AGC TGC CAG CCC GTC AGC ACA GCT GAG TGC CAG GCG TGG GGT        13442
Gln His Ser Cys Gln Pro Val Ser Thr Ala Glu Cys Gln Ala Trp Gly
            7060                7065                7070

GAC CCC CAT TAC GTC ACT CTG GAT GGG CAC CGA TTC GAT TTC CAA GGC        13490
Asp Pro His Tyr Val Thr Leu Asp Gly His Arg Phe Asp Phe Gln Gly
            7075                7080                7085

ACC TGC GAG TAC CTG CTG AGT GCA CCC TGC CAC GGA CCA CCC TTG GGG        13538
Thr Cys Glu Tyr Leu Leu Ser Ala Pro Cys His Gly Pro Pro Leu Gly
            7090                7095                7100

GCT GAG AAC TTC ACT GTC ACT GTA GCC AAT GAG CAC CGG GGC AGC CAG        13586
Ala Glu Asn Phe Thr Val Thr Val Ala Asn Glu His Arg Gly Ser Gln
7105                7110                7115                7120
```

```
GCT GTC AGC TAC ACC CGC AGT GTC ACC CTG CAA ATC TAC AAC CAC AGC     13634
Ala Val Ser Tyr Thr Arg Ser Val Thr Leu Gln Ile Tyr Asn His Ser
             7125                7130                7135

CTG ACA CTG AGT GCC CGC TGG CCC CGG AAG CTA CAG GTC GAC GGC GTG     13682
Leu Thr Leu Ser Ala Arg Trp Pro Arg Lys Leu Gln Val Asp Gly Val
             7140                7145                7150

TTC GTG GCT CTG CCT TTC CAG CTG GAC TCG CTC CTG CAC GCA CAC CTG     13730
Phe Val Ala Leu Pro Phe Gln Leu Asp Ser Leu Leu His Ala His Leu
             7155                7160                7165

AGC GGC GCC GAC GTG GTG GTG ACC ACA ACC TCA GGG CTC TCG CTG GCT     13778
Ser Gly Ala Asp Val Val Val Thr Thr Thr Ser Gly Leu Ser Leu Ala
             7170                7175                7180

TTC GAT GGG GAC AGC TTC GTG CGC CTG CGC GTG CCG GCG GCG TAC GCG     13826
Phe Asp Gly Asp Ser Phe Val Arg Leu Arg Val Pro Ala Ala Tyr Ala
7185                7190                7195                7200

GCC TCT CTC TGT GGC TTA TGC GGG AAC TAC AAC CAG GAC CCC GCA GAC     13874
Ala Ser Leu Cys Gly Leu Cys Gly Asn Tyr Asn Gln Asp Pro Ala Asp
             7205                7210                7215

GAC CTG AAG GCT GTG GGC GGG AAG CCC GCT GGA TGG CAG GTG GGC GGG     13922
Asp Leu Lys Ala Val Gly Gly Lys Pro Ala Gly Trp Gln Val Gly Gly
             7220                7225                7230

GCC CAG GGC TGC GGG GAA TGT GTG TCC AAG CCA TGC CCG TCG CCG TGC     13970
Ala Gln Gly Cys Gly Glu Cys Val Ser Lys Pro Cys Pro Ser Pro Cys
             7235                7240                7245

ACC CCA GAG CAG CAG GAG TCC TTC GGC GGC CCG GAC GCC TGC GGC GTG     14018
Thr Pro Glu Gln Gln Glu Ser Phe Gly Gly Pro Asp Ala Cys Gly Val
             7250                7255                7260

ATC TCC GCC ACC GAC GGC CCG CTG GCA CCC TGC CAC GGC CTT GTG CCG     14066
Ile Ser Ala Thr Asp Gly Pro Leu Ala Pro Cys His Gly Leu Val Pro
7265                7270                7275                7280

CCC GCG CAG TAC TTC CAG GGC TGC TTG CTG GAC GCC TGC CAA GTT CAG     14114
Pro Ala Gln Tyr Phe Gln Gly Cys Leu Leu Asp Ala Cys Gln Val Gln
             7285                7290                7295

GGC CAT CCT GGA GGC CTC TGT CCT GCA GTG GCT ACC TAC GTG GCA GCC     14162
Gly His Pro Gly Gly Leu Cys Pro Ala Val Ala Thr Tyr Val Ala Ala
             7300                7305                7310

TGT CAG GCC GCT GGG GCC CAG CTC GGC GAG TGG AGG CGG CCG GAC TTC     14210
Cys Gln Ala Ala Gly Ala Gln Leu Gly Glu Trp Arg Arg Pro Asp Phe
             7315                7320                7325

TGT CCC TTG CAG TGC CCT GCC CAC AGC CAC TAT GAG CTC TGC GGT GAC     14258
Cys Pro Leu Gln Cys Pro Ala His Ser His Tyr Glu Leu Cys Gly Asp
             7330                7335                7340

TCC TGC CCT GTG AGC TGC CCG AGC CTC TCA GCA CCC GAG GGC TGT GAG     14306
Ser Cys Pro Val Ser Cys Pro Ser Leu Ser Ala Pro Glu Gly Cys Glu
7345                7350                7355                7360

TCG GCC TGC CGT GAA GGC TGT GTC TGC GAT GCT GGC TTC GTA CTC AGT     14354
Ser Ala Cys Arg Glu Gly Cys Val Cys Asp Ala Gly Phe Val Leu Ser
             7365                7370                7375

GGT GAC ACC TGC GTA CCC GTG GGC CAG TGT GGC TGC CTC CAT GAT GGC     14402
Gly Asp Thr Cys Val Pro Val Gly Gln Cys Gly Cys Leu His Asp Gly
             7380                7385                7390

CGC TAC TAC CCA CTG GGC GAG GTC TTC TAC CCG GGC CCT GAG TGT GAG     14450
Arg Tyr Tyr Pro Leu Gly Glu Val Phe Tyr Pro Gly Pro Glu Cys Glu
             7395                7400                7405

CGA CGC TGT GAG TGT GGG CCA GGT GGC CAT GTC ACC TGC CAG GAG GGC     14498
Arg Arg Cys Glu Cys Gly Pro Gly Gly His Val Thr Cys Gln Glu Gly
             7410                7415                7420

GCA GCC TGT GGG CCC CAT GAG GAG TGC CGG TTA GAG GAT GGT GTC CAG     14546
Ala Ala Cys Gly Pro His Glu Glu Cys Arg Leu Glu Asp Gly Val Gln
7425                7430                7435                7440
```

```
GCC TGT CAT GCC ACA GGC TGT GGC CGC TGC CTG GCC AAC GGG GGC ATC    14594
Ala Cys His Ala Thr Gly Cys Gly Arg Cys Leu Ala Asn Gly Gly Ile
            7445                7450                7455

CAC TAC ATC ACC CTT GAT GGC CGT GTC TAC GAC CTG CAT GGC TCC TGC    14642
His Tyr Ile Thr Leu Asp Gly Arg Val Tyr Asp Leu His Gly Ser Cys
            7460                7465                7470

TCC TAT GTC TTG GCC CAA GTC TGC CAC CCA AAG CCT GGG GAC GAG GAC    14690
Ser Tyr Val Leu Ala Gln Val Cys His Pro Lys Pro Gly Asp Glu Asp
            7475                7480                7485

TTT TCC ATC GTG CTT GAG AAG AAT GCA GCT GGA CAT CTC CAA CGC CTC    14738
Phe Ser Ile Val Leu Glu Lys Asn Ala Ala Gly His Leu Gln Arg Leu
            7490                7495                7500

CTG GTT ACT GTG GCT GGC CAG GTT GTG AGC CTA GCT CAG GGG CAG CAG    14786
Leu Val Thr Val Ala Gly Gln Val Val Ser Leu Ala Gln Gly Gln Gln
7505                7510                7515                7520

GTC ACC GTG GAC GGC GAG GCT GTG GCC CTG CCT GTG GCT GTG GGC CGC    14834
Val Thr Val Asp Gly Glu Ala Val Ala Leu Pro Val Ala Val Gly Arg
            7525                7530                7535

GTG CGG GTG ACC GCC GAG GGC CGA AAC ATG GTT CTG CAG ACG ACC AAG    14882
Val Arg Val Thr Ala Glu Gly Arg Asn Met Val Leu Gln Thr Thr Lys
            7540                7545                7550

GGG CTG CGG CTT CTC TTT GAT GGC GAT GCC CAC CTC CTC ATG TCC ATC    14930
Gly Leu Arg Leu Leu Phe Asp Gly Asp Ala His Leu Leu Met Ser Ile
            7555                7560                7565

CCC AGC CCC TTC CGT GGA CGG CTC TGT GGC CTC TGT GGG AAC TTC AAT    14978
Pro Ser Pro Phe Arg Gly Arg Leu Cys Gly Leu Cys Gly Asn Phe Asn
            7570                7575                7580

GGC AAC TGG AGT GAC GAC TTT GTC CTG CCC AAT GGC TCA GCA GCG TCC    15026
Gly Asn Trp Ser Asp Asp Phe Val Leu Pro Asn Gly Ser Ala Ala Ser
7585                7590                7595                7600

AGT GTG GAG ACC TTC GGG GCT GCA TGG CGG GTG CCC GGC TCC TCC AAG    15074
Ser Val Glu Thr Phe Gly Ala Ala Trp Arg Val Pro Gly Ser Ser Lys
            7605                7610                7615

GGC TGT GGC GAG GGC TGC GGG CCC CAA GGC TGC CCA GTG TGC TTG GCA    15122
Gly Cys Gly Glu Gly Cys Gly Pro Gln Gly Cys Pro Val Cys Leu Ala
            7620                7625                7630

GAG GAG ACT GCA CCC TAT GAG AGC AAC GAG GCC TGC GGG CAG CTC CGG    15170
Glu Glu Thr Ala Pro Tyr Glu Ser Asn Glu Ala Cys Gly Gln Leu Arg
            7635                7640                7645

AAC CCC CAG GGC CCC TTC GCG ACC TGC CAG GCG GTG CTG AGT CCC TCT    15218
Asn Pro Gln Gly Pro Phe Ala Thr Cys Gln Ala Val Leu Ser Pro Ser
            7650                7655                7660

GAG TAC TTC CGC CAA TGC GTA TAC GAC CTG TGC GCG CAA AAG GGT GAC    15266
Glu Tyr Phe Arg Gln Cys Val Tyr Asp Leu Cys Ala Gln Lys Gly Asp
7665                7670                7675                7680

AAA GCC TTC CTG TGC CGC AGC CTG GCA GCC TAC ACG GCG GCC TGT CAG    15314
Lys Ala Phe Leu Cys Arg Ser Leu Ala Ala Tyr Thr Ala Ala Cys Gln
            7685                7690                7695

GCA GCT GGC GTG GCC GTG AAG CCC TGG AGG ACA GAC AGC TTC TGC CCG    15362
Ala Ala Gly Val Ala Val Lys Pro Trp Arg Thr Asp Ser Phe Cys Pro
            7700                7705                7710

CTC CAT TGC CCC GCC CAC AGC CAC TAC TCC ATC TGC ACT CGC ACC TGC    15410
Leu His Cys Pro Ala His Ser His Tyr Ser Ile Cys Thr Arg Thr Cys
            7715                7720                7725

CAG GGA TCC TGT GCG GCT CTC TCC GGC CTC ACG GGC TGC ACC ACC CGC    15458
Gln Gly Ser Cys Ala Ala Leu Ser Gly Leu Thr Gly Cys Thr Thr Arg
            7730                7735                7740

TGT TTT GAG GGC TGT GAG TGC GAC GAC CGC TTC CTG CTT TCC CAG GGT    15506
Cys Phe Glu Gly Cys Glu Cys Asp Asp Arg Phe Leu Leu Ser Gln Gly
```

```
7745                    7750                    7755                    7760
GTC TGC ATC CCT GTC CAA GAT TGT GGC TGC ACC CAT AAT GGC CGA TAC    15554
Val Cys Ile Pro Val Gln Asp Cys Gly Cys Thr His Asn Gly Arg Tyr
                7765                    7770                    7775

TTG CCG GTA AAC TCC TCC CTG CTG ACC TCA GAC TGC AGC GAG CGC TGT    15602
Leu Pro Val Asn Ser Ser Leu Leu Thr Ser Asp Cys Ser Glu Arg Cys
                7780                    7785                    7790

TCC TGT TCC TCA AGC TCT GGC CTG ACA TGC CAG GCC GCT GGC TGC CCA    15650
Ser Cys Ser Ser Ser Ser Gly Leu Thr Cys Gln Ala Ala Gly Cys Pro
                7795                    7800                    7805

CCA GGC CGT GTA TGT GAG GTC AAG GCT GAA GCC CGG AAC TGC TGG GCC    15698
Pro Gly Arg Val Cys Glu Val Lys Ala Glu Ala Arg Asn Cys Trp Ala
                7810                    7815                    7820

ACC CGT GGT CTC TGT GTC CTG TCT GTG GGT GCC AAC CTC ACC ACC TTT    15746
Thr Arg Gly Leu Cys Val Leu Ser Val Gly Ala Asn Leu Thr Thr Phe
7825                    7830                    7835                    7840

GAT GGG GCC CGT GGT GCC ACC ACC TCT CCT GGT GTC TAT GAG CTC TCT    15794
Asp Gly Ala Arg Gly Ala Thr Thr Ser Pro Gly Val Tyr Glu Leu Ser
                7845                    7850                    7855

TCC CGC TGC CCA GGA CTA CAG AAT ACC ATC CCC TGG TAC CGT GTA GTT    15842
Ser Arg Cys Pro Gly Leu Gln Asn Thr Ile Pro Trp Tyr Arg Val Val
                7860                    7865                    7870

GCC GAA GTC CAG ATC TGC CAT GGC AAA ACG GAG GCT GTG GGC CAG GTC    15890
Ala Glu Val Gln Ile Cys His Gly Lys Thr Glu Ala Val Gly Gln Val
                7875                    7880                    7885

CAC ATC TTC TTC CAG GAT GGG ATG GTG ACG TTG ACT CCA AAC AAG GGT    15938
His Ile Phe Phe Gln Asp Gly Met Val Thr Leu Thr Pro Asn Lys Gly
                7890                    7895                    7900

GTG TGG GTG AAT GGT CTC CGA GTG GAT CTC CCA GCT GAG AAG TTA GCA    15986
Val Trp Val Asn Gly Leu Arg Val Asp Leu Pro Ala Glu Lys Leu Ala
7905                    7910                    7915                    7920

TCT GTG TCC GTG AGT CGT ACA CCT GAT GGC TCC CTG CTA GTC CGC CAG    16034
Ser Val Ser Val Ser Arg Thr Pro Asp Gly Ser Leu Leu Val Arg Gln
                7925                    7930                    7935

AAG GCA GGG GTC CAG GTG TGG CTT GGA GCC AAT GGG AAG GTG GCT GTG    16082
Lys Ala Gly Val Gln Val Trp Leu Gly Ala Asn Gly Lys Val Ala Val
                7940                    7945                    7950

ATT GTC AGC AAT GAC CAT GCT GGG AAA CTG TGT GGG GCC TGT GGA AAC    16130
Ile Val Ser Asn Asp His Ala Gly Lys Leu Cys Gly Ala Cys Gly Asn
                7955                    7960                    7965

TTT GAC GGG GAC CAG ACC AAT GAT TGG CAT GAC TCC CAG GAG AAG CCA    16178
Phe Asp Gly Asp Gln Thr Asn Asp Trp His Asp Ser Gln Glu Lys Pro
                7970                    7975                    7980

GCG ATG GAG AAA TGG AGA GCG CAG GAC TTC TCC CCA TGT TAT GGC        16223
Ala Met Glu Lys Trp Arg Ala Gln Asp Phe Ser Pro Cys Tyr Gly
7985                    7990                    7995

TGATCAGTCA TCCACCAGGA ACGAAGATTT CCTGAAGAAG ACCTGGTCCC TCTGGAGGTT  16283

GCGGTGGCTG AAGGATGCAT CATGTGCTCC TACCCTGCTC TACCGCTTTT CTGGGTCACA  16343

GAGGCCAAAT GTGAGAGCAT TGAATAAATA TCTTAAGCT                        16382

(2) INFORMATION FOR SEQ ID NO: 9:

(i) SEQUENCE CHARACTERISTICS:
        (A) LENGTH: 5405 amino acids
        (B) TYPE: amino acid
        (D) TOPOLOGY: linear (ii) MOLECULE TYPE: protein (xi) SEQUENCE DESCRIPTION: SEQ ID NO: 9:
```

-continued

```
Met Gly Ala Leu Trp Ser Trp Trp Ile Leu Trp Ala Gly Ala Thr Leu
 1               5                  10                  15

Leu Trp Gly Leu Thr Gln Glu Ala Ser Val Asp Leu Lys Asn Thr Gly
             20                  25                  30

Arg Glu Glu Phe Leu Thr Ala Phe Leu Gln Asn Tyr Gln Leu Ala Tyr
         35                  40                  45

Ser Lys Ala Tyr Pro Arg Leu Leu Ile Ser Ser Leu Ser Glu Ser Pro
     50                  55                  60

Ala Ser Val Ser Ile Leu Ser Gln Ala Asp Asn Thr Ser Lys Lys Val
 65                  70                  75                  80

Thr Val Arg Pro Gly Glu Ser Val Met Val Asn Ile Ser Ala Lys Ala
                 85                  90                  95

Glu Met Ile Gly Ser Lys Ile Phe Gln His Ala Val Val Ile His Ser
                100                 105                 110

Asp Tyr Ala Ile Ser Val Gln Ala Leu Asn Ala Lys Pro Asp Thr Ala
            115                 120                 125

Glu Leu Thr Leu Leu Arg Pro Ile Gln Ala Leu Gly Thr Glu Tyr Phe
        130                 135                 140

Val Leu Thr Pro Pro Gly Thr Ser Ala Arg Asn Val Lys Glu Phe Ala
145                 150                 155                 160

Val Val Ala Gly Ala Ala Gly Ala Ser Val Ser Val Thr Leu Lys Gly
                165                 170                 175

Ser Val Thr Phe Asn Gly Lys Phe Tyr Pro Ala Gly Asp Val Leu Arg
            180                 185                 190

Val Thr Leu Gln Pro Tyr Asn Val Ala Gln Leu Gln Ser Ser Val Asp
        195                 200                 205

Leu Ser Gly Ser Lys Val Thr Ala Ser Ser Pro Val Ala Val Leu Ser
    210                 215                 220

Gly His Ser Cys Ala Gln Lys His Thr Thr Cys Asn His Val Val Glu
225                 230                 235                 240

Gln Leu Leu Pro Thr Ser Ala Trp Gly Thr His Tyr Val Val Pro Thr
                245                 250                 255

Leu Ala Ser Gln Ser Arg Tyr Asp Leu Ala Phe Val Val Ala Ser Gln
            260                 265                 270

Ala Thr Lys Leu Thr Tyr Asn His Gly Gly Ile Thr Gly Ser Arg Gly
        275                 280                 285

Leu Gln Ala Gly Asp Val Val Glu Phe Glu Val Arg Pro Ser Trp Pro
    290                 295                 300

Leu Tyr Leu Ser Ala Asn Val Gly Ile Gln Val Leu Leu Phe Gly Thr
305                 310                 315                 320

Gly Ala Ile Arg Asn Glu Val Thr Tyr Asp Pro Tyr Leu Val Leu Ile
                325                 330                 335

Pro Asp Val Ala Ala Tyr Cys Pro Ala Tyr Val Val Lys Ser Val Pro
            340                 345                 350

Gly Cys Glu Gly Val Ala Leu Val Val Ala Gln Thr Lys Ala Ile Ser
        355                 360                 365

Gly Leu Thr Ile Asp Gly His Ala Val Gly Ala Lys Leu Thr Trp Glu
    370                 375                 380

Ala Val Pro Gly Ser Glu Phe Ser Tyr Ala Glu Val Glu Leu Gly Thr
385                 390                 395                 400

Ala Asp Met Ile His Thr Ala Glu Ala Thr Thr Asn Leu Gly Leu Leu
                405                 410                 415
```

```
Thr Phe Gly Leu Ala Lys Ala Ile Gly Tyr Ala Thr Ala Ala Asp Cys
            420                 425                 430

Gly Arg Thr Val Leu Ser Pro Val Glu Pro Ser Cys Glu Gly Met Gln
            435                 440                 445

Cys Ala Ala Gly Gln Arg Cys Gln Val Val Gly Gly Lys Ala Gly Cys
450                 455                 460

Val Ala Glu Ser Thr Ala Val Cys Arg Ala Gln Gly Asp Pro His Tyr
465                 470                 475                 480

Thr Thr Phe Asp Gly Arg Arg Tyr Asp Met Met Gly Thr Cys Ser Tyr
            485                 490                 495

Thr Met Val Glu Leu Cys Ser Glu Asp Asp Thr Leu Pro Ala Phe Ser
            500                 505                 510

Val Glu Ala Lys Asn Glu His Arg Gly Ser Arg Arg Val Ser Tyr Val
            515                 520                 525

Gly Leu Val Thr Val Arg Ala Tyr Ser His Ser Val Ser Leu Thr Arg
            530                 535                 540

Gly Glu Val Gly Phe Val Leu Val Asp Asn Gln Arg Ser Arg Leu Pro
545                 550                 555                 560

Val Ser Leu Ser Glu Gly Arg Leu Arg Val Tyr Gln Ser Gly Pro Arg
            565                 570                 575

Ala Val Val Glu Leu Val Phe Gly Leu Val Val Thr Tyr Asp Trp Asp
            580                 585                 590

Cys Gln Leu Ala Leu Ser Leu Pro Ala Arg Phe Gln Asp Gln Val Cys
            595                 600                 605

Gly Leu Cys Gly Asn Tyr Asn Gly Asp Pro Ala Asp Asp Phe Leu Thr
            610                 615                 620

Pro Asp Gly Ala Leu Ala Pro Asp Ala Val Glu Phe Ala Ser Ser Trp
625                 630                 635                 640

Lys Leu Asp Asp Gly Asp Tyr Leu Cys Glu Asp Gly Cys Gln Asn Asn
            645                 650                 655

Cys Pro Ala Cys Thr Pro Gly Gln Ala Gln His Tyr Glu Gly Asp Arg
            660                 665                 670

Leu Cys Gly Met Leu Thr Lys Leu Asp Gly Pro Phe Ala Val Cys His
            675                 680                 685

Asp Thr Leu Asp Pro Arg Pro Phe Leu Glu Gln Cys Val Tyr Asp Leu
            690                 695                 700

Cys Val Val Gly Gly Glu Arg Leu Ser Leu Cys Arg Gly Leu Ser Ala
705                 710                 715                 720

Tyr Ala Gln Ala Cys Leu Glu Leu Gly Ile Ser Val Gly Asp Trp Arg
            725                 730                 735

Ser Pro Ala Asn Cys Pro Leu Ser Cys Pro Ala Asn Ser Arg Tyr Glu
            740                 745                 750

Leu Cys Gly Pro Ala Cys Pro Thr Ser Cys Asn Gly Ala Ala Ala Pro
            755                 760                 765

Ser Asn Cys Ser Gly Arg Pro Cys Val Glu Gly Cys Val Cys Leu Pro
770                 775                 780

Gly Phe Val Ala Ser Gly Ala Cys Val Pro Ala Ser Ser Cys Gly
785                 790                 795                 800

Cys Thr Phe Gln Gly Leu Gln Leu Ala Pro Gly Gln Glu Val Trp Ala
            805                 810                 815

Asp Glu Leu Cys Gln Arg Arg Cys Thr Cys Asn Gly Ala Thr His Gln
            820                 825                 830

Val Thr Cys Arg Asp Lys Gln Ser Cys Pro Ala Gly Glu Arg Cys Ser
```

-continued

```
            835                 840                 845

Val Gln Asn Gly Leu Leu Gly Cys Tyr Pro Asp Arg Phe Gly Thr Cys
            850                 855                 860

Gln Gly Ser Gly Asp Pro His Tyr Val Ser Phe Asp Gly Arg Arg Phe
865                 870                 875                 880

Asp Phe Met Gly Thr Cys Thr Tyr Leu Leu Val Gly Ser Cys Gly Gln
                885                 890                 895

Asn Ala Ala Leu Pro Ala Phe Arg Val Leu Val Glu Asn Glu His Arg
            900                 905                 910

Gly Ser Gln Thr Val Ser Tyr Thr Arg Ala Val Arg Val Glu Ala Arg
            915                 920                 925

Gly Val Lys Val Ala Val Arg Arg Glu Tyr Pro Gly Gln Val Leu Val
            930                 935                 940

Asp Asp Val Leu Gln Tyr Leu Pro Phe Gln Ala Ala Asp Gly Gln Val
945                 950                 955                 960

Gln Val Phe Arg Gln Gly Arg Asp Ala Val Val Arg Thr Asp Phe Gly
                965                 970                 975

Leu Thr Val Thr Tyr Asp Trp Asn Ala Arg Val Thr Ala Lys Val Pro
            980                 985                 990

Ser Ser Tyr Ala Glu Ala Leu Cys Gly Leu Cys Gly Asn Phe Asn Gly
            995                 1000                1005

Asp Pro Ala Asp Asp Leu Ala Leu Arg Gly Gly Gln Ala Ala Asn
        1010                1015                1020

Ala Leu Ala Phe Gly Asn Ser Trp Gln Glu Glu Thr Arg Pro Gly Cys
1025                1030                1035                1040

Gly Ala Thr Glu Pro Gly Asp Cys Pro Lys Leu Asp Ser Leu Val Ala
                1045                1050                1055

Gln Gln Leu Gln Ser Lys Asn Glu Cys Gly Ile Leu Ala Asp Pro Lys
            1060                1065                1070

Gly Pro Phe Arg Glu Cys His Ser Lys Leu Asp Pro Gln Gly Ala Val
            1075                1080                1085

Arg Asp Cys Val Tyr Asp Arg Cys Leu Leu Pro Gly Gln Ser Gly Pro
            1090                1095                1100

Leu Cys Asp Ala Leu Ala Thr Tyr Ala Ala Ala Cys Gln Ala Ala Gly
1105                1110                1115                1120

Ala Thr Val His Pro Trp Arg Ser Glu Glu Leu Cys Pro Leu Ser Cys
                1125                1130                1135

Pro Pro His Ser His Tyr Glu Ala Cys Ser Tyr Gly Cys Pro Leu Ser
                1140                1145                1150

Cys Gly Asp Leu Pro Val Pro Gly Gly Cys Gly Ser Glu Cys His Glu
            1155                1160                1165

Gly Cys Val Cys Asp Glu Gly Phe Ala Leu Ser Gly Glu Ser Cys Leu
            1170                1175                1180

Pro Leu Ala Ser Cys Gly Cys Val His Gln Gly Thr Tyr His Pro Pro
1185                1190                1195                1200

Gly Gln Thr Phe Tyr Pro Gly Pro Gly Cys Asp Ser Leu Cys His Cys
                1205                1210                1215

Gln Glu Gly Gly Leu Val Ser Cys Glu Ser Ser Cys Gly Pro His
            1220                1225                1230

Glu Ala Cys Gln Pro Ser Gly Gly Ser Leu Gly Cys Val Ala Val Gly
            1235                1240                1245

Ser Ser Thr Cys Gln Ala Ser Gly Asp Pro His Tyr Thr Thr Phe Asp
            1250                1255                1260
```

-continued

```
Gly Arg Arg Phe Asp Phe Met Gly Thr Cys Val Tyr Val Leu Ala Gln
1265                1270                1275                1280

Thr Cys Gly Thr Arg Pro Gly Leu His Arg Phe Ala Val Leu Gln Glu
                1285                1290                1295

Asn Val Ala Trp Gly Asn Gly Arg Val Ser Val Thr Arg Val Ile Thr
            1300                1305                1310

Val Gln Val Ala Asn Phe Thr Leu Arg Leu Glu Gln Arg Gln Trp Lys
        1315                1320                1325

Val Thr Val Asn Gly Val Asp Met Lys Leu Pro Val Val Leu Ala Asn
    1330                1335                1340

Gly Gln Ile Arg Ala Ser Gln His Gly Ser Asp Val Val Ile Glu Thr
1345                1350                1355                1360

Asp Phe Gly Leu Arg Val Ala Tyr Asp Leu Val Tyr Val Arg Val
                1365                1370                1375

Thr Val Pro Gly Asn Tyr Tyr Gln Gln Met Cys Gly Leu Cys Gly Asn
            1380                1385                1390

Tyr Asn Gly Asp Pro Lys Asp Asp Phe Gln Lys Pro Asn Gly Ser Gln
        1395                1400                1405

Ala Gly Asn Ala Asn Glu Phe Gly Asn Ser Trp Glu Glu Val Val Pro
    1410                1415                1420

Asp Ser Pro Cys Leu Pro Pro Thr Pro Cys Pro Pro Gly Ser Glu Asp
1425                1430                1435                1440

Cys Ile Pro Ser His Lys Cys Pro Pro Glu Leu Glu Lys Lys Tyr Gln
                1445                1450                1455

Lys Glu Glu Phe Cys Gly Leu Leu Ser Ser Pro Thr Gly Pro Leu Ser
            1460                1465                1470

Ser Cys His Lys Leu Val Asp Pro Gln Gly Pro Leu Lys Asp Cys Ile
        1475                1480                1485

Phe Asp Leu Cys Leu Gly Gly Gly Asn Leu Ser Ile Leu Cys Ser Asn
    1490                1495                1500

Ile His Ala Tyr Val Ser Ala Cys Gln Ala Ala Gly Gly His Val Glu
1505                1510                1515                1520

Pro Trp Arg Thr Glu Thr Phe Cys Pro Met Glu Cys Pro Pro Asn Ser
                1525                1530                1535

His Tyr Glu Leu Cys Ala Asp Thr Cys Ser Leu Gly Cys Ser Ala Leu
            1540                1545                1550

Ser Ala Pro Pro Gln Cys Gln Asp Gly Cys Ala Glu Gly Cys Gln Cys
        1555                1560                1565

Asp Ser Gly Phe Leu Tyr Asn Gly Gln Ala Cys Val Pro Ile Gln Gln
    1570                1575                1580

Cys Gly Cys Tyr His Asn Gly Val Tyr Tyr Glu Pro Glu Gln Thr Val
1585                1590                1595                1600

Leu Ile Asp Asn Cys Arg Gln Gln Cys Thr Cys His Ala Gly Lys Gly
                1605                1610                1615

Met Val Cys Gln Glu His Ser Cys Lys Pro Gly Gln Val Cys Gln Pro
            1620                1625                1630

Ser Gly Gly Ile Leu Ser Cys Val Thr Lys Asp Pro Cys His Gly Val
        1635                1640                1645

Thr Cys Arg Pro Gln Glu Thr Cys Lys Glu Gln Gly Gly Gln Gly Val
    1650                1655                1660

Cys Leu Pro Asn Tyr Glu Ala Thr Cys Trp Leu Trp Gly Asp Pro His
1665                1670                1675                1680
```

-continued

```
Tyr His Ser Phe Asp Gly Arg Lys Phe Asp Phe Gln Gly Thr Cys Asn
            1685                1690                1695

Tyr Val Leu Ala Thr Thr Gly Cys Pro Gly Val Ser Thr Gln Gly Leu
            1700                1705                1710

Thr Pro Phe Thr Val Thr Thr Lys Asn Gln Asn Arg Gly Asn Pro Ala
            1715                1720                1725

Val Ser Tyr Val Arg Val Val Thr Val Ala Ala Leu Gly Thr Asn Ile
            1730                1735                1740

Ser Ile His Lys Asp Glu Ile Gly Lys Val Arg Val Asn Gly Val Leu
1745                1750                1755                1760

Thr Ala Leu Pro Val Ser Val Ala Asp Gly Arg Ile Ser Val Thr Gln
            1765                1770                1775

Gly Ala Ser Lys Ala Leu Leu Val Ala Asp Phe Gly Leu Gln Val Ser
            1780                1785                1790

Tyr Asp Trp Asn Trp Arg Val Asp Val Thr Leu Pro Ser Ser Tyr His
            1795                1800                1805

Gly Ala Val Cys Gly Leu Cys Gly Asn Met Asp Arg Asn Pro Asn Asn
            1810                1815                1820

Asp Gln Val Phe Pro Asn Gly Thr Leu Ala Pro Ser Ile Pro Ile Trp
1825                1830                1835                1840

Gly Gly Ser Trp Arg Ala Pro Gly Trp Asp Pro Leu Cys Trp Asp Glu
            1845                1850                1855

Cys Arg Gly Ser Cys Pro Thr Cys Pro Glu Asp Arg Leu Glu Gln Tyr
            1860                1865                1870

Glu Gly Pro Gly Phe Cys Gly Pro Leu Ala Pro Gly Thr Gly Gly Pro
            1875                1880                1885

Phe Thr Thr Cys His Ala His Val Pro Pro Glu Ser Phe Phe Lys Gly
            1890                1895                1900

Cys Val Leu Asp Val Cys Met Gly Gly Gly Asp Arg Asp Ile Leu Cys
1905                1910                1915                1920

Lys Ala Leu Ala Ser Tyr Val Ala Ala Cys Gln Ala Ala Gly Val Val
            1925                1930                1935

Ile Glu Asp Trp Arg Ala Gln Val Gly Cys Glu Ile Thr Cys Pro Glu
            1940                1945                1950

Asn Ser His Tyr Glu Val Cys Gly Pro Pro Cys Pro Ala Ser Cys Pro
            1955                1960                1965

Ser Pro Ala Pro Leu Thr Thr Pro Ala Val Cys Glu Gly Pro Cys Val
            1970                1975                1980

Glu Gly Cys Gln Cys Asp Ala Gly Phe Val Leu Ser Ala Asp Arg Cys
1985                1990                1995                2000

Val Pro Leu Asn Asn Gly Cys Gly Cys Trp Ala Asn Gly Thr Tyr His
            2005                2010                2015

Glu Ala Gly Ser Glu Phe Trp Ala Asp Gly Thr Cys Ser Gln Trp Cys
            2020                2025                2030

Arg Cys Gly Pro Gly Gly Ser Leu Val Cys Thr Pro Ala Ser Cys
            2035                2040                2045

Gly Leu Gly Glu Val Cys Gly Leu Leu Pro Ser Gly Gln His Gly Cys
            2050                2055                2060

Gln Pro Val Ser Thr Ala Glu Cys Gln Ala Trp Gly Asp Pro His Tyr
2065                2070                2075                2080

Val Thr Leu Asp Gly His Arg Phe Asn Phe Gln Gly Thr Cys Glu Tyr
            2085                2090                2095

Leu Leu Ser Ala Pro Cys His Gly Pro Pro Leu Gly Ala Glu Asn Phe
```

-continued

```
                2100                2105                2110
Thr Val Thr Val Ala Asn Glu His Arg Gly Ser Gln Ala Val Ser Tyr
            2115                2120                2125
Thr Arg Ser Val Thr Leu Gln Ile Tyr Asn His Ser Leu Thr Leu Ser
        2130                2135                2140
Ala Arg Trp Pro Arg Lys Leu Gln Val Asp Gly Val Phe Val Thr Leu
2145                2150                2155                2160
Pro Phe Gln Leu Asp Ser Leu Leu His Ala His Leu Ser Gly Ala Asp
            2165                2170                2175
Val Val Val Thr Thr Ser Gly Leu Ser Leu Ala Phe Asp Gly Asp
            2180                2185                2190
Ser Phe Val Arg Leu Arg Val Pro Ala Ala Tyr Ala Gly Ser Leu Cys
            2195                2200                2205
Gly Leu Cys Gly Asn Tyr Asn Gln Asp Pro Ala Asp Asp Leu Lys Ala
            2210                2215                2220
Val Gly Gly Lys Pro Ala Gly Trp Gln Val Gly Gly Ala Gln Gly Cys
2225                2230                2235                2240
Gly Glu Cys Val Ser Lys Pro Cys Pro Ser Pro Cys Thr Pro Glu Gln
            2245                2250                2255
Gln Glu Ser Phe Gly Pro Asp Ala Cys Gly Val Ile Ser Ala Thr
            2260                2265                2270
Asp Gly Pro Leu Ala Pro Cys His Gly Leu Val Pro Pro Ala Gln Tyr
            2275                2280                2285
Phe Gln Gly Cys Leu Leu Asp Ala Cys Gln Val Gln Gly His Pro Gly
            2290                2295                2300
Gly Leu Cys Pro Ala Val Ala Thr Tyr Val Ala Ala Cys Gln Ala Ala
2305                2310                2315                2320
Gly Ala Gln Leu Arg Glu Trp Arg Arg Pro Asp Phe Cys Pro Phe Gln
            2325                2330                2335
Cys Pro Ala His Ser His Tyr Glu Leu Cys Gly Asp Ser Cys Pro Gly
            2340                2345                2350
Ser Cys Pro Ser Leu Ser Ala Pro Glu Gly Cys Glu Ser Ala Cys Arg
            2355                2360                2365
Glu Gly Cys Val Cys Asp Ala Gly Phe Val Leu Ser Gly Asp Thr Cys
            2370                2375                2380
Val Pro Val Gly Gln Cys Gly Cys Leu His Asp Asp Arg Tyr Tyr Pro
2385                2390                2395                2400
Leu Gly Gln Thr Phe Tyr Pro Gly Pro Gly Cys Asp Ser Leu Cys Arg
            2405                2410                2415
Cys Arg Glu Gly Gly Glu Val Ser Cys Glu Pro Ser Ser Cys Gly Pro
            2420                2425                2430
His Glu Thr Cys Arg Pro Ser Gly Gly Ser Leu Gly Cys Val Ala Val
            2435                2440                2445
Gly Ser Thr Thr Cys Gln Ala Ser Gly Asp Pro His Tyr Thr Thr Phe
            2450                2455                2460
Asp Gly Arg Arg Phe Asp Phe Met Gly Thr Cys Val Tyr Val Leu Ala
2465                2470                2475                2480
Gln Thr Cys Gly Thr Arg Pro Gly Leu His Arg Phe Ala Val Leu Gln
            2485                2490                2495
Glu Asn Val Ala Trp Gly Asn Gly Arg Val Ser Val Thr Arg Val Ile
            2500                2505                2510
Thr Val Gln Val Ala Asn Phe Thr Leu Arg Leu Glu Gln Arg Gln Trp
            2515                2520                2525
```

-continued

```
Lys Val Thr Val Asn Gly Val Asp Met Lys Leu Pro Val Val Leu Ala
    2530                2535                2540
Asn Gly Gln Ile Arg Ala Ser Gln His Gly Ser Asp Val Val Ile Glu
2545                2550                2555                2560
Thr Asp Phe Gly Leu Arg Val Ala Tyr Asp Leu Val Tyr Tyr Val Arg
                2565                2570                2575
Val Thr Val Pro Gly Asn Tyr Tyr Gln Leu Met Cys Gly Leu Cys Gly
            2580                2585                2590
Asn Tyr Asn Gly Asp Pro Lys Asp Asp Phe Gln Lys Pro Asn Gly Ser
            2595                2600                2605
Gln Ala Gly Asn Ala Asn Glu Phe Gly Asn Ser Trp Glu Glu Val Val
        2610                2615                2620
Pro Asp Ser Pro Cys Leu Pro Pro Thr Cys Pro Pro Gly Ser Glu
2625                2630                2635                2640
Gly Cys Ile Pro Ser Glu Glu Cys Pro Glu Leu Glu Lys Lys Tyr
                2645                2650                2655
Gln Lys Glu Glu Phe Cys Gly Leu Leu Ser Ser Pro Thr Gly Pro Leu
                2660                2665                2670
Ser Ser Cys His Lys Leu Val Asp Pro Gln Gly Pro Leu Lys Asp Cys
        2675                2680                2685
Ile Phe Asp Leu Cys Leu Gly Gly Asn Leu Ser Ile Leu Cys Ser
        2690                2695                2700
Asn Ile His Ala Tyr Val Ser Ala Cys Gln Ala Ala Gly Gly His Val
2705                2710                2715                2720
Glu Pro Trp Arg Asn Glu Thr Phe Cys Pro Met Glu Cys Pro Gln Asn
                2725                2730                2735
Ser His Tyr Glu Leu Cys Ala Asp Thr Cys Ser Leu Gly Cys Ser Ala
            2740                2745                2750
Leu Ser Ala Pro Leu Gln Cys Pro Asp Gly Cys Ala Glu Gly Cys Gln
            2755                2760                2765
Cys Asp Ser Gly Phe Leu Tyr Asn Gly Gln Ala Cys Val Pro Ile Gln
2770                2775                2780
Gln Cys Gly Cys Tyr His Asn Gly Ala Tyr Tyr Glu Pro Glu Gln Thr
2785                2790                2795                2800
Val Leu Ile Asp Asn Cys Arg Gln Gln Cys Thr Cys His Ala Gly Lys
                2805                2810                2815
Val Val Val Cys Gln Glu His Ser Cys Lys Pro Gly Gln Val Cys Gln
            2820                2825                2830
Pro Ser Gly Gly Ile Leu Ser Cys Val Thr Lys Asp Pro Cys His Gly
            2835                2840                2845
Val Thr Cys Arg Pro Gln Glu Thr Cys Lys Glu Gln Gly Gly Gln Gly
        2850                2855                2860
Val Cys Leu Pro Asn Tyr Glu Ala Thr Cys Trp Leu Trp Gly Asp Pro
2865                2870                2875                2880
His Tyr His Ser Phe Asp Gly Arg Lys Phe Asp Phe Gln Gly Thr Cys
            2885                2890                2895
Asn Tyr Val Leu Ala Thr Thr Gly Cys Pro Gly Val Ser Thr Gln Gly
            2900                2905                2910
Leu Thr Pro Phe Thr Val Thr Lys Asn Gln Asn Arg Gly Asn Pro
        2915                2920                2925
Ala Val Ser Tyr Val Arg Val Val Thr Val Ala Ala Leu Gly Thr Asn
        2930                2935                2940
```

-continued

```
Ile Ser Ile His Lys Asp Glu Ile Gly Lys Val Arg Val Asn Gly Val
2945                2950                2955                2960

Leu Thr Ala Leu Pro Val Ser Val Ala Asp Gly Arg Ile Ser Val Ala
            2965                2970                2975

Gln Gly Ala Ser Lys Ala Leu Leu Val Ala Asp Phe Gly Leu Gln Val
            2980                2985                2990

Ser Tyr Asp Trp Asn Trp Arg Val Asp Val Thr Leu Pro Ser Ser Tyr
            2995                3000                3005

His Gly Ala Val Cys Gly Leu Cys Gly Asn Met Asp Arg Asn Pro Asn
3010                3015                3020

Asn Asp Gln Val Phe Pro Asn Gly Thr Leu Ala Pro Ser Ile Pro Ile
3025                3030                3035                3040

Trp Gly Gly Ser Trp Arg Ala Pro Gly Trp Asp Pro Leu Cys Trp Asp
            3045                3050                3055

Glu Cys Arg Gly Ser Cys Pro Thr Cys Pro Glu Asp Arg Leu Glu Gln
            3060                3065                3070

Tyr Glu Gly Pro Gly Phe Cys Gly Pro Leu Ala Pro Gly Thr Gly Gly
            3075                3080                3085

Pro Phe Thr Thr Cys His Ala His Val Pro Pro Glu Ser Phe Phe Lys
            3090                3095                3100

Gly Cys Val Leu Asp Val Cys Met Gly Gly Gly Asp His Asp Ile Leu
3105                3110                3115                3120

Cys Lys Ala Leu Ala Ser Tyr Val Ala Ala Cys Gln Ala Ala Gly Val
            3125                3130                3135

Val Ile Glu Asp Trp Arg Ala Gln Val Gly Cys Glu Ile Thr Cys Pro
            3140                3145                3150

Glu Asn Ser His Tyr Glu Val Cys Gly Pro Pro Cys Pro Ala Ser Cys
            3155                3160                3165

Pro Ser Pro Ala Pro Leu Thr Thr Pro Ala Val Cys Glu Gly Pro Cys
            3170                3175                3180

Val Glu Gly Cys Gln Cys Asp Ala Gly Phe Val Leu Ser Ala Asp Arg
3185                3190                3195                3200

Cys Val Pro Leu Asn Asn Gly Cys Gly Cys Trp Ala Asn Gly Thr Tyr
            3205                3210                3215

His Glu Ala Gly Ser Glu Phe Trp Ala Asp Gly Thr Cys Ser Gln Trp
            3220                3225                3230

Cys Arg Cys Gly Pro Gly Gly Gly Ser Leu Val Cys Thr Pro Ala Ser
            3235                3240                3245

Cys Gly Leu Gly Glu Val Cys Gly Leu Leu Pro Ser Gly Gln His Gly
            3250                3255                3260

Cys Gln Pro Val Ser Thr Ala Glu Cys Gln Ala Trp Gly Asp Pro His
3265                3270                3275                3280

Tyr Val Thr Leu Asp Gly His Arg Phe Asp Phe Gln Gly Thr Cys Glu
            3285                3290                3295

Tyr Leu Leu Ser Ala Pro Cys His Gly Pro Pro Leu Gly Ala Glu Asn
            3300                3305                3310

Phe Thr Val Thr Val Ala Asn Glu His Arg Gly Ser Gln Ala Val Ser
        3315                3320                3325

Tyr Thr Arg Ser Val Thr Leu Gln Ile Tyr Asn His Ser Leu Thr Leu
        3330                3335                3340

Ser Ala Arg Trp Pro Arg Lys Leu Gln Val Asp Gly Val Phe Val Thr
3345                3350                3355                3360

Leu Pro Phe Gln Leu Asp Ser Leu Leu His Ala His Leu Ser Gly Ala
```

-continued

```
              3365                3370                3375
Asp Val Val Thr Thr Thr Ser Gly Leu Ser Leu Ala Phe Asp Gly
              3380                3385                3390
Asp Ser Phe Val Arg Leu Arg Val Pro Ala Ala Tyr Ala Gly Ser Leu
      3395                3400                3405
Cys Gly Leu Cys Gly Asn Tyr Asn Gln Asp Pro Ala Asp Asp Leu Lys
      3410                3415                3420
Ala Val Gly Gly Lys Pro Ala Gly Trp Gln Val Gly Ala Gln Gly
3425              3430                3435                3440
Cys Gly Glu Cys Val Ser Lys Pro Cys Pro Ser Cys Thr Pro Glu
              3445                3450                3455
Gln Gln Glu Ser Phe Gly Gly Pro Asp Ala Cys Gly Val Ile Ser Ala
      3460                3465                3470
Thr Asp Gly Pro Leu Ala Pro Cys His Gly Leu Val Pro Pro Ala Gln
      3475                3480                3485
Tyr Phe Gln Gly Cys Leu Leu Asp Ala Cys Gln Val Gln Gly His Pro
      3490                3495                3500
Gly Gly Leu Cys Pro Ala Val Ala Thr Tyr Val Ala Ala Cys Gln Ala
3505              3510                3515                3520
Ala Gly Ala Gln Leu Arg Glu Trp Arg Arg Pro Asp Phe Cys Pro Phe
              3525                3530                3535
Gln Cys Pro Ala His Ser His Tyr Glu Leu Cys Gly Asp Ser Cys Pro
              3540                3545                3550
Gly Ser Cys Pro Ser Leu Ser Ala Pro Glu Gly Cys Glu Ser Ala Cys
              3555                3560                3565
Arg Glu Gly Cys Val Cys Asp Ala Gly Phe Val Leu Ser Gly Asp Thr
      3570                3575                3580
Cys Val Pro Val Gly Gln Cys Gly Cys Leu His Asp Asp Arg Tyr Tyr
3585              3590                3595                3600
Pro Leu Gly Gln Thr Phe Tyr Pro Gly Pro Gly Cys Asp Ser Leu Cys
              3605                3610                3615
Arg Cys Arg Glu Gly Gly Glu Val Ser Cys Glu Pro Ser Ser Cys Gly
              3620                3625                3630
Pro His Glu Thr Cys Arg Pro Ser Gly Gly Ser Leu Gly Cys Val Ala
              3635                3640                3645
Val Gly Ser Thr Thr Cys Gln Ala Ser Gly Asp Pro His Tyr Thr Thr
3650              3655                3660
Phe Asp Gly Arg Arg Phe Asp Phe Met Gly Thr Cys Val Tyr Val Leu
3665              3670                3675                3680
Ala Gln Thr Cys Gly Thr Arg Pro Gly Leu His Arg Phe Ala Val Leu
              3685                3690                3695
Gln Glu Asn Val Ala Trp Gly Asn Gly Arg Val Ser Val Thr Arg Val
              3700                3705                3710
Ile Thr Val Gln Val Ala Asn Phe Thr Leu Arg Leu Glu Gln Arg Gln
      3715                3720                3725
Trp Lys Val Thr Val Asn Gly Val Asp Met Lys Leu Pro Val Val Leu
      3730                3735                3740
Ala Asn Gly Gln Ile Arg Ala Ser Gln His Gly Ser Asp Val Val Ile
3745              3750                3755                3760
Glu Thr Asp Phe Gly Leu Arg Val Ala Tyr Asp Leu Val Tyr Tyr Val
              3765                3770                3775
Arg Val Thr Val Pro Gly Asn Tyr Tyr Gln Leu Met Cys Gly Leu Cys
              3780                3785                3790
```

-continued

```
Gly Asn Tyr Asn Gly Asp Pro Lys Asp Asp Phe Gln Lys Pro Asn Gly
        3795                3800                3805

Ser Gln Ala Gly Asn Ala Asn Glu Phe Gly Asn Ser Trp Glu Glu Val
        3810                3815                3820

Val Pro Asp Ser Pro Cys Leu Pro Pro Thr Cys Pro Pro Gly Ser
3825                3830                3835                3840

Glu Gly Cys Ile Pro Ser Glu Glu Cys Pro Glu Leu Glu Lys Lys
                3845                3850                3855

Tyr Gln Lys Glu Glu Phe Cys Gly Leu Leu Ser Ser Pro Thr Gly Pro
        3860                3865                3870

Leu Ser Ser Cys His Lys Leu Val Asp Pro Gln Gly Pro Leu Lys Asp
        3875                3880                3885

Cys Ile Phe Asp Leu Cys Leu Gly Gly Gly Asn Leu Ser Ile Leu Cys
        3890                3895                3900

Ser Asn Ile His Ala Tyr Val Ser Ala Cys Gln Ala Gly Gly His
3905                3910                3915                3920

Val Glu Pro Trp Arg Asn Glu Thr Phe Cys Pro Met Glu Cys Pro Gln
        3925                3930                3935

Asn Ser His Tyr Glu Leu Cys Ala Asp Thr Cys Ser Leu Gly Cys Ser
        3940                3945                3950

Ala Leu Ser Ala Pro Leu Gln Cys Pro Asp Gly Cys Ala Glu Gly Cys
        3955                3960                3965

Gln Cys Asp Ser Gly Phe Leu Tyr Asn Gly Gln Ala Cys Val Pro Ile
        3970                3975                3980

Gln Gln Cys Gly Cys Tyr His Asn Gly Val Tyr Tyr Glu Pro Glu Gln
3985                3990                3995                4000

Thr Val Leu Ile Asp Asn Cys Arg Gln Gln Cys Thr Cys His Val Gly
                4005                4010                4015

Lys Val Val Cys Gln Glu His Ser Cys Lys Pro Gly Gln Val Cys
                4020                4025                4030

Gln Pro Ser Gly Gly Ile Leu Ser Cys Val Asn Lys Asp Pro Cys His
        4035                4040                4045

Gly Val Thr Cys Arg Pro Gln Glu Thr Cys Lys Glu Gln Gly Gly Gln
        4050                4055                4060

Gly Val Cys Leu Pro Asn Tyr Glu Ala Thr Cys Trp Leu Trp Gly Asp
4065                4070                4075                4080

Pro His Tyr His Ser Phe Asp Gly Arg Lys Phe Asp Phe Gln Gly Thr
                4085                4090                4095

Cys Asn Tyr Val Leu Ala Thr Thr Gly Cys Pro Gly Val Ser Thr Gln
        4100                4105                4110

Gly Leu Thr Pro Phe Thr Val Thr Thr Lys Asn Gln Asn Arg Gly Asn
        4115                4120                4125

Pro Ala Val Ser Tyr Val Arg Val Val Thr Val Ala Ala Leu Gly Thr
        4130                4135                4140

Asn Ile Ser Ile His Lys Asp Glu Ile Gly Lys Val Arg Val Asn Gly
4145                4150                4155                4160

Val Leu Thr Ala Leu Pro Val Ser Val Ala Asp Gly Arg Ile Ser Val
        4165                4170                4175

Ala Gln Gly Ala Ser Lys Ala Leu Leu Val Ala Asp Phe Gly Leu Gln
        4180                4185                4190

Val Ser Tyr Asp Trp Asn Trp Arg Val Asp Val Thr Leu Pro Ser Ser
        4195                4200                4205
```

-continued

```
Tyr His Gly Ala Val Cys Gly Leu Cys Gly Asn Met Asp Arg Asn Pro
    4210                4215                4220
Asn Asn Asp Gln Val Phe Pro Asn Gly Thr Leu Ala Pro Ser Ile Pro
4225                4230                4235                4240
Ile Trp Gly Gly Ser Trp Arg Ala Pro Gly Trp Asp Pro Leu Cys Trp
                4245                4250                4255
Asp Glu Cys Arg Gly Ser Cys Pro Thr Cys Pro Glu Asp Arg Leu Glu
            4260                4265                4270
Gln Tyr Glu Gly Pro Gly Phe Cys Gly Pro Leu Ala Ser Gly Thr Gly
        4275                4280                4285
Gly Pro Phe Thr Thr Cys His Ala His Val Pro Pro Glu Ser Phe Phe
    4290                4295                4300
Lys Gly Cys Val Leu Asp Val Cys Met Gly Gly Asp His Asp Ile
4305                4310                4315                4320
Leu Cys Lys Ala Leu Ala Ser Tyr Val Ala Ala Cys Gln Ala Ala Gly
                4325                4330                4335
Val Val Ile Glu Asp Trp Arg Ala Gln Val Gly Cys Glu Ile Thr Cys
            4340                4345                4350
Pro Glu Asn Ser His Tyr Glu Val Cys Gly Pro Pro Cys Pro Ala Ser
        4355                4360                4365
Cys Pro Ser Pro Ala Pro Leu Thr Thr Pro Ala Val Cys Glu Gly Pro
    4370                4375                4380
Cys Val Glu Gly Cys Gln Cys Asp Ala Gly Phe Val Leu Ser Ala Asp
4385                4390                4395                4400
Arg Cys Val Pro Leu Asn Asn Gly Cys Gly Cys Trp Ala Asn Gly Thr
                4405                4410                4415
Tyr His Glu Ala Gly Ser Glu Phe Trp Ala Asp Gly Thr Cys Ser Gln
            4420                4425                4430
Trp Cys Arg Cys Gly Pro Gly Gly Ser Leu Val Cys Thr Pro Ala
        4435                4440                4445
Ser Cys Gly Leu Gly Glu Val Cys Gly Leu Leu Pro Ser Gly Gln His
    4450                4455                4460
Ser Cys Gln Pro Val Ser Thr Ala Glu Cys Gln Ala Trp Gly Asp Pro
4465                4470                4475                4480
His Tyr Val Thr Leu Asp Gly His Arg Phe Asp Phe Gln Gly Thr Cys
                4485                4490                4495
Glu Tyr Leu Leu Ser Ala Pro Cys His Gly Pro Pro Leu Gly Ala Glu
            4500                4505                4510
Asn Phe Thr Val Thr Val Ala Asn Glu His Arg Gly Ser Gln Ala Val
        4515                4520                4525
Ser Tyr Thr Arg Ser Val Thr Leu Gln Ile Tyr Asn His Ser Leu Thr
    4530                4535                4540
Leu Ser Ala Arg Trp Pro Arg Lys Leu Gln Val Asp Gly Val Phe Val
4545                4550                4555                4560
Ala Leu Pro Phe Gln Leu Asp Ser Leu Leu His Ala His Leu Ser Gly
                4565                4570                4575
Ala Asp Val Val Val Thr Thr Thr Ser Gly Leu Ser Leu Ala Phe Asp
            4580                4585                4590
Gly Asp Ser Phe Val Arg Leu Arg Val Pro Ala Ala Tyr Ala Ala Ser
        4595                4600                4605
Leu Cys Gly Leu Cys Gly Asn Tyr Asn Gln Asp Pro Ala Asp Asp Leu
    4610                4615                4620
Lys Ala Val Gly Gly Lys Pro Ala Gly Trp Gln Val Gly Gly Ala Gln
```

```
4625                4630                4635                4640
Gly Cys Gly Glu Cys Val Ser Lys Pro Cys Pro Ser Pro Cys Thr Pro
                4645                4650                4655
Glu Gln Gln Glu Ser Phe Gly Gly Pro Asp Ala Cys Gly Val Ile Ser
                4660                4665                4670
Ala Thr Asp Gly Pro Leu Ala Pro Cys His Gly Leu Val Pro Pro Ala
            4675                4680                4685
Gln Tyr Phe Gln Gly Cys Leu Leu Asp Ala Cys Gln Val Gln Gly His
            4690                4695                4700
Pro Gly Gly Leu Cys Pro Ala Val Ala Thr Tyr Val Ala Ala Cys Gln
4705                4710                4715                4720
Ala Ala Gly Ala Gln Leu Gly Glu Trp Arg Arg Pro Asp Phe Cys Pro
                4725                4730                4735
Leu Gln Cys Pro Ala His Ser His Tyr Glu Leu Cys Gly Asp Ser Cys
                4740                4745                4750
Pro Val Ser Cys Pro Ser Leu Ser Ala Pro Glu Gly Cys Glu Ser Ala
                4755                4760                4765
Cys Arg Glu Gly Cys Val Cys Asp Ala Gly Phe Val Leu Ser Gly Asp
            4770                4775                4780
Thr Cys Val Pro Val Gly Gln Cys Gly Cys Leu His Asp Gly Arg Tyr
4785                4790                4795                4800
Tyr Pro Leu Gly Glu Val Phe Tyr Pro Gly Pro Glu Cys Glu Arg Arg
                4805                4810                4815
Cys Glu Cys Gly Pro Gly His Val Thr Cys Gln Glu Gly Ala Ala
                4820                4825                4830
Cys Gly Pro His Glu Glu Cys Arg Leu Glu Asp Gly Val Gln Ala Cys
            4835                4840                4845
His Ala Thr Gly Cys Gly Arg Cys Leu Ala Asn Gly Gly Ile His Tyr
            4850                4855                4860
Ile Thr Leu Asp Gly Arg Val Tyr Asp Leu His Gly Ser Cys Ser Tyr
4865                4870                4875                4880
Val Leu Ala Gln Val Cys His Pro Lys Pro Gly Asp Glu Asp Phe Ser
                4885                4890                4895
Ile Val Leu Glu Lys Asn Ala Ala Gly His Leu Gln Arg Leu Leu Val
                4900                4905                4910
Thr Val Ala Gly Gln Val Val Ser Leu Ala Gln Gly Gln Gln Val Thr
            4915                4920                4925
Val Asp Gly Glu Ala Val Ala Leu Pro Val Ala Val Gly Arg Val Arg
        4930                4935                4940
Val Thr Ala Glu Gly Arg Asn Met Val Leu Gln Thr Thr Lys Gly Leu
4945                4950                4955                4960
Arg Leu Leu Phe Asp Gly Asp Ala His Leu Leu Met Ser Ile Pro Ser
                4965                4970                4975
Pro Phe Arg Gly Arg Leu Cys Gly Leu Cys Gly Asn Phe Asn Gly Asn
            4980                4985                4990
Trp Ser Asp Asp Phe Val Leu Pro Asn Gly Ser Ala Ala Ser Ser Val
            4995                5000                5005
Glu Thr Phe Gly Ala Ala Trp Arg Val Pro Gly Ser Ser Lys Gly Cys
        5010                5015                5020
Gly Glu Gly Cys Gly Pro Gln Gly Cys Pro Val Cys Leu Ala Glu Glu
5025                5030                5035                5040
Thr Ala Pro Tyr Glu Ser Asn Glu Ala Cys Gly Gln Leu Arg Asn Pro
                5045                5050                5055
```

-continued

```
Gln Gly Pro Phe Ala Thr Cys Gln Ala Val Leu Ser Pro Ser Glu Tyr
        5060                5065                5070

Phe Arg Gln Cys Val Tyr Asp Leu Cys Ala Gln Lys Gly Asp Lys Ala
        5075                5080                5085

Phe Leu Cys Arg Ser Leu Ala Ala Tyr Thr Ala Ala Cys Gln Ala Ala
        5090                5095                5100

Gly Val Ala Val Lys Pro Trp Arg Thr Asp Ser Phe Cys Pro Leu His
5105                5110                5115                5120

Cys Pro Ala His Ser His Tyr Ser Ile Cys Thr Arg Thr Cys Gln Gly
                5125                5130                5135

Ser Cys Ala Ala Leu Ser Gly Leu Thr Gly Cys Thr Thr Arg Cys Phe
        5140                5145                5150

Glu Gly Cys Glu Cys Asp Asp Arg Phe Leu Leu Ser Gln Gly Val Cys
        5155                5160                5165

Ile Pro Val Gln Asp Cys Gly Cys Thr His Asn Gly Arg Tyr Leu Pro
        5170                5175                5180

Val Asn Ser Ser Leu Leu Thr Ser Asp Cys Ser Glu Arg Cys Ser Cys
5185                5190                5195                5200

Ser Ser Ser Ser Gly Leu Thr Cys Gln Ala Ala Gly Cys Pro Pro Gly
        5205                5210                5215

Arg Val Cys Glu Val Lys Ala Glu Ala Arg Asn Cys Trp Ala Thr Arg
        5220                5225                5230

Gly Leu Cys Val Leu Ser Val Gly Ala Asn Leu Thr Thr Phe Asp Gly
        5235                5240                5245

Ala Arg Gly Ala Thr Thr Ser Pro Gly Val Tyr Glu Leu Ser Ser Arg
        5250                5255                5260

Cys Pro Gly Leu Gln Asn Thr Ile Pro Trp Tyr Arg Val Val Ala Glu
5265                5270                5275                5280

Val Gln Ile Cys His Gly Lys Thr Glu Ala Val Gly Gln Val His Ile
                5285                5290                5295

Phe Phe Gln Asp Gly Met Val Thr Leu Thr Pro Asn Lys Gly Val Trp
        5300                5305                5310

Val Asn Gly Leu Arg Val Asp Leu Pro Ala Glu Lys Leu Ala Ser Val
        5315                5320                5325

Ser Val Ser Arg Thr Pro Asp Gly Ser Leu Leu Val Arg Gln Lys Ala
        5330                5335                5340

Gly Val Gln Val Trp Leu Gly Ala Asn Gly Lys Val Ala Val Ile Val
5345                5350                5355                5360

Ser Asn Asp His Ala Gly Lys Leu Cys Gly Ala Cys Gly Asn Phe Asp
                5365                5370                5375

Gly Asp Gln Thr Asn Asp Trp His Asp Ser Gln Glu Lys Pro Ala Met
        5380                5385                5390

Glu Lys Trp Arg Ala Gln Asp Phe Ser Pro Cys Tyr Gly
        5395                5400                5405
```

(2) INFORMATION FOR SEQ ID NO: 10:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer DNA"

(xi) SEQUENCE DESCRIPTION: SEQ ID NO: 10:

GCTGATAGTT CTGCAGGAAG GCTGTGAGGA ATTCCTCTCT GCCAGTGTT       49

(2) INFORMATION FOR SEQ ID NO: 11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 11:

GCTCCAGCCC AGAGTATCCA CCAGCTCCAT AGG       33

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 12:

CTAGTTAGTT AGTTAGGGTA CCGC       24

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 13:

GGCCGCGGTA CCCTAACTAA CTAA       24

(2) INFORMATION FOR SEQ ID NO: 14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 14:

GCCTGCGTGC CCATCCAG       18

(2) INFORMATION FOR SEQ ID NO: 15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 15:

CTCATAGTTG GGCAGCGAC                                          19

(2) INFORMATION FOR SEQ ID NO: 16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 16:

TGTTGGGACG AATGTCGG                                           18

(2) INFORMATION FOR SEQ ID NO: 17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 17:

TCACAGCCAA CCTGTGCC                                           18

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 18:

AGCTTCTGCA GCCATGGG                                           18

(2) INFORMATION FOR SEQ ID NO: 19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 19:

AGACGTCGGT ACCCTTAA                                           18

(2) INFORMATION FOR SEQ ID NO: 20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "oligonucleotide"

(xi) SEQUENCE DESCRIPTION: SEQ ID NO: 20:

AGCTTCTGCA GCCATCGGG                                                19

(2) INFORMATION FOR SEQ ID NO: 21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 21:

AGACGTCGGT ACCCC                                                    15

(2) INFORMATION FOR SEQ ID NO: 22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 22:

AGCTTCTGCA GCCATGGGA                                                19

(2) INFORMATION FOR SEQ ID NO: 23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 23:

AGACGTCGGT ACCCTCTTAA                                               20

(2) INFORMATION FOR SEQ ID NO: 24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 24:

ACCACTCCTT CGATGGCC                                                 18

(2) INFORMATION FOR SEQ ID NO: 25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear

```
        (ii) MOLECULE TYPE: other nucleic acid
             (A) DESCRIPTION: /desc = "primer"

(xi) SEQUENCE DESCRIPTION: SEQ ID NO: 25:

ACCTGTAACT ATGTGCTGGC                                                   20

(2) INFORMATION FOR SEQ ID NO: 26:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO: 26:

TGGTGGTGAC GGTGAAGGG                                                    19

(2) INFORMATION FOR SEQ ID NO: 27:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO: 27:

ACAGCAGGGT TGCCCCGG                                                     18

(2) INFORMATION FOR SEQ ID NO: 28:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO: 28:

TGGTGCCGAG GGCAGCCACG                                                   20

(2) INFORMATION FOR SEQ ID NO: 29:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO: 29:

TGGGTCACTG AAATCCG
```

GENE ENCODING IGG FC REGION-BINDING PROTEIN

SPECIFICATION

1. Technical Field

This invention relates to a gene encoding an IgG Fc portion-binding protein [hereinafter referred to as FcγBP (Fcγ Binding Protein) or IgG Fc BP], which is a protein specifically binding to the Fc portion of immunoglobulin G (IgG), a recombinant vector containing this gene, host cells transformed by this recombinant vector, a process for producing a recombinant protein which is obtained by incubating these host cells and a protein having a recombinant IgG Fc portion-binding activity which is obtained by the above-mentioned process.

2. Background Art

As one of immunocompetent cells, a macrophage incorporates a foreign invader or a complex thereof with immunoglobulin G (IgG) into the cell via phagocytosis and then digests the same. It is also capable of exerting an antigen presentation effect so as to induce the production of an antibody by lymphocytes. The main entry of this phagocytosis is an Fc receptor [FcγR (Fcγ receptor)] of IgG located on the surface of the macrophage cell. The inherent function of this Fcγ receptor, which is a receptor participating in the binding of the Fc portion of IgG, is the elimination of a pathogen or an antigen-IgG immune complex coated with IgG (opposition).

It has been known that Fcγ receptors may be roughly classified into three types including RI, RII and RIII [J. V. Ravetch and J.-P. Kinet, Annu. Rev. Immunol. (1991), 9:457–492]. The cDNA of each of these receptors has been successfully cloned. From 1990 to 1991, furthermore, several groups of workers found out proteins which were associated with these Fcγ receptors and required for the initiation of the incorporation of the binding matters by Fcγ receptors, thus providing a clue to clarify the switch mechanism [L. L. Lanier, G. Yu and J. H. Phillips, Nature (1989), 342:803–805; T. Kurosaki and J. V. Ravetch, Nature (1989), 342:805–807; D. G. Orioff, C. Ra, S. J. Frank, R. D. Klausner and J.-P. Kinet, Nature (1989), 347:189–191; P. Anderson, M. Caligiuri, C. O'Brien, T. Manley, J. Ritz and S. F. Schlossman. Prc. Natl. Acad. Sci. USA (1990), 87:2274–2278; T. Kurosaki, I. Gander and J. V. Ravetch, Proc. Natl. Acad. Sci. USA (1991), 88:3837–3841; L. Azzoni, M. Kamoun. T. W. Salcedo, P. Kanakaraj and B. Perussia, J. Exp. Med. (1992), 176:1745–1750; A. T. Ting, L. M. Karnitz, R. A. Schoon, R. T. Abraham and P. J. Leibson, J. Exp. Med. (1992), 176:1751–1755].

On the other hand, Kobayashi et al., reported a protein FcγBP, which could bind specifically to the Fc portion of IgG and was different from the conventionally known Fcγ receptors, occurring in human small intestinal and colonic epithelial cells, in particular, goblet cells. The binding of this protein specific to the IgG Fc portion was confirmed by using horse radish peroxidase-labeled matters. Namely, FcγBP bound not to IgGFab, IgA or IgM but exclusively to the Fc portion of IgG. Also, FcγBP underwent no cross reaction with antibodies of Fcγ receptors I, II and III [K. Kobayashi, M. J. Blaser and W. R. Brown, J. immunol. (1989), 143:2567–2574].

Further, they partially purified FcγBP from human colonic epithelial cells and constructed mouse monoclonal antibodies with the use of this protein as an antigen. Thus it was confirmed that FcγBP bound not only to these antibodies but also to mouse IgG [K. Kobayashi, Y. Hamada, M. J. Blaser and W. R. Brown, J. Immunol. (1991), 146:68–74].

The partially purified FcγBP was SDS (sodium dodecyl sulfate)-electrophoresed and then subjected to Western blotting with the use of the monoclonal antibodies. As a result, it was found out that FcγBP formed an associate of 200 kDa or above containing a protein of 78 kDa [K. Kobayashi, Y. Hamada, M. J. Blaser and W. R. Brown, J. Immunol. (1991), 146:68–74].

The above-mentioned FcγBP is identical with the Fcγ receptors in the point of being capable of binding to the Fc portion of IgG. However, the stability and structure of FcγBP as a protein and its role in vivo still remained unknown. It is, therefore, highly interesting to analyze FcγBP so as to clarify its structure and function.

As will be described hereinafter, it is assumed that FcγBP is secreted onto mucosae together with mucus and traps pathogens or viruses invading the body into the mucus to thereby facilitate the excretion of these invaders, thus participating in the mechanism of protection against infection. An autoantibody produced in excess in a mucosa suffering from inflammation activates the complement system or causes cytotoxicity by macrophages, etc., thus worsening the inflammation. It is assumed that FcγBP blocks the Fc portion of such an autoantibody to thereby inhibit the progression of the inflammation. Because of having these functions, FcγBP might be applicable to drugs, for example, agents for protecting infection, antiinflammatory (antiphlogistic) agents or diagnostic drugs for autoimmune diseases such as ulcerative colitis and Crohn's disease, etc.

To employ FcγBP for these medicinal purposes, it is required to obtain FcγBP in a large amount and in a uniform state. However, FcγBP in a uniform state can be hardly obtained in a large amount by the method wherein FcγBP is isolated from an animal tissue per se or a culture supernatant of FcγBP-producing cells. It is, therefore, required to produce FcγBP in a large amount by using gene recombination techniques.

The present inventors successfully identified the base sequence of a gene encoding FcγBP by cloning the cDNA of FcγBP with the use of monoclonal antibodies against FcγBP.

This cDNA was inserted into an appropriate vector and host cells were transformed by the expression vector thus obtained. Then the obtained transformant was incubated and the target protein thus produced was separated and purified. As a result, it was found out that the protein thus produced had a characteristic of binding specifically to human IgG. Thus, the present inventors have clarified that FcγBP can be produced in a large amount and in a uniform state.

DISCLOSURE OF THE INVENTION

Accordingly, the present invention provides a gene encoding FcγBP.

The present invention further provides a recombinant vector containing a gene encoding FcγBP.

The present invention furthermore provides procaryotic or eucaryotic host cells transformed by a recombinant vector containing a gene encoding FcγBP.

The present invention furthermore provides a process for producing FcγBP which comprises incubating host cells transformed by a recombinant vector containing a gene encoding FcγBP and separating and purifying the protein thus produced.

The present invention furthermore provides a protein showing an IgG Fc region-binding activity which is produced by the above-mentioned process.

The present invention furthermore provides a method for using a gene encoding FcγBP or a part of the same as a probe in Northern blotting or in situ hybridization for the identification of the tissue synthesizing FcγBP mRNA.

BRIEF DESCRIPTION OF THE DRAWINGS

FIG. 10 shows a comparison between the base sequences of exon/intron boundary region of FcγBP. The boxed capital letters show exons, while the small letters show introns. The underlined parts show highly conserved sequences. R: purine, and y: pyrimidine.

FIG. 11 shows the base sequence in the neighborhood of the initiation site on the 5' side of FcγBP genomic DNA wherein capital letters show exons while small letters show introns. The underlined parts are identical with the sequence of the cDNA. The shaded thick letters show the TGA stop codon in frame and the ATG codon which is assumed to be the initiation site. Bases in the exons are exclusively numbered by referring the 5' end of the cDNA clone NZ4 as to +1.

DETAILED DESCRIPTION OF THE INVENTION

Figure 1:
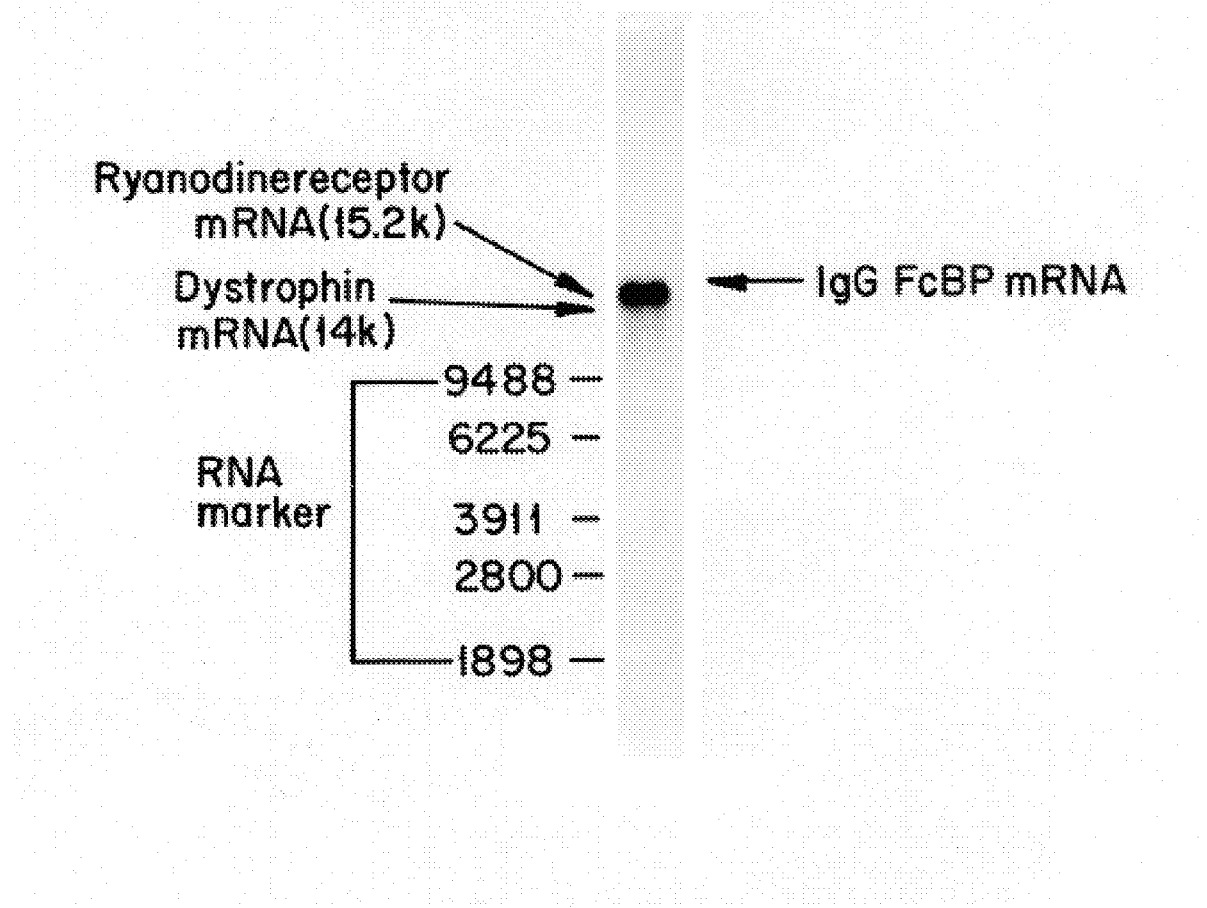
FIG. 1 is an electrophorogram showing the result of the hybridization of FcγBP mRNA performed with the use of the probe Q.

The cDNA encoding FcγBP can be obtained by, for example, preparing the mRNA from cells producing FcγBP and converting the mRNA into the double stranded cDNA by a known method. Although human colonic mucosal epithelial cells are employed in the present invention as the mRNA source, use may be made of homogenates of tissues in which FcγBP is distributed (for example, human small intestine, duodenum, stomach, submandibular gland, sublingual gland, common bile duct, bronchus, etc.) without restriction. Also, it is known that a cell line HT29-18-N2 originating in human colonic cancer cells and its subspecies produce FcγBP. Thus, use may be made of these cell lines as the mRNA source.

In the present invention, a modified AGPC method (P. Chomczynski et al., Analytical Biochem., 162:156–159, 1987) is employed to prepare the mRNA. Alternatively, all RNAs may be prepared in accordance with the method of Chirgwin et al. (Biochemistry 18:5294–5299, 1979). It is also possible to prepare the mRNA by the methods employed in cloning the genes of other physiologically active proteins, for example, treating with a surfactant in the presence of a ribonuclease inhibitor (for example, a vanadium complex) or treating with phenol.

To obtain the double stranded DNA from the mRNA thus obtained, reverse transcription is performed by using the mRNA as a template and an oligo(dT) or random primer complementary to the polyA-chain at the 3' end or a synthetic oligonucleotide corresponding to a part of the amino acid sequence of FcγBP as a primer to thereby synthesize a DNA complementary to the mRNA (i.e., the cDNA).

In the present invention, the cDNA is constructed by the reverse transcription from the polyadenylated RNA in accordance with the modified Gubler & Hoffman method with the use of a cDNA synthesis kit manufactured by Amersham or InVitrogen and random primers.

Then an adaptor is ligated to this cDNA followed by the insertion into the EcoRI site of the λgt11 vector. The cDNA library thus constructed is packaged into the λ phage by using an in vitro packaging kit Gigapack II Gold manufactured by Stratagene and expressed in *Escherichia coli*. The cDNA protein thus expressed is screened with the use of monoclonal antibodies as a probe.

As the antibodies to be used in the above-mentioned cloning, those capable of detecting FcγBP in Western blotting are selected from among 3 monoclonal antibodies (K9, K10 and K17) which can inhibit the binding of IgGFc to FcγBP (Kobayashi et al., J. Immunology, 146:68–74, 1991; Kobayashi et al., J. Immunology, 143:2567–2574, 1989). Namely, when the antibody K9 is used, a band larger than about 200 kDa is observed under reducing conditions. When the antibody K17 is used, on the other hand, bands at 70–80 kDa and 130–140 kDa are observed under nonreducing conditions. Based on these results, these monoclonal antibodies capable of recognizing 2 different epitopes are employed in the cloning.

As the result of this screening, one clone, which is named probe Q (600 bp), is obtained from about 1,000,000 clones by using the antibody K9, while 7 clones, among which a DNA fragment of 700 bp is named probe A and another DNA fragment of 600 bp is named probe B, are obtained from about 600,000 clones by using the antibody K17.

By using this probe Q, the size of the FcγBP mRNA is estimated through comparison with the mRNAs of known proteins. As a result, it is estimated that the FcγBP mRNA molecule has a size of about 17 kbp (FIG. 1).

Next, the second cDNA library packaged into λgt10 is screened with the use of the probes Q, A and B. First, cDNA clones hybridizable with one of the probes Q, A and B are separated. From among these clones, one hybridizable exclusively with the probe A is obtained. The end of this clone on the opposite side to A is referred to as probe X (about 700 bp) and a cDNA clone hybridizable with this probe X is separated. The obtained clone, which has X at the center and the A-B region at one end, is named X1. Subsequently, a part (about 800 bp) of this clone X1 opposite to the A-B region is named probe Y and the cDNA library is screened again. Thus a cDNA clone hybridizable with this probe Y is obtained and named Y1. This clone Y1 has a part of the X region at one end and the Y region at the center. A part (about 150 bp) of this clone Y1 at the opposite end to the X region is named probe Y150. By using this probe Y150, the cDNA library is screened again. Thus a clone showing the longest extension on the opposite side to the Y150 region is selected and named clone C72. Subsequently, a part (about 450 bp) of this clone C72 in the neighborhood of the opposite end to the Y150 region is named probe Z and cDNA clones hybridizable with this probe Z are separated. From among these clones, one having the longest part not overlapping the clone C72 is separated and named clone NZ4.

From among the cDNA clones hybridizable each of the clones A, B and Q, on the other hand, one having the same base sequence in the A-B region as that of the A-B region in the clone X1 is selected and named clone V11.

Figure 2:
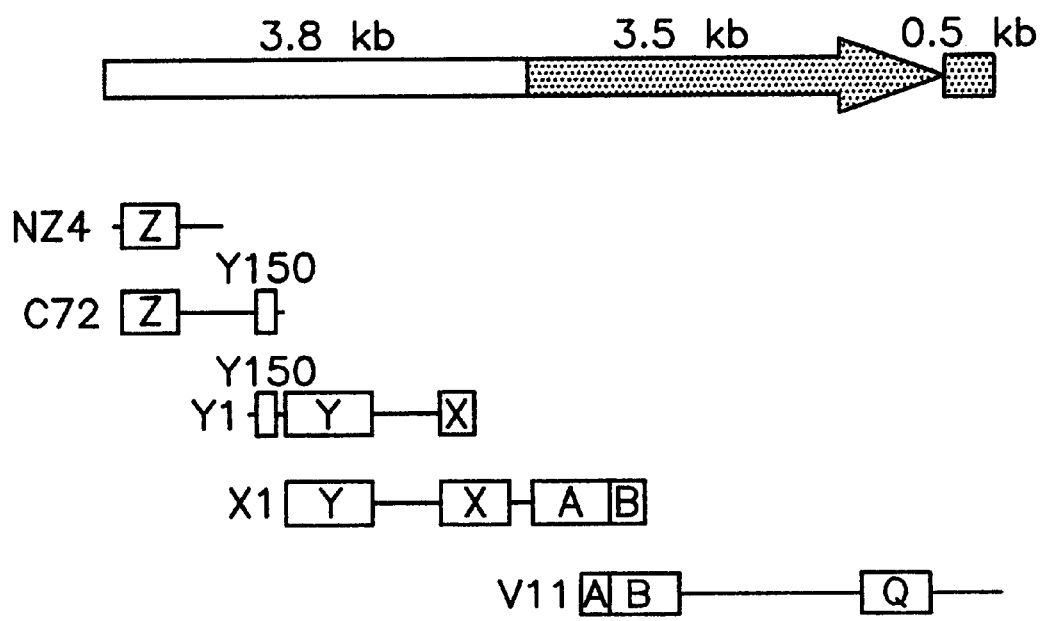
FIG. 2 shows the relations among the partial cDNA (about 7.8 kbp) employed in the expression of FcγBP and the clones NZ4, C72, Y1, X1 and V11.

Then the base sequences of these 5 clones (X1, Y1, C72, NZ4 and V11) are identified and the amino acid sequences of the proteins are confirmed. Thus an open reading frame having ATG as the initiation codon is found out (FIG. 2).

Further, a partial cDNA (about 7.8 kbp) encoding FcγBP is obtained from these clones and its base sequence is identified (SEQ ID NO:6 shows the base sequence and the amino acid sequence).

Furthermore, the cDNA clones obtained by screening via the hybridization with the use of the above-mentioned probe A, B or Q are each amplified in *Escherichia coli* and mapped by using the probes A, B and Q. As a result, it is assumed that the cDNA of FcγBP has a structure of 16.4 kbp in the full length with a unit of 3.5 kbp, wherein sequences homologous respectively with the probes A, B and Q are linked together in the order of A→B→Q, repeated in tandem.

In the cDNA clone hybridizable with the probe B, a part of the base sequence of the probe is amplified by PCR and the base sequence of the fragment thus obtained is analyzed. Thus it is clarified that the full-length cDNA of FcγBP has the structure shown in FIG. 8 and the base sequence and amino acid sequence represented by SEQ ID NO:7 in Sequence Listing.

By integrating the gene encoding FcγBP thus cloned into an appropriate vector, procaryotic or eucaryotic host cells can be transformed.

Furthermore, an appropriate promoter or a sequence relating to the phenotypic expression may be introduced into such a vector to thereby express the gene in host cells. It is also possible that the target gene is ligated with an additional gene encoding another polypeptide and thus expressed as a fused protein so as to facilitate the purification or elevate the expression yield. Also, the target protein can be excised by performing an appropriate treatment in the process of the purification.

It is generally considered that a eucaryotic gene shows polymorphism as is the case with that for human interferon. Owing to this polymorphism, therefore, one or more amino acids are replaced in some cases, or every amino acid remains unchanged regardless of changes in the base sequence in other cases.

Accordingly, it is sometimes observed that a polypeptide which has the deletion, addition or replacement of one or more amino acids in the amino acid sequence represented by SEQ ID NO:6 or SEQ ID NO:8 in Sequence Listing or a part of the same has the IgG Fc portion-binding activity. For example, it is publicly known that when the base sequence corresponding to cysteine in human interleukin 2 (IL-2) gene is converted into another base sequence corresponding to serine, the polypeptide thus obtained still sustains the IL-2 activity (Wang et al., Science, 224:1431, 1984).

When polypeptides are expressed in eucaryotic cells, glycosylation occurs in many cases. The glycosylation may be regulated by converting one or more amino acids. In such a case, the obtained polypeptide sometimes has the IgG Fc portion-binding activity. When the FcγBP gene of the present invention is artificially modified and the polypeptides thus obtained have the IgG Fc portion-binding activity, therefore, genes encoding these polypeptides are all involved in the scope of the present invention.

The present invention further involves genes encoding polypeptides which have the IgG Fc portion-binding activity and are hybridizable with the genes represented by SEQ ID NO:6 or SEQ ID NO:7 in Sequence Listing or a part of the same. The hybridization may be carried out under the conditions commonly employed in probe hybridization (refer to, for example, Molecular Cloning: A Laboratory Manual, Sambrook et al., Cold Spring Harbor Laboratory Press, 1989).

As described above, it is clear that the present invention involves not only the base sequences encoding the amino acid sequences represented by SEQ ID NO:6 and SEQ ID NO:7 in Sequence Listing but also variously modified DNAs so long as they are capable of expressing proteins binding specifically to the Fc portion of immunoglobulin (IgG). Also, DNA fragments having the above-mentioned function fall within the scope of the present invention.

The expression vector of the present invention involves a replication source, a selective marker, a promoter, an RNA splice site, a polyadenylation signal, etc.

Examples of the procaryotic host cells to be used in the expression system of the present invention include *Escherichia coli, Bacillus subtilis*, etc. Examples of eucaryotic host cells usable herein include yeasts and slime molds. Also, use can be made of insect cells such as Sf9 as the host cells. Further, examples of host cells originating in animal cells include COS, CCHO, C127 and 3T3 cells.

Thus the host cells are transformed by the gene encoding the target FcγBP and the resulting transformant is incubated. Then the protein having the IgG Fc region-binding activity thus produced can be intracellularly or extracellularly separated and purified.

The methods for the separation and purification of the protein having the IgG Fc portion-binding activity, namely, the target protein of the present invention are not restricted to those employed in the Examples given hereinafter but can be arbitrarily selected from among the methods commonly employed in the separation and purification of proteins. For example, various chromatographic procedures, ultrafiltration, salting out, dialysis, etc. may be appropriately selected and combined therefor.

Then it is examined whether or not the recombinant protein thus obtained has the activity of binding to human IgG similar to the native FcγBP. As a result, it is proved that this recombinant protein binds specifically to human IgGFc.

Figure 8:
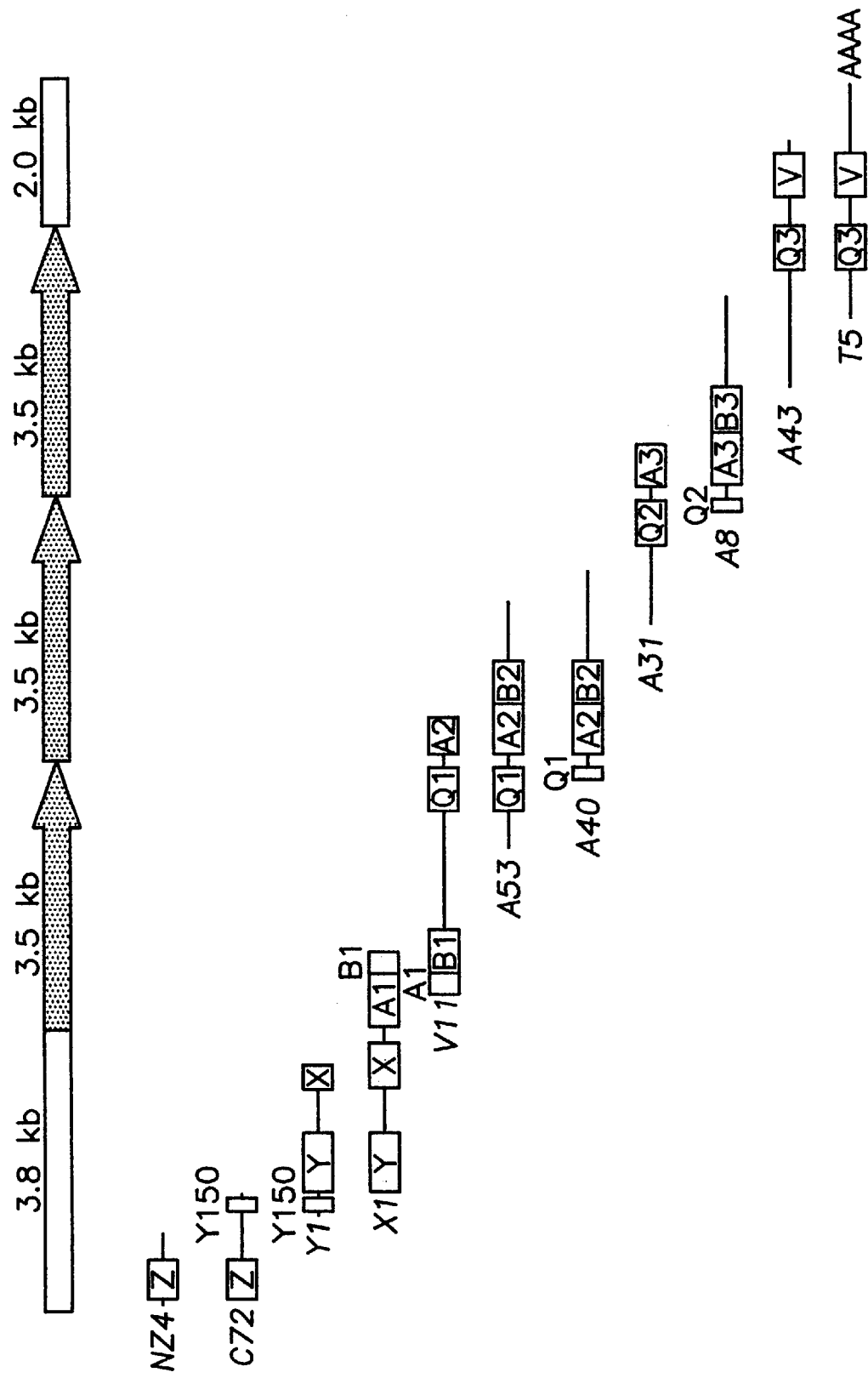
FIG. 8 shows the structure of the full length cDNA of FcγBP.

As described above, the full-length cDNA of FcγBP of the present invention has the structure shown in FIG. 8 and the base sequence and the amino acid sequence represented by SEQ ID NO:7 in Sequence Listing. Further, it is confirmed again in the following manner that a series of cDNAs employed in the present invention originate in a single mRNA. That is, cDNA fragments in a repeating structure different from pNV11SR including the 5' end cDNA employed in the expression are expressed and reacted with the monoclonal antibodies K9 and K17 which recognize FcγBP. As a result, it is confirmed that these cDNA products are recognized by either or both of K9 and K17.

Further, the tissue-specificity of the expression of the mRNA of FcγBP is examined. Thus it is found out that this protein is expressed in human placenta. Accordingly, it is possible to identify a tissue synthesizing the FcγBP mRNA by Northern blotting or in situ hybridization with the use of the gene encoding FcγBP of the present invention or a part of the same as a probe.

Furthermore, the occurrence of polymorphism on the chromogen of FcγBP can be proved by using restriction enzymes.

The following Examples will be given in order to illustrate a process for obtaining the gene encoding FcγBP of the present invention, a recombinant vector containing this gene, a transformant containing this vector, the target protein obtained by incubating this transformant and processes for producing each of them. However, it is to be understood that the present invention is not restricted thereto.

EXAMPLES

Example 1

Cloning of Partial cDNA Encoding FcγBP by Using Monoclonal Antibody (A: Construction of cDNA library)

(1) Preparation of Human Colonic Mucosal Epithelial Cell

A human colonic tissue piece was thoroughly washed with RPMI medium containing 10% of FBS and mechanically peeled off from the muscularis mucosae to thereby separate the epithelial cells from the lamina propria mucosae. Next, it was fixed to the shaft and vigorously stirred with a stirrer in 10% FBS/5 mM EDTA/PBS (−) for 90 minutes on ice to thereby separate the epithelial cells. Then the solution containing the epithelial cells was centrifuged at 1,500 rpm for 10 minutes to thereby give a precipitate of the cells.

(2) Purification of mRNA

All RNAs were extracted from the mucosal epithelial cells by a modified AGPC method (P. Chomczynski et al., Analytical Biochem., 162:156–159, 1987). Namely, to 1 ml of the cell pellets was added 9 ml of a denaturation solution [4 M of guanidine thiocyanate, 25 mM of sodium citrate (pH 7), 0.5% of Sarkosyl, 0.1 M of 2-mercaptoethanol]. After lysing the cells, 1 ml of 2 M sodium acetate (pH 4), 10 ml of a saturated aqueous solution of phenol and 2 ml of chloroform/isoamyl alcohol (49:1) were successively added thereto. Then the mixture was stirred for 10 seconds, ice-cooled for 15 minutes and then centrifuged at 10,000×g for 15 minutes and the supernatant was taken up. To 8 ml of this supernatant were similarly added 0.8 ml of sodium acetate, 8 ml of water-saturated phenol and 1.6 ml of chloroform/isoamyl alcohol. Then the mixture was stirred for 10 seconds, ice-cooled for 15 minutes and centrifuged at 10,000×g for 15 minutes and the supernatant was taken up. To 7 ml of this supernatant was added the same amount of chloroform/isoamyl alcohol and the obtained mixture was stirred and centrifuged to thereby give the supernatant. To the obtained supernatant was added the same amount of isopropanol and the mixture was cooled at −20° C. for 30 minutes and then centrifuged at 10,000×g for 15 minutes to thereby recover the precipitate of all RNAs.

To a solution of 1 mg of the all RNAs, an elution buffer [10 mM of Tris-HCl (pH 7.5), 1 mM of EDTA, 0.1% of SDS] was added so as to adjust the total volume to 1 ml. Then 1 ml of OligoTex-dT30 <Super> (manufactured by Takara Shuzo) was added thereto and the mixture was heated at 65° C. for 5 minutes and quenched on ice for 3 minutes. After adding 0.2 ml of 5 M NaCl and maintained at 37° C. for 10 minutes, the mixture was centrifuged at 15,000 rpm for 3 minutes and the supernatant was carefully removed. The pellets were suspended in 2.5 ml of a washing buffer [10 mM of Tris-HCl (pH 7.5), 1 mM of EDTA, 0.5 M of NaCl, 0.1% of SDS] and centrifuged at 15,000 rpm for 3 minutes and the supernatant was carefully removed. The pellets were suspended in 1 ml of sterilized water, heated at 65° C. for 5 minutes and then quenched on ice for 3 minutes. Then it was centrifuged at 15,000 rpm for 3 minutes and the supernatant was taken up. To the supernatant were added 50 μl of 5 M NaCl and 2.5 ml of ethanol and the mixture was cooled at −20° C. for 30 minutes and centrifuged (3,000 rpm, 4° C.). Then the precipitate of the polyadenylated RNA was recovered.

(3) Synthesis of cDNA

From the mRNA, cDNA was synthesized by a modified method of Gubler and Hoffman [U. Gubler and B. J. Hoffman (1983), Gene, 25:263] with the use of a cDNA synthesis kit manufactured by Amersham or InVitrogen. Namely, 5 μg of the polyadenylated RNA prepared from the colonic mucosal epithelial cell was incubated at 42° C. for 90 minutes in 50 μl of a buffer (manufactured by Amersham) containing 50 U of human placenta ribonuclease inhibitor, 1 mM of dATP, 1 mM of dGTP, 1 mM of dCTP, 0.5 mM of dTTP, 100 U of AMV reverse transcriptase and sodium pyrophosphate together with 750 ng of random hexanucleotide or 4 μg of oligo(dT) primer. 50 μl of this reaction mixture was reacted in a buffer (manufactured by Amersham) containing 4.0 U of *Escherichia coli* ribonuclease H and 115 U of *Escherichia coli* DNA polymerase I successively at 12° C. for 60 minutes and at 22° C. for 60 minutes and then incubated at 70° C. for 10 minutes. After returning into ice, 10 U of T4 DNA polymerase was added thereto and reacted at 37° C. for 10 minutes. Next, the reaction was ceased by adding 10 μl of 0.25 M EDTA (pH 8). To 250 μl of the reaction mixture were added the same amount of 7.5 M ammonium acetate and 4 times as much ethanol. After stirring, the mixture was cooled at −20° C. for 30 minutes and centrifuged to thereby collect cDNA. The cDNA was dissolved in 10 μl of sterilized water and 1 μl of this solution was electrophoresed on a 0.8% agarose gel to confirm the synthesis and determine the concentration.

(4) Ligation of Adaptor

To the cDNA synthesized in the above (3) was added 10 times by mol as much an adaptor (EcoRI-NotI-BamHI adaptor, manufactured by Takara Shuzo). Then a ligation solution A (ligation kit, manufactured by Takara Shuzo) in an amount 8 times more than the total mixture and a ligation solution B (ligation kit, manufactured by Takara Shuzo) in the same amount as the total mixture were added thereto. After thoroughly stirring, the resulting mixture was incubated at 16° C. for 30 minutes to thereby ligate the adaptor to the cDNA.

This reaction mixture was electrophoresed on a 1% low melting agarose gel (Sea Plaque Agarose, manufactured by Takara Shuzo) in a TAE buffer system and thus a gel containing a cDNA fraction of 0.5 kbp or above was recovered. By this procedure, the adaptor not ligated to the cDNA was eliminated at the same time. Then TE buffer in an amount twice more than the wet weight of the gel recovered above was added thereto and the mixture was maintained at 65° C. for 10 minutes. After thus dissolving the agarose gel, Tris-saturated phenol in the same amount as the total mixture was added thereto. Then the resulting mixture was thoroughly stirred, ice-cooled and centrifuged. The aqueous phase was taken up and treated with the same amount of Tris-saturated phenol again. After centrifuging, the aqueous phase was taken up and the same amount of chloroform was added thereto. The mixture was thoroughly stirred and centrifuged. Next, the aqueous phase was taken up and 3 M sodium acetate in an amount 1/10 times as much, 20 μg of glycogen (manufactured by Boehringer-Mannheim) and ethanol in an amount 2.5 times as much were added thereto. After cooling at −20° C. for 30 minutes, the mixture was centrifuged at 15,000 rpm for 10 minutes at 4° C. to thereby give a precipitate of the cDNA.

(5) Construction of λgt11 Library

The cDNA obtained in the above (4), to which the adaptor had been ligated, was dissolved in 96 μl of a solution comprising 500 mM of Tris-HCl (pH 7.5), 100 mM of $MgCl_2$, 10 mM of DTT and 10 mM of ATP. After adding 40 U of polynucleotide kinase, the mixture was incubated at 37° C. for 60 minutes to thereby phosphorylate the 5' end of the adaptor. After the completion of the reaction, 200 μl of TE buffer and 300 μl of Tris-saturated phenol were successively added thereto. The obtained mixture was stirred and centrifuged (15,000 rpm, room temperature, 2 minutes) and the supernatant was taken up. Similarly, centrifugation was performed by successively using a Tris-saturated phenol/chloroform (1:1) solution and a chloroform solution containing 2% of isoamyl alcohol to thereby give 250 μl of the supernatant finally. To this supernatant were added 250 μl of a 4 M ammonium acetate solution and 1,250 μl of ethanol. The obtained mixture was cooled at −20° C. for 30 minutes and then centrifuged (15,000 rpm, 4° C., 10 minutes) to thereby recover the precipitate. To the cDNA precipitate was added 1 μg of EcoRI-digested dephosphorylated λgt11 arm (#234211, manufactured by Stratagene) and dissolved in 5 μl of a solution containing 100 mM (the final concentration) of Tris-HCl (pH 7.6), 5 mM of $MgCl_2$ and 300 mM of NaCl. Then 5 μl of the ligation solution B (DNA ligation kit, manufactured by Takara Shuzo) was added and the mixture was thoroughly stirred and then reacted at 26° C. for 10 minutes. To package the cDNA into the λ phage, 4 μl of the ligation mixture containing the cDNA was added to 10 μl of Freeze/Thaw extract (Gigapack II gold, manufactured by Stratagene). Immediately thereafter, Sonic extract (Gigapack II gold) was added thereto and the resulting mixture was slowly stirred. After incubating at 22° C. for 2 hours, 500 μl of a solution for diluting the phage [5 g of NaCl, 2 g of $MgSO_4.7H_2O$, 50 ml of 1M Tris-HCl (pH 7.5), 5 ml of 2% gelatin per liter] and 10 μl of chloroform were added and thus the in vitro packaging reaction was completed. This phage solution was stored at 4° C. and employed in screening.

Example 2

Cloning of Partial cDNA Encoding FcγBP by Using Monoclonal Antibody (B: Screening of cDNA library by using antibody)

(1) Screening $1 \times 10^4$ pfu (200 μl) of the cDNA library of the colonic mucosal epithelial cells packaged into the λ phage, which had been prepared in the above Example 1, was mixed with 200 μl of an *Escherichia coli* strain Y1090γ⁻, which had been incubated overnight, and then incubated at 37° C. for 15 minutes. Separately, 0.8% top agarose gel was mixed with LB medium, dissolved therein and maintained at 55° C. Then 5 ml of this material was added to the preincubation of the phage with *Escherichia coli* and mixed homogeneously. The obtained mixture was uniformly spread onto a 1.5% LB agarose plate (10×14 cm) and stored in an incubator at 42° C. for 3.5 hours. After confirming that small plaques had been formed, a nylon-reinforced nitrocellulose filter (#BA-S85, manufactured by Schleicher & Schnell), which had been impregnated with IPTG and air-dried, was placed on the plate followed by storage at 37° C. for 3.5 hours. Then the filter was peeled off from the plate and shaken in a washing liquor [0.05% of Tween-20, 25 mM of Tris-HCl (pH 7.5), 150 mM of NaCl, 3 mM of KCl] at room temperature for 30 minutes. Subsequently, it was shaken in PBS (−) containing 5% of skim milk at room temperature for 30 minutes for blocking and then washed with the washing liquor for 20 minutes twice. Then the nitrocellulose membrane was immersed in 5 ml of a hybridoma culture supernatant containing the mouse monoclonal antibody K9 or K17 which had been prepared against FcγBP in colonic mucosal epithelial cells [Kobayashi et al., J. Immunology (1991), 146:68–74; Kobayashi et al., J. Immunology (1989), 143:2567–2574]. After shaking at room temperature for 2 hours, the membrane was washed with the washing liquor for 20 minutes twice. Next, it was shaken in horse radish peroxidase (HRP)-labeled antimouse IgG (H+L) goat antiserum (manufactured by Zymed), which had been diluted 1,000-fold with the washing liquor, at room temperature for 1 hour and washed with the washing liquor for 20 minutes twice. After washing with a TBS solution free from Tween-20 for 10 minutes, it was immersed in a mixture of 50 ml of a diaminobenzidine solution [1 mg/ml of 0.1 M Tris-HCl (pH 7.2)], 50 ml of a 0.02% solution of $H_2O_2$ and 50 μl of an 8% solution of $NiCl_2$ to thereby detect positive plaques.

(2) Extraction of λDNA

By the screening with the use of the monoclonal antibody K9, a clone containing a cDNA insert of about 600 bp was obtained from among about 1,000,000 plaques. This plaque was picked up with a toothpick and the λ phage was incubated in 200 μl of a medium (LB medium containing 20 mM of $MgSO_4$, 0.2% of maltose and 5 μl of an overnight culture suspension of *Escherichia coli* Y1090γ⁻ strain) at 37° C. for 4 hours. 2 μl ($1 \times 10^7$ pfu/μl) of the culture medium containing the phage was added to 10 ml of LB medium (containing 20 mM of $MgSO_4$ and 0.25 ml of an overnight culture suspension of *Escherichia coli* Y1090γ⁻ strain) which was thus infected therewith. Then the λ phage was propagated by incubating at 37° C. for 5 hours under shaking.

After incubating for 5 to 6 hours and confirming the occurrence of bacteriolysis, 50 µl of chloroform and 2 ml of 5 M NaCl were added followed by shaking at 37° C. for 10 minutes. Then the mixture was centrifuged at 3,500 rpm for 15 minutes. To the supernatant thus obtained was added polyethylene glycol 6000 in such an amount as to give a concentration of 10%. The resulting mixture was allowed to stand on ice for 30 to 60 minutes and then centrifuged at 4,000 rpm for 15 minutes at 4° C. to thereby precipitate the phage. The precipitate was suspended in 1 ml of A buffer [0.5% of NP-40, 30 mM of Tris-HCl (pH 7.5), 5 mM of $MgCl_2$, 125 mM of KCl, 3.6 mM of $CaCl_2$, 0.5 mM of EDTA, 0.25% of sodium deoxycholate, 60 mM of mercaptoethanol] and incubated together with 100 µg/ml of RNase A and 20 µg/ml of DNase I at 37° C. for 30 minutes. Then chloroform in the same amount of the A buffer was added thereto and the mixture was stirred and centrifuged at 15,000 rpm for 2 minutes at room temperature followed by the recovery of the supernatant. Then the same amount of chloroform was added again and the mixture was centrifuged in the same manner followed by the recovery of the supernatant. To the supernatant were added 50 mM of Tris-HCl (pH 8), 20 mM of EDTA, 0.5% of SDS and 100 µg/ml of protease K and the resulting mixture was incubated at 55° C. for 60 minutes. To purify the λDNA, treatments with phenol, phenol/chloroform and chloroform were carried out each in the conventional manner so as to inactivate the DNAse, protease, etc. Then ½₀ times as much 5 M NaCl and 1 time as much isopropanol were added thereto. Thus a precipitate of the λDNA having the cDNA fragment inserted therein was obtained.

(3) Construction of Probe DNA

From the λDNA having the cDNA fragment purified in the above (2), the DNA insert was excised with the use of the BamHI restriction enzyme site and employed as a probe for screening the second cDNA library (this probe was named probe Q).

By the same method, DNA probes of 700 bp and 600 bp were excised with BamHI from the clone having the longest insert (about 1,300 bp) among the 7 λ clones obtained by using the monoclonal antibody K17. In these probes, the DNA fragment of 700 bp, which seemingly contained the cDNA encoding the epitope of the antibody K17, was referred to as probe A, while another fragment of 600 bp was referred to as probe B. These probes were employed in screening the second cDNA library.

(4) Northern Blotting

It was confirmed by Northern blotting that the probes A and Q obtained by screening with the use of the antibodies were hybridizable with the same mRNA.

15 µg of all RNAs extracted from colonic mucosal epithelial cells by the AGPC method were dissolved in 4.5 µl of sterilized water, then mixed with 2 µl of 5×MOPS buffer, 3.5 µl of formaldehyde and 10 µl of formamide and thermally denatured at 60° C. for 15 minutes. Next, the denatured product was electrophoresed on a 1% agarose gel in the presence of formaldehyde. After the completion of the electrophoresis, the RNAs were transferred onto a nylon membrane (Biodyne A, manufactured by Pall Corp.) by the capillary method overnight. After fixing the RNAs on the nylon membrane by UV-crosslinking, prehybridization was performed in 10 ml of a hybridization solution (5×SSPE, 5×Denhardt's solution, 50% of formamide, 0.5% of SDS, 100 µg/ml of thermally denatured salmon sperm DNA) at 42° C. for 8 hours.

Subsequently, the probes A and Q obtained by the antibody screening were each radioisotope-labeled with the use of α[$^{32}$P]dCTP by Megaprime Labeling Kit (manufactured by Amersham). 1×10$^8$ dpm of each probe was added together with 5 ml of the hybridization solution to the nylon membrane which had been subjected to the prehybridization. After sealing, hybridization was carried out at 42° C. overnight. The nylon membrane was washed in a solution containing 0.2×SSC and 0.2% of SDS at 65° C. for 40 minutes thrice. Then the nylon membrane was dried and exposed to an X-ray film overnight.

Thus a band of about 17 kbp was detected by using each of the probes A and Q, which proved that these 2 probes were hybridizable with the same mRNA from the viewpoint of molecular weight.

Example 3

Second Cloning of cDNA Encoding FcγBP (A: Construction of cDNA library)

(1) Preparation of Human Colonic Mucosal Epithelial Cell

A human colonic tissue piece was thoroughly washed with RPMI medium containing 10% of FBS and mechanically peeled off from the muscularis mucosae to thereby separate the epithelial cells from the lamina propria mucosae. Next, it was fixed to the shaft and vigorously stirred with a stirrer in 10% FBS/5 mM EDTA/PBS (1) for 90 minutes on ice to thereby separate the epithelial cells. Then the solution containing the epithelial cells was centrifuged at 1,500 rpm for 10 minutes to thereby give a precipitate of the cells.

(2) Purification of mRNA

All RNAs were extracted from the mucosal epithelial cells by a modified AGPC method [P. Chomczynski et al., Analytical Biochem., (1987) 162:156–159]. Namely, to 1 ml of the cell pellets was added 9 ml of a denaturation solution [4 M of guanidine thiocyanate, 25 mM of sodium citrate (pH 7), 0.5% of Sarkosyl, 0.1 M of 2-mercaptoethanol]. After lysing the cells, 1 ml of 2 M sodium acetate (pH 4), 10 ml of a saturated aqueous solution of phenol and 2 ml of chloroform/isoamyl alcohol (49:1) were successively added thereto. Then the mixture was stirred for 10 seconds, ice-cooled for 15 minutes and then centrifuged at 10,000×g for 15 minutes and the supernatant was taken up. To 8 ml of this supernatant were similarly added 0.8 ml of sodium acetate, 8 ml of water-saturated phenol and 1.6 ml of chloroform/isoamyl alcohol. Then the mixture was stirred for 10 seconds, ice-cooled for 15 minutes and then centrifuged at 10,000×g for 15 minutes and the supernatant was taken up. To 7 ml of this supernatant was added the same amount of chloroform/isoamyl alcohol and the obtained mixture was stirred and centrifuged to thereby give the supernatant. To the obtained supernatant was added the same amount of isopropanol and the mixture was cooled at −20° C. for 30 minutes and then centrifuged at 10,000×g for 15 minutes to thereby recover the precipitate of all RNAs.

To a solution of 1 mg of the all RNAs, an elution buffer [10 mM of Tris-HCl (pH 7.5), 1 mM of EDTA, 0.1% of SDS] was added so as to adjust the total volume to 1 ml. Then 1 ml of OligoTex-dT30 <Super> (manufactured by Takara Shuzo) was added thereto and the mixture was heated at 65° C. for 5 minutes and quenched on ice for 3 minutes. After adding 0.2 ml of 5 M NaCl and maintained at 37° C. for 10 minutes, the mixture was centrifuged at 15,000 rpm for 3 minutes and the supernatant was carefully removed. The pellets were suspended in 2.5 ml of a washing buffer [10 mM of Tris-HCl (pH 7.5), 1 mM of EDTA, 0.5 M of NaCl, 0.1% of SDS] and centrifuged at 15,000 rpm for 3 minutes and the supernatant was carefully removed. The pellets were suspended in 1 ml of sterilized water, heated at 65° C. for 5 minutes and then quenched on ice for 3 minutes. Then it was centrifuged at 15,000 rpm for 3 minutes and the supernatant was taken up. To the supernatant were added 50 µl of 5 M NaCl and 2.5 ml of ethanol and the mixture was cooled at −20° C. for 30 minutes and centrifuged (3,000 rpm, 4° C.). Then the precipitate of the polyadenylated RNA was recovered.

(3) Synthesis of cDNA

From the mRNA, cDNA was synthesized by a modified method of Gubler and Hoffman with the use of a cDNA synthesis kit manufactured by Amersham or InVitrogen. Namely, 5 µg of the polyadenylated RNA prepared from the colonic mucosal epithelial cells was incubated at 42° C. for 90 minutes in 50 µl of a buffer (manufactured by Amersham) containing 50 U of human placenta ribonuclease inhibitor, 1 mM of dATP, 1 mM of dGTP, 1 mM of dCTP, 0.5 mM of dTTP, 100 U of AMV reverse transcriptase and sodium pyrophosphate together with 750 ng of random hexanucleotide or 4 µg of oligo(dT) primer. 50 µl of this reaction mixture was reacted in a buffer (manufactured by Amersham) containing 4.0 U of *Escherichia coli* ribonuclease H and 115 U of *Escherichia coli* DNA polymerase I successively at 12° C. for 60 minutes and at 22° C. for 60 minutes and then incubated at 70° C. for 10 minutes. After returning into ice, 10 U of T4 DNA polymerase was added thereto and reacted at 37° C. for 10 minutes. Next, the reaction was ceased by adding 10 µl of 0.25 M EDTA (pH 8). To 250 µl of the reaction mixture were added the same amount of 7.5 M ammonium acetate and 4 times as much ethanol. After stirring, the mixture was cooled at −20° C. for 30 minutes and centrifuged to thereby collect cDNA. The cDNA was dissolved in 10 µl of sterilized water and 1 µl of this solution was electrophoresed on a 0.8% agarose gel to confirm the synthesis and determine the concentration.

(4) Ligation of Adaptor

To the cDNA synthesized in the above (3) was added 10 times by mol as much an adaptor (EcoRI-NotI-BamHI adaptor, manufactured by Takara Shuzo). Then a ligation solution A (ligation kit, manufactured by Takara Shuzo) in an amount 8 times more than the total mixture and a ligation solution B (ligation kit, manufactured by Takara Shuzo) in the same amount as the total mixture were added thereto. After thoroughly stirring, the mixture was incubated at 16° C. for 30 minutes to thereby ligate the adaptor to the cDNA.

This reaction mixture was electrophoresed on a 0.8% low melting agarose gel (Sea Plaque agarose gel, manufactured by Takara Shuzo) in a TAE buffer system and thus a gel containing a cDNA fraction of about 4 kbp or above was recovered. By this procedure, the adaptor not ligated to the cDNA was eliminated at the same time. Then TE buffer in an amount twice more than the wet weight of the gel recovered above was added thereto and the mixture was maintained at 65° C. for 10 minutes. After thus dissolving the agarose gel, Tris-saturated phenol was added in the same amount as the total mixture. Then the resulting mixture was thoroughly stirred, ice-cooled and centrifuged. The aqueous phase was taken up and treated with the same amount of Tris-saturated phenol again. After centrifuging, the aqueous phase was taken up and the same amount of chloroform was added thereto. The mixture was thoroughly stirred and centrifuged. Next, the aqueous phase was taken up and 1/10 times as much 3 M sodium acetate, 20 µg of glycogen (manufactured by Boehringer-Mannheim) and 2.5 times as much ethanol were added thereto. After cooling at −20° C. for 30 minutes, the mixture was centrifuged at 15,000 rpm for 10 minutes at 4° C. to thereby give a precipitate of the cDNA.

(5) Construction of λgt11 Library

The cDNA obtained in the above (4), to which the adaptor had been ligated, was dissolved in 96 µl of a solution comprising 500 mM of Tris-HCl (pH 7.5), 100 mM of MgCl$_2$, 10 mM of DTT and 10 mM of ATP. After adding 40 U of polynucleotide kinase, the mixture was incubated at 37° C. for 60 minutes to thereby phosphorylate the 5' end of the adaptor. After the completion of the reaction, 200 µl of TE buffer and 300 µl of Tris-saturated phenol were successively added thereto. The obtained mixture was stirred and centrifuged (15,000 rpm, room temperature, 2 minutes) and the supernatant was taken up. Similarly, centrifugation was performed by successively using a Tris-saturated phenol/chloroform (1:1) solution and a chloroform solution containing 2% of isoamyl alcohol to thereby give 250 µl of the supernatant finally. To this supernatant were added 250 µl of a 4 M ammonium acetate solution and 1,250 µl of ethanol. The obtained mixture was cooled at −20° C. for 30 minutes and centrifuged (15,000 rpm, 4° C., 10 minutes) to thereby recover the precipitate. To the cDNA precipitate was added 1 µg of EcoRI-digested dephosphorylated λgt10 arm (#233211, manufactured by Stratagene) and dissolved in 5 µl of a solution containing 100 mM (the final concentration) of Tris-HCl (pH 7.6), 5 mM of MgCl$_2$ and 300 mM of NaCl. Then 5 µl of the ligation solution B (DNA ligation kit, manufactured by Takara Shuzo) was added and the mixture was thoroughly stirred and then reacted at 26° C. for 10 minutes. To package the cDNA into the λ phage, 4 µl of the ligation mixture containing the cDNA was added to 10 µl of Freeze/Thaw extract (Gigapack II gold, manufactured by Stratagene). Immediately thereafter, Sonic extract (Gigapack II gold) was added thereto and the resulting mixture was slowly stirred. After incubating at 22° C. for 2 hours, 500 µl of a solution for diluting the phage [5 g of NaCl, 2 g of MgSO$_4$.7H$_2$O, 50 ml of 1M Tris-HCl (pH 7.5), 5 ml of 2% gelatin per liter] and 10 µl of chloroform were added and thus the in vitro packaging reaction was completed. This phage solution was stored at 4° C. and employed in screening.

Example 4

Cloning of Full Length cDNA Encoding FcγBP (B: Screening of cDNA library by using DNA probe)

(1) Blotting

200 µl of an *Escherichia coli* strain c600hfl, which had been incubated overnight, was infected with the colonic mucosal epithelial cell cDNA (2×10$^4$ pfu) packaged into λ phage and then maintained at 37° C. for 15 minutes. After adding a 0.8% top agarose/LB medium maintained at 55° C., the mixture was immediately spread onto an LB plate (10×14 cm) and incubated at 37° C. for 12 hours. When the diameter of a plaque became about 1 mm, a nylon membrane (Biodyne A, pore size: 0.2µ, manufactured by Pall Corp.) was placed thereon followed by cooling at 4° C. for 10 minutes. Then the nylon membrane was peeled off from the plate and treated with the blotting solution I (0.5 M of NaOH, 1.5 M of NaCl), the blotting solution II [1 M of Tris-HCl (pH 7.4)] and the blotting solution III [0.5 M of Tris-HCl (pH 7.4), 1.5 M of NaCl] each for 5 minutes. Then the DNA was fixed onto the nylon membrane with the use of an UV-crosslinking device (UV Stratalinker 2400, manufactured by Stratagene) at 1,200 µJ.

(2) Hybridization

To a nylon membrane having the λDNA fixed thereon was added 10 ml of a hybridization solution (5×SSPE, 5×Denhardt's solution, 50% of formamide, 0.5% of SDS, 100 µg/ml of thermally denatured salmon sperm DNA).

Next, the mixture was sealed in a hybridization bag and subjected to prehybridization at 42° C. for 8 hours. Subsequently, the probes Q, A and B obtained by the antibody screening were each radioisotope-labeled with the use of α[$^{32}$P]dCTP by the random priming method. 1×10$^8$ dpm of each probe was added together with 5 ml of the hybridization solution to the nylon membrane which had been subjected to the prehybridization. After sealing, hybridization was carried out at 42° C. overnight. When the hybridization was completed, the nylon membrane was washed in a solution containing 0.2×SSC and 0.2% of SDS at 65° C. for 40 minutes thrice. Then the nylon membrane was dried and exposed to an X-ray film overnight.

By the above-mentioned screening, 69 λ clones hybridizable with one or more of the probes A, B and Q were obtained. From each of these clones, λDNA was prepared by the method as described above, treated with a restriction enzyme EcoRI and electrophoresed to thereby confirm the size of the DNA insert.

Example 5

Estimation of FcγBP mRNA Size

By using the probe Q obtained in Example 2, the molecular size of the mRNA of FcγBP was estimated. For comparison, use was made of the mRNAs of known proteins, i.e., Dystrophin mRNA of 14.0 kbp [M. Koenig et al. (1988) Cell 53:219–228] and Ryanodine Receptor mRNA of 15.2 kbp [F. Zarzato et al., (1990), J. Biol. Chem., 265:2244–2256]. As the cDNA probes for these comparative mRNAs, synthetic probes each having the base sequence reported in the reference were prepared and employed in polymerase chain reaction (PCR) to thereby give probes DYS and RDR respectively.

The Dystrophin mRNA and Ryanodine Receptor mRNA originated in human skeletal muscle polyadenylated RNA (manufactured by Clontech).

2 μg of the polyadenylated RNA obtained from colonic mucosal epithelial cells, 1 μg of the human skeletal muscle polyadenylated RNA or a mixture thereof was electrophoresed in the same manner as the one described in Example 2 (4) and thus transferred onto a nylon membrane. Then this nylon membrane was subjected to hybridization with the use of the probe Q followed by the detection by autoradiography.

To perform the hybridization of the comparative mRNAs on the same membrane, this nylon membrane was incubated together with 20 ml of a solution containing 50 mM of Tris-HCl buffer (pH 7.5), 1.25 mM of EDTA, 3×SSC, 1×Denhard's solution, 1% of SDS and 50% of formamide at 70° C. for 1 hour. Subsequently, it was washed by shaking in a washing liquor containing 0.2×SSC and 0.1% of SDS at room temperature for 10 minutes twice. Then the nylon membrane was subjected to autoradiography and thus it was confirmed that the band had been disappeared (dehybridization).

Next, hybridization was performed by using the probe DYS in the above-mentioned manner followed by the detection by autoradiography. This nylon membrane was subjected to dehybridization by the same method as the one described above and it was confirmed that the band had been disappeared. Finally, hybridization with the probe RDR was carried out in the same manner followed by the detection of the band by autoradiography.

On the basis of the results thus obtained, the mobilities of the bands of the Dystrophin mRNA and Ryanodine Receptor mRNA were each plotted against molecular size to thereby give a standard curve. Thus the molecular size of the mRNA of FcγBP was estimated as about 17 kbp form its mobility (FIG. 1).

Example 6

Identification of Base Sequence of cDNA Encoding FcγBP (1)

To identify the base sequence of the region encoding the amino acid sequence of the protein having the IgG Fc portion-binding activity, 5 necessary clones were selected by the following methods from among the 69 λ clones obtained in the above Example 4. Then the base sequence was identified by using a DNA sequencer (Model 373A, manufactured by Applied Biosystems).

(1) Clone X1

Among the cDNA clones obtained by the screening via hybridization with the probes A, B and Q, one which was hybridizable not with the probes Q and B but with the probe A alone was obtained. Then a fragment of about 700 bp, which was excised with EcoRI and SmaI at the opposite end to the probe A in the cDNA insert of this clone, was recovered and named probe X. Next, the cDNA library was screened by the same method as the one of Example 3 with the use of this probe X. Thus a clone X1 hybridizable with the probes X, A and B was obtained. The cDNA insert of this clone X1 was cleaved with EcoRI and electrophoresed on an agarose gel to thereby separate and recover a DNA of about 3,300 bp. Then this DNA was inserted into the EcoRI site of a plasmid vector pBluescript SK(+). Subsequently, the restriction map was formed and the base sequence was identified.

(2) Clone Y1

A fragment of about 800 bp, which was excised with EcoRI and SacI on the opposite side to the region containing the probe B in the cDNA of the clone X1, was recovered and named probe Y. Next, the cDNA library was screened by the same method as the one of Example 3 with the use of this probe Y. From among the clones thus obtained, clone Y1 was obtained as the one having the longest cDNA. The cDNA insert of this clone Y1 was cleaved with EcoRI and electrophoresed on an agarose gel to thereby separate and recover a DNA of about 1,900 bp. Then this DNA was inserted into the EcoRI site of a plasmid vector pBluescript SK(+). Subsequently, the restriction map was formed and the base sequence was identified.

(3) Clone C72

A fragment of about 150 bp, which was excised with SacI and SphI on the opposite side to the region containing the probe X in the cDNA of the clone Y1, was recovered and named probe Y150. Next, the cDNA library (cDNA size ranging from 2 to 4 kbp) was screened by the same method as the one of Example 3 with the use of this probe Y150 to thereby give 9 clones. From among the cDNA inserts of the clones thus obtained, a cDNA showing the longest extension on the opposite side to the Y region from Y150 and containing Y150 was obtained and named clone C72. The cDNA insert of this clone C72 was cleaved with EcoRI and electrophoresed on an agarose gel to thereby separate and recover a DNA of about 1,200 bp. Then this DNA was inserted into the EcoRI site of a plasmid vector pBluescript SK(+). Subsequently, the restriction map was formed and the base sequence was identified.

(4) Clone NZ4

A fragment of about 450 bp, which was excised with EcoRI and SacI on the opposite side to the region containing the probe Y150 in the cDNA of the clone C72, was recovered and named probe Z. By using an incubated cell line HT-29-18-N2 originating in human colonic cancer, a λgt10 cDNA library was constructed by the same method as the one described in Example 3 (2) to (5). Then this library was screened by the same method as the one of Example 3 with the use of the above-mentioned probe Z to thereby give 4 clones. From among the clones thus obtained, one containing the longest part not overlapping C72 was selected and named clone NZ4. The cDNA insert of this clone NZ4 was cleaved with NotI and electrophoresed on an agarose gel to thereby separate and recover a DNA of about 900 bp. Then this DNA was inserted into the EcoRI site of a plasmid vector pBluescript SK(+). Subsequently, the restriction map was formed and the base sequence was identified.

(5) Clone V11

The base sequences of the clones, which were hybridizable with all of the probes A, B and Q in the screening with the use of these probes, were analyzed to thereby give a clone having the same base sequence as the one of the A-B region located on the terminal side of the clone X1 which had been previously sequenced. This clone was named clone V11. The cDNA insert of this clone V11 was cleaved with EcoRI and electrophoresed on an agarose gel to thereby separate and recover a DNA of about 3,700 bp. Then this DNA was inserted into the EcoRI site of a plasmid vector pBluescript SK(+). Subsequently, the restriction map was formed and the base sequence was identified.

Example 7

Assumption of the Presence of Clone NZ4 in the Neighborhood of 5' End of FcγBP mRNA The 5 clones obtained in Example 6 were extended toward the 5' end or the 3' end in the order of NZ4-C72-Y1-X1-V11. When the base sequences of these clones were translated into amino acids, it was assumed that they would be extended toward the 5' end. Thus a library constructed by random priming was screened with the use of the clone NZ4 DNA located to the uppermost stream at the present stage. As a result, 13 independent clones were obtained but none was extended to the 5'-upstream from NZ4. When the base sequence of NZ4 was translated into amino acids, the ATG codon corresponding to methionine seemingly located to the 5'-uppermost stream in the open reading frame was similar to Kozak's rule, which suggested that this ATG might be the initiation methionine. However, the first A in this ATG codon appeared early (i.e., located at the 9-position) in the clone NZ4 and no stop codon in frame existed in the preceding 9 bases. Therefore, it could not be denied that the cDNA sequence might be extended toward the 5' (N) end not only in the transcription product but also at the translation level. Thus the following experiment was carried out in order to examine the transcription initiation site and to assume the translation initiation site by the primer extension method.

(1) Preparation of all RNAs and Polyadenylated RNA

Two primers, i.e., primer 1 (GCTGATAGTTCTGCAGGAAGGCTGTGAGGAATTC-CTCTCTGCCAGTGTT-50 mer, SEQ ID NO:10) and primer 2 (GCTCCAGCCCAGAGTATCCACCAGCTCCATAGG-33 mer, SEQ ID NO:11) were synthesized with a DNA synthesizer (Model 394, manufactured by Applied Biosystems) and purified with an OPC column (manufactured by Applied Biosystems). 100 pmol of each primer was labeled with γ[$^{32}$P]ATP by using T4 polynucleotide kinase and purified with a Microspin™ S-200HR column (manufactured by Pharmacia). 0.5 pmol of each primer was used in each reaction.

(3) Primer Annealing and Extension Reaction

All RNAs (20 μg) and polyadenylated RNA (2.5 μg) originating in human colonic mucosal epithelial cells and HT-29-18-N2 were each mixed with the primers in an annealing buffer [10 mM of Tris-HCl (pH 7.5), 1 mM of EDTA, 250 mM of KCl] and thermally denatured by heating at 95° C. for 5 minutes. Then hybridization was carried out by incubating at 58° C. for 1 hour and then at room temperature or 37° C. for 1.5 hours. Subsequently, the extension reaction was performed in the following manner. An annealing sample was precipitated from ethanol and the obtained precipitate was dissolved in RTase buffer [33 mM of Tris-HCl (pH 8.3), 20 mM of KCl, 13.3 mM of MgCl$_2$, 13.3 mM of DTT, 0.33 mM of dNTPs, 50 μg/ml of actinomycin D]. After adding 20 U of a reverse transcriptase (RnaseH-free MMLV RTase, manufactured by Toyobo), the mixture was incubated at 42° C. for 1 hour. After the completion of the reaction, the mixture was treated at 95° C. for 3 minutes to thereby inactivate the RTase. Then RNase A was added to give a concentration of 10 μg/ml and the mixture was incubated at 37° C. for 30 minutes to thereby decompose the template RNA. After extracting successively with phenol/chloroform and chloroform and precipitating from ethanol, the precipitate was electrophoresed on a 5% sequence gel. After the completion of the electrophoresis, the gel was treated with a fixing solution (10% of acetic acid, 15% of methanol), dried and then subjected to autoradiography. As a marker, use was made of M13mp18 which had been reacted with Sequenase ver 2.0 DNA Sequencing Kit (manufactured by Toyobo).

Thus the following results were obtained. As the result of the extension with the primer 1 by using each all RNA specimen as a template, a strong band was observed at around the base of the 118-position from the primer. As the result of the extension with the primer 1 by using each polyadenylated RNA specimen as a template, a weak extension band was observed at around the base of the 157-position, in addition to the one at around the 118-position. The 5' end of the NZ4, which was considered to be located at the 5'-uppermost stream, was referred to as +1 for convenience. Then these bands corresponded respectively to +27 and −13. The extension stopped at this +27 position. This is seemingly because a palindromic structure suggesting the formation of the secondary structure at round the 5' end of NZ4 might occur. In the case of the primer 2 which was located 5'-upstream and had been constructed to minimize the formation of such secondary structure, in fact, a broad band was observed from −10 to −16 and a weak single band was further detected at the position corresponding to −23. No band was detected upstream from −23.

These results indicate that the transcription initiation site is located upstream from the 5' end of NZ4 by 10 to 20 bases. When no ATG codon in frame is involved in this range, there is a strong possibility that the ATG located at the 5'-uppermost stream at the present stage in ORF would be the translation initiation site. These facts point out that the clone NZ4 is extremely close to the N end in the order of NZ4-C72-Y1-X1-V11.

Example 8

Construction of Expression cDNA/vector System
(A: Preparation of partial cDNA employed in expression)

For the expression of the protein, the λDNA clones (#NZ4, #C72, #Y1, #X1 and #V11) having partial cDNA of FcγBP inserted therein were cleaved with EcoRI or NotI and the cDNA inserts were subcloned into a cyclic plasmid pBluescript SK(+). The plasmids thus obtained were respectively named pNZ4, pC72, pY1, pX1 and pV11.

(1) pNZ4

The λ clone (#NZ4) was completely digested with NotI. Then the insert of about 900 bp was separated and purified by agarose gel electrophoresis and then ligated to the NotI site of pBluescript SK(+). Then selection was made of a clone in which the 5'→3' direction of the protein code strand of the cDNA had been inserted in the opposite direction to the lacZ gene of the plasmid. The entire base sequence of the insert is shown in SEQ ID NO:1.

In Sequence Listing in the present invention, base sequences originating in cDNAs are given in capital letters, those originating in pBluescript SK(+) are given in small letters, and those originating in synthetic adaptors and synthetic oligonucleotides are given in underlined small letters.

Each amino acid sequence given in Sequence Listing is one which is assumed on the basis of the base sequence by the universal codon while referring ATG which agrees with Kozak's sequence as to the initiation codon.

(2) pC72

The λ clone (#C72) was completely digested with EcoRI. Then the insert of about 1,300 bp was separated and purified by agarose gel electrophoresis and then ligated to the EcoRI site of pBluescript SK(+). Then selection was made of a clone in which the 5'→3' direction of the cDNA had been inserted in the opposite direction to the lacZ gene of the plasmid. The entire base sequence of the insert is shown in SEQ ID NO:2.

(3) pY1

The λ clone (#Y1) was completely digested with EcoRI. Then the insert of about 1,900 bp was separated and purified by agarose gel electrophoresis and then ligated to the EcoRI site of pBluescript SK(+). Then selection was made of a clone of the same size. The entire base sequence of the insert is shown in SEQ ID NO:3.

(4) pX1

The λ clone (#X1) was completely digested with EcoRI. Then the insert of about 3,300 bp was separated and purified by agarose gel electrophoresis and then ligated to the EcoRI site of pBluescript SK(+). Then selection was made of a clone of the same size. The entire base sequence of the insert is shown in SEQ ID NO:4.

(5) pV11

The λ clone (#V11) was completely digested with EcoRI. Then the insert of about 3,700 bp was separated and purified by agarose gel electrophoresis and then ligated to the EcoRI site of pBluescript SK(+). Then selection was made of a clone of the same size. The entire base sequence of the insert is shown in SEQ ID NO:5.

Example 9

Construction of Expression cDNA/vector System
(B: Ligation of partial cDNA for expression of protein)

(1) Preparation of pNZC7

The plasmid pNZ4 (5 μg) having the cDNA clone inserted therein was completely digested with restriction enzymes XhoI and BglII (each 50 U) and electrophoresed on a low melting agarose gel. Then a fragment of about 400 bp containing the 5' end of the cDNA of FcγBP was separated, extracted with phenol and recovered by precipitation from ethanol (fragment 1). Next, the second plasmid pC72 (5 μg) was completely digested with XhoI and BglII. Then a fragment of about 4.2 kbp containing the vector part was isolated by electrophoresis in the same manner as the one described above (fragment 2). The fragments 1 and 2 were each dissolved in 10 μl of TE buffer. 2 μl portions of these solutions were mixed with 16 μl of the solution A (DNA Ligation Kit, manufactured by Takara Shuzo) and 4 μl of the solution B and incubated at 16° C. for 30 minutes to thereby perform ligation. By 5 μl of this mixture was transformed 100 μl of competent E. coli (XL1-Blue) which was then incubated on an LB plate containing 100 μg/ml of ampicillin at 37° C. overnight. From the colonies thus formed, the plasmid DNA was purified to thereby give a plasmid pNZC7 wherein the fragment 1 had been ligated to the fragment 2.

(2) Preparation of fragment 5 pNZC7 (5 μg) was completely digested with 50 U portions of XhoI and BstXI and a fragment of about 1,300 bp was recovered by electrophoresis (fragment 3). The third plasmid pY1 (5 μg) was completely digested with 50 U portions of BstXI and HincII and a fragment of about 420 bp was recovered by electrophoresis (fragment 4). Then these fragments 3 and 4 were ligated to each other with DNA ligase by the same method as the one described above and electrophoresed. Thus a fragment of about 1,750 bp, in which the above fragments (each 1 mole) had bound to each other at the BstXI site, was recovered (fragment 5).

(3) Preparation of pXV2

The fourth plasmid pX1 (5 μg) was completely digested with 50 U portions of HincII and BamHI and a fragment of about 2,780 bp was recovered by electrophoresis (fragment 6). The fifth plasmid pV11 (5 μg) was completely digested with 50 U of BamHI and a fragment of about 3,350 bp was recovered by electrophoresis (fragment 7). Then these fragments 6 and 7 were ligated to each other with DNA ligase by the same method as the one described above and electrophoresed. Thus a fragment of about 6,100 bp, in which the above fragments (each 1 mole) had bound to each other, was recovered (fragment 8). This fragment 8 was then ligated to pBluescript SK(+), which had been digested with HincII and BamHI, with DNA ligase and then competent E. coli was transformed thereby. From the transformants thus obtained, plasmids were recovered and the base sequence of each plasmid was identified. Thus a plasmid clone containing the fragment 8, in which the fragments 6 and 7 had been ligated in the correct direction, was obtained. The one in which the 5'→3' direction of the fragment 8 had been inserted in the opposite direction to the lacZ gene of the plasmid was referred to as pXV2.

(4) Preparation of pNV11 pXV2 was completely digested with XhoI and HincII and a fragment (about 9.1 kbp) containing the vector was recovered by electrophoresis (fragment 9). This fragment 9 was ligated to the above-mentioned fragment 5 with the use of DNA ligase and then competent E. coli (XL1-Blue) was transformed thereby. From the transformants thus obtained, plasmid pNV11 (about 10.8 kbp) containing a cDNA of about 7.8 kbp (fragment 10) was obtained.

(5) Synthesis of Oligonucleotide Adaptor Containing Stop Codon (Corresponding to UAG)

By using a DNA synthesizer (model 394, manufactured by Applied Biosystems), the following oligonucleotides, which had three TAG differing in frame and NotI and SpeI sites at both ends, were synthesized: (1) 5'-CTA GTT AGT TAG TTA GGG TAC CGC-3', SEQ ID NO:12; and (2) 5'-GGC CGC GGT ACC CTA ACT AAC TAA-3' SEQ ID NO:13. 10 nmol portions of the oligonucleotides 1 and 2 were mixed together (146 μl in total), heated at 95° C. for 1 minutes and at 85° C. for 10 minutes and then gradually cooled to 40° C. at a rate of 0.33° C./min to thereby prepare an adaptor containing the stop codon (TA-III adaptor). Then the 5' end of this adaptor (2.1 nmol) was phosphorylated by the standard method with the use of ATP and polynucleotide kinase.

0.83 pmol of the pBluescript SK(+) vector was completely digested with NotI and SpeI and then mixed with 250 pmol of the phosphorylated TA-III adaptor and ligated thereto by incubating at 16° C. for 30 minutes with the use of a DNA ligation kit. After precipitating from ethanol, the precipitate was completely digested with NotI in 50 µl of reaction volume in such a manner as to give the adaptor sequence once. Next, a band of about 3 kbp was recovered by low melting agarose gel electrophoresis, extracted with phenol and precipitated from ethanol. The precipitate thus obtained was subjected to autoligation with the use of a DNA ligation kit and then competent $E.$ $coli$ (XL1-Blue) was transformed thereby. Among the plasmids obtained from the colonies formed by incubating the transformant on an LB plate containing ampicillin overnight, selection was made of a plasmid into which the TA-III adaptor had been inserted (pBLS/TAIII).

(6) Preparation of pNV11-ST

5 µg of the plasmid pNV11 was completely digested with SpeI and a fragment of about 7.8 kbp was recovered by electrophoresis and dissolved in 10 µl of TE buffer (fragment 11). 2 µg of the plasmid (pBLS/TAIII) was completely digested with SpeI and its end was dephosphorylated with bacteria alkaline phosphatase (2 U). Then it was treated with phenol/chloroform twice and precipitated from ethanol. The precipitate was dissolved in 10 µl of TE buffer (fragment 12). Next, 2 µl portions of the fragments 10 and 11 were mixed together and ligated with the use of a DNA ligation kit (manufactured by Takara Shuzo). Then competent $E.$ $coli$ (XL1-Blue) was transformed thereby and incubated on an LB plate containing ampicillin overnight. Among the colonies thus formed, one in which the TA-III adaptor had been ligated on the 3' side of the inserted cDNA was selected by analyzing the restriction map and the base sequence. Thus the clone pNV11-ST was obtained.

The $E.$ $coli$ strain containing the above-mentioned plasmid pNV-ST has been deposited as $Escherichia$ $coli$ XL1-Blue [pNV11-ST] at National Institute of Bioscience and Human-Technology, Agency of Industrial Science and Technology (1-3 Higashi 1-chome, Tsukuba-Shi Ibaraki-Ken 305, Japan) under the accession number FERM BP-4625 in accordance with Budapest Treaty since Apr. 1, 1994.

FIG. 2 shows the relations among the partial cDNA (clone pNV11-ST; about 7.8 kbp) employed in the expression of FcγBP and the clones NZ4, C72, Y1, X1 and V11 described in Example 6 and employed in the construction thereof.

Example 10

Construction of Expression cDNA/Vector System
(C: Integration into protein expression vector)

(1) Preparation of pcDL-SRα/NOT Vector

To enable the cDNA integration, the restriction enzyme sites of a vector pcDL-SRα296 (kindly afforded by Dr. Yutaka Takebe, National Institute of Health; hereinafter sometimes referred to simply as SRα) were altered. First, 2 µg of SRα was completely digested with EcoRI and precipitated from ethanol. The precipitate was dissolved in Klenow buffer [70 mM of Tris-HCl (pH 7.5), 1 mM of EDTA, 200 mM of NaCl, 70 mM of $MgCl_2$, 1 mM portions of dATP, dCTP, dGTP and dTTP] and incubated with 0.4 U of Klenow fragment at 37° C. for 15 minutes to thereby blunt-ended the plasmid. After the precipitation from ethanol, the precipitate was dissolved in TE buffer and an NotI linker, which had been phosphorylated at the 5' end, was ligated thereto with the use of a DNA ligation kit. After the precipitation from ethanol, the precipitate was completely digested with NotI and electrophoresed on an agarose gel. Thus a DNA of about 3.7 kbp was excised and recovered by extracting with phenol. The DNA thus recovered was subjected to autoligation by using a DNA ligation kit and then competent $E.$ $coli$ (XL1-Blue) was transformed thereby. Next, the target plasmid (pcDL-SRα/NOT) digested not with EcoRI but with NotI was selected.

(2) Insertion of Expression cDNA

The protein expression vector (pcDL-SRα/NOT) was completely digested with NotI and KpnI and a fragment of about 3.7 kbp was recovered by electrophoresis (fragment A).

The cDNA insertion vector (pNV11-ST) was completely digested with NotI and KpnI and a fragment of about 7.8 kbp was recovered by electrophoresis (fragment 13). The entire base sequence of this fragment 13 is shown in SEQ ID NO:6.

This base sequence and the amino acid sequence deduced therefrom were retrieved with GenBank Rel. 80. Thus it was confirmed that the base sequence and the amino acid sequence are both novel ones.

The fragment A and the fragment 13 were ligated by using a DNA ligation kit and then competent $E.$ $coli$ (XL1-Blue) was transformed thereby. From among the colonies formed by incubating the transformant on an LB plate containing 100 µg/ml of ampicillin, a plasmid having the fragment 13 inserted therein was selected by cleaving with restriction enzymes. Thus the clone pNV11-SR was obtained.

Example 11

Expression of Partial cDNA of FcγBP in COS7 Cell (1) Recovery of Expression cDNA/Vector from $Escherichia$ $coli$ The $Escherichia$ $coli$ transformed by the FcγBP cDNA expression plasmid (pNV11-SR) obtained in Example 10 was incubated in 10 ml of LB medium at 37° C. under shaking overnight. Next, the culture medium was added to 500 ml of LB medium and shaking was continued until $OD_{600}$ reached 0.8. When $OD_{600}$ of 0.8 was attained, 2.5 ml of a chloramphenicol solution (34 mg/ml) was added thereto and the mixture was incubated overnight. After separating the cells by centrifugation, the plasmid DNA was prepared by the alkali method in the conventional manner. The plasmid was purified by ultracentrifuging (90,000 rpm, 3 hours) under density gradient of cesium chloride twice and dialyzing against TE buffer and then employed in the expression of the protein.

(2) Transfection into COS7 Cell

Transfection was performed in the following manner in order to examine the properties of the protein through the tentative expression of the plasmid vector (pNV11-SR), which had the partial cDNA (abut 7.8 kbp) of FcγBP integrated therein, in COS7 cells. $2 \times 10^7$ COS7 cells were added to a dish of 35 mm in diameter and incubated in RPMI 1640 medium (0.2% of sodium hydrogencarbonate, 10 U/ml of penicillin, 0.01% of streptomycin) containing 10% of FBS overnight. On reaching 40–60% confluence, the cells were washed with serum-free RPMI 1640 medium twice.

10 µg of the plasmid pNV11-SR dissolved in 250 µl of RPMI 1640 medium was mixed with 10 µl of a lipofection reagent (Transfectam, manufactured by Sepracor) dissolved in 250 µl of RPMI 1640 medium and the obtained mixture was immediately added onto the COS7 cells. After incubating at 37° C. for 6 hours, the medium was removed followed by the addition of 2 ml of RPMI 1640 medium containing 10% of serum. Then incubation was carried out at 37° C. under 5% of $CO_2$ for 2 days.

(3) Confirmation of Expressed Protein

The dish (diameter: 35 mm) wherein the COS7 cells transfected with pNV11-SR had been incubated was washed with 2 ml of PBS (−) twice. Then 2 ml of 99.5% ethanol was added and the cells were fixed at room temperature for 5 minutes and then washed with 2 ml of PBS (−) twice. One ml portion of culture supernatants of hybridomas producing the monoclonal antibodies (K9 and K17) against FcγBP employed in screening the λ phage were added. Each mixture thus obtained was incubated at room temperature for 1 hour and washed with PBS (−) thrice. Then horse radish peroxidase (HRP)-labeled goat antimouse IgG (H+L) F(ab')$_2$ fragment (manufactured by Zymed) was added thereto followed by incubation at room temperature for 30 minutes. After washing 2 ml of PBS (−) thrice, a 0.036% aqueous solution of hydrogen peroxide and a 0.1% solution of diaminobenzidine in 0.1 M Tris HCl (pH 7.2) were added at a ratio of 1:1 so as to effect color development (room temperature, 10 minutes). Thus the cells wherein the protein was expressed were confirmed. As a control, use was made of a sample to which no primary antibody but (HRP)-labeled goat antimouse IgG (H+L) F(ab')$_2$ fragment alone was added as the secondary antibody.

Figure 3A:
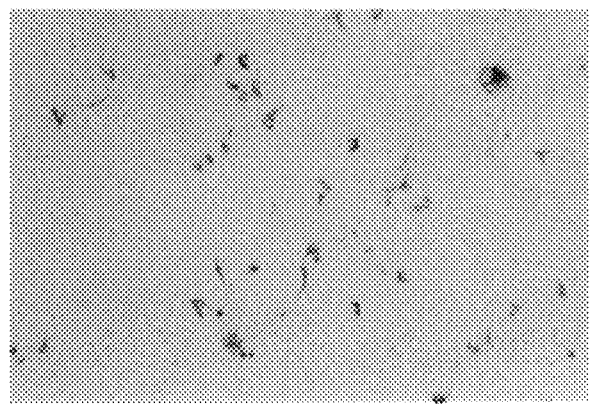
FIGS. 3A–3C provide morphological photographs proving the expression of the protein in COS7 cells transformed by using the vector pNV11-SR. As the primary antibody, the K9 monoclonal antibody-producing hybridoma culture supernatant was used in 3A, while the K17 monoclonal antibody-producing hybridoma culture supernatant was used in 3B. In 3C, no primary antibody was added (i.e., the control case). In each case, the HRP-labeled goat antimouse IgG (H+L) F(ab')$_2$ fragment was added as the secondary antibody.
Figure 3B:
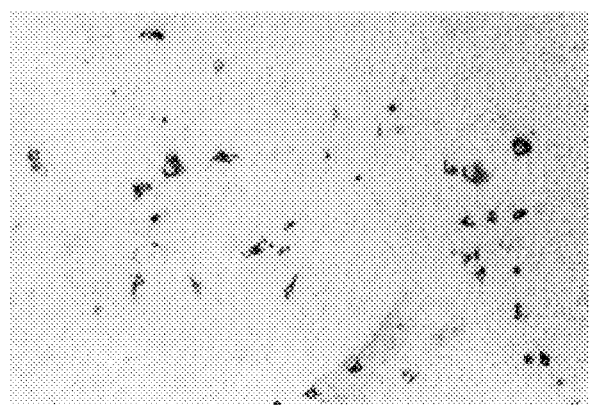
Figure 3C:
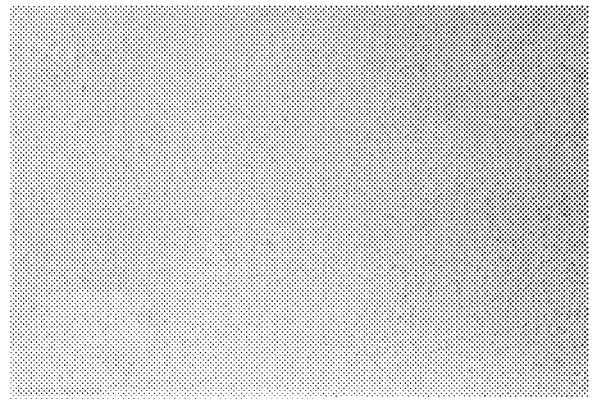

FIG. 3 shows the results. When the culture supernatant of the hybridomas producing the K9 monoclonal antibody (FIG. 3, A) or that of the hybridomas producing the K17 monoclonal antibody (FIG. 3, B) was added, cells specifically reacting therewith were observed in each case. On the other hand, no reactive cell was observed in the control (FIG. 3, C).

Example 12

Detection of Ability of Recombinant Protein to Bind to Human IgG and its Properties (1) Confirmation of Binding of Human IgG The COS7 cells (in a dish of 35 mm in diameter) transfected with the plasmid pNV11-SR, into which the partial cDNA of FcγBP had been integrated, were washed with PBS (−) twice. Then 2 ml of 99.5% ethanol was added thereto and the cells were fixed at room temperature for 5 minutes and then washed with 2 ml of pBS (−) twice. Next, a human IgG fraction (manufactured by Cappel) purified by affinity chromatography was diluted with RPMI 1640 medium containing 10% of FBS so as to give a concentration of 10 μg/ml. One ml of the obtained dilution was added to the dish and incubated at room temperature for 1 hour. After, washing with 2 ml of PBS (−) thrice, it was incubated with HRP-labeled goat antihuman IgG F(ab')$_2$ fraction (#109-D36-088, manufactured by Cosmo Bio) at room temperature for 30 minutes. After washing 2 ml of PBS (−) thrice, a mixture (1:1) of a 0.036% aqueous solution of hydrogen peroxide and a 0.1% solution of diaminobenzidine in 0.1 M Tris HCl (pH 7.2) was added so as to effect color development (room temperature, 10 minutes). Thus the binding of IgG to the expressed protein was confirmed.

(2) Specific Binding of IgG

The COS7 cells (in a dish of 35 mm in diameter) transfected with pNV11-SR were washed with 2 ml of PBS (−) twice. Then 2 ml of 99.5% ethanol was added thereto and the cells were fixed at room temperature for 5 minutes and then washed with 2 ml of pBS (−) twice.

Next, HRP-labeled human IgG fraction (#55902, manufactured by Cappel) purified by affinity chromatography was diluted with RPMI 1640 medium containing 10% of FBS so as to give a concentration of 10 μg/ml (solution 1). To this solution 1, were added the following immunoglobulins (50 μg/ml) as a competitive inhibitor.

(1) Human IgG fraction purified by chromatography (#55908, manufactured by Cappel).

(2) Human IgG Fc fraction purified by chromatography (#55911, manufactured by Cappel).

(3) Human IgG F(ab')$_2$ fraction purified by chromatography (#55910, manufactured by Cappel).

(4) Human IgM fraction purified by chromatography (#55916, manufactured by Cappel).

(5) Human serum IgA purified by chromatography (#55906, manufactured by Cappel).

(6) Human secretor IgA purified by chromatography (#55905, manufactured by Cappel).

The above competitive inhibitors (1) to (6) were separately added to the solution 1. One ml of each solution thus obtained was added to the dish in which the cells had been fixed followed by incubation at room temperature for 1 hour. After washing with 2 ml of PBS (−) thrice, a mixture (1:1) of a 0.036% aqueous solution of hydrogen peroxide and a 0.1% solution of diaminobenzidine in 0.1 M Tris HCl (pH 7.2) was added so as to effect color development (room temperature, 10 minutes). Thus the binding of IgG to the expressed protein was examined. As a control, use was made of the solution 1 containing no competitive inhibitor.

Figure 4A:
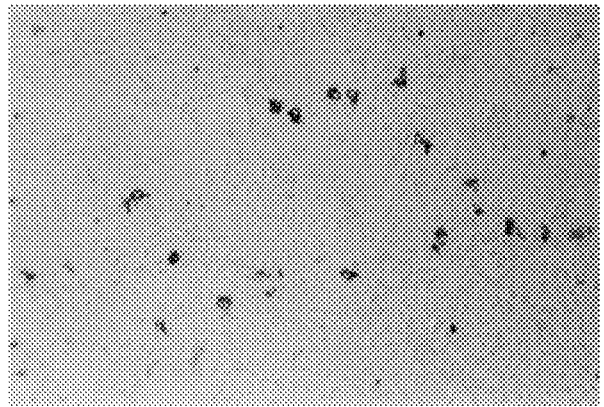
FIGS. 4A–4C provide morphological photographs showing the ability of the protein, which had been expressed in COS7 cells transformed by using the vector pNV11-SR, to bind to human IgG. In each case, HRP-labeled human IgG was employed as the primary antibody. The secondary antibodies employed as the antagonist are as follows; 4A: none (i.e., the control case), 4B: a human IgG fraction purified by chromatography, and 4C: a human IgG Fc fraction purified by chromatography.
Figure 4B:
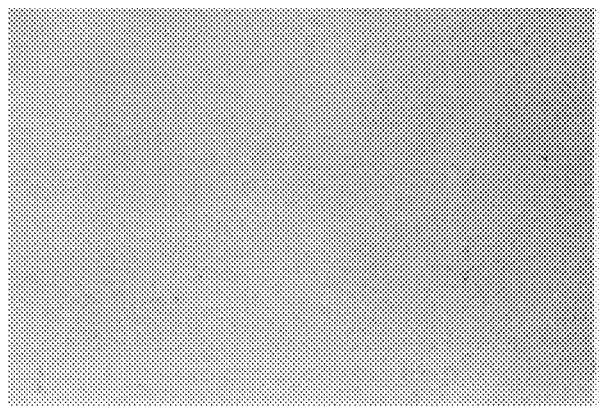
Figure 4C:
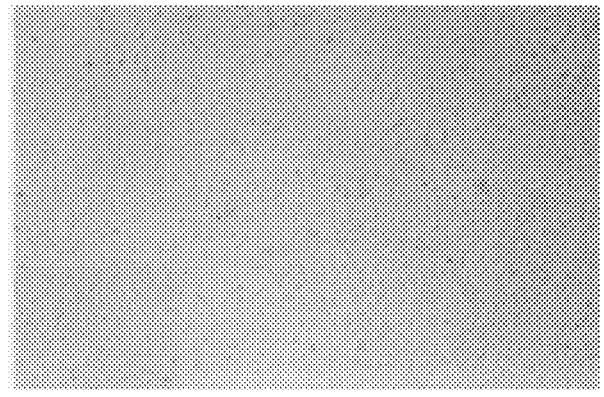
Figure 5A:
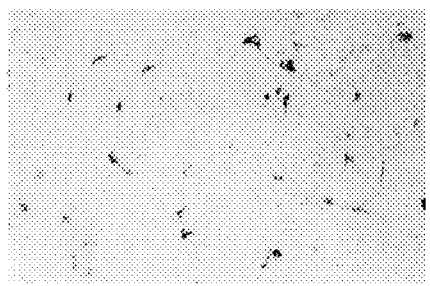
FIGS. 5A–5D provide morphological photographs showing the ability of the protein, which had been expressed in COS7 cells transformed by using the vector pNV11-SR, to bind to human IgG. In each case, HRP-labeled human IgG was employed as the primary antibody. The secondary antibodies employed as the antagonist are as follows; 5A: a human IgG F(ab')$_2$ fraction purified by chromatography, 5B: a human IgM fraction purified by chromatography, 5C: human serum IgA purified by chromatography, and 5D: human secretor IgA purified by chromatography.
Figure 5B:
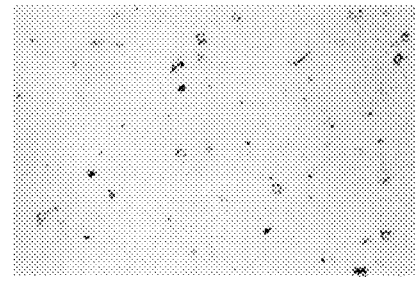
Figure 5C:
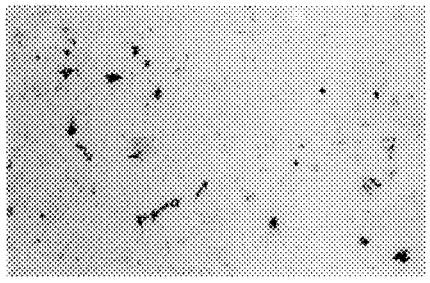
Figure 5D:
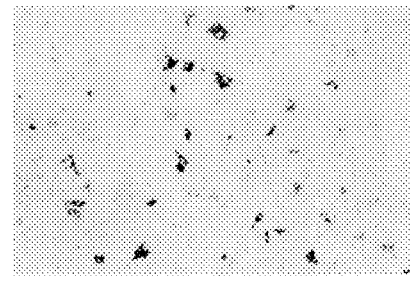

FIGS. 4 and 5 show the results. When no competitive inhibitor was added (i.e., the control), the cells were stained (FIG. 4, A). When the purified human IgG fraction (FIG. 4, B) and the purified human IgG Fc fraction (FIG. 4, C) were added, however, the cells were not stained. On the other hand, addition of the IgG F(ab')$_2$ fraction (FIG. 5, D), the human IGM fraction (FIG. 5, E), the human serum IgA (FIG. 5, F) and the human secretor IgA (FIG. 5, G) could not inhibit the binding of the HRP-labeled human IgG. These facts indicate that FcγBP binds specifically to IgG Fc in human antibodies.

Example 13

Tissue-specificity of the Expression of FcγBP mRNA

Figure 6:
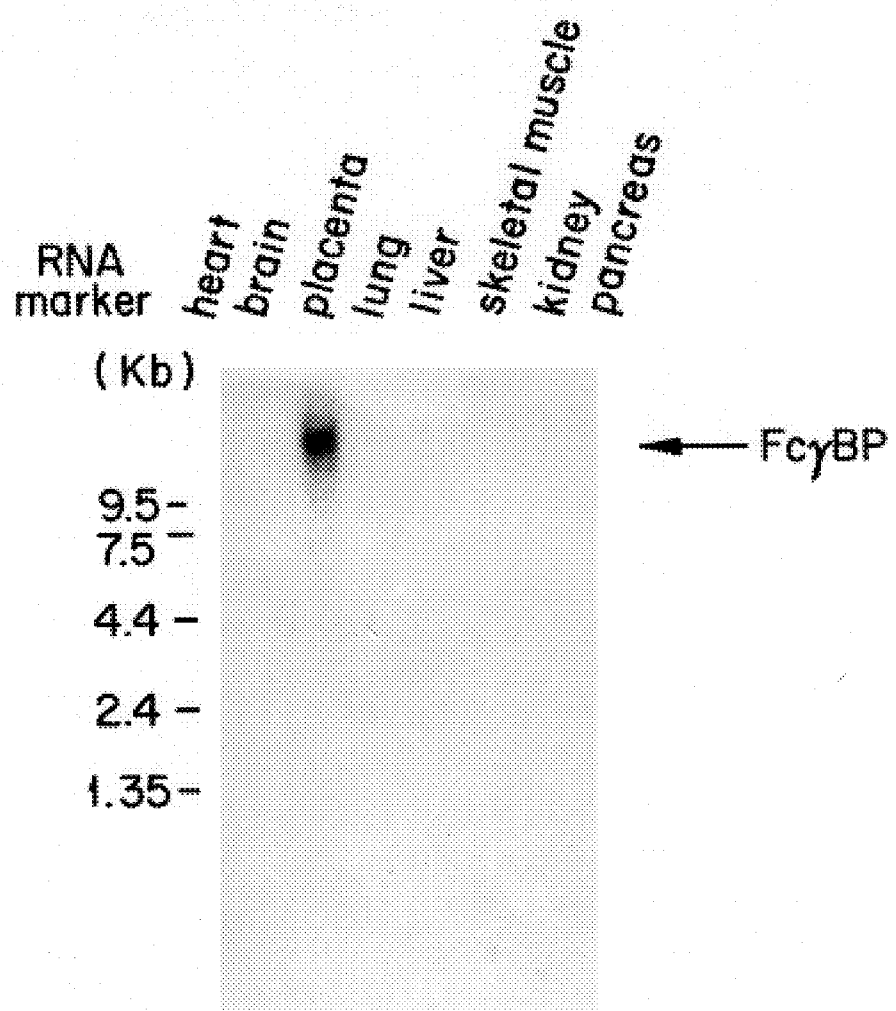
FIG. 6 is an electrophorogram of Northern blotting which shows the specificity of the expression of FcγBP mRNA in human tissues.

To examine the specificity of the expression of FcγBP in human tissues, the expression of the mRNA was analyzed by Northern blotting. A nylon membrane, on which 2 μg portions of polyadenylated RNAs purified from human heart, brain, placenta, lung, liver, skeletal muscle, kidney and pancreas had been blotted (Human Multiple Northern Blots, #7760-1, manufactured by Clontech), was subjected to prehybridization under the same conditions as those employed in Example 2 (4) followed by hybridization with the use of the probe Y labeled with [$^{32}$P]. After washing, bands were detected by autoradiography. After performing the autoradiogram at −80° C. for 2 days, a band of about 17 kbp was detected in the placenta (FIG. 6), while other tissues showed negative results. It was therefore assumed that the FcγBP protein had been expressed in the placenta.

Example 14

Northern Blotting Analysis with 3 Different Probes

The mRNA extracted from colonic mucosal epithelial cells was subjected to Northern blotting by using the probes Q and A obtained in Example 2 (3) and the probe Y obtained in Example 6 (2) in order to confirm that these probes would be hybridizable with the same mRNA.

15 μg of all RNAs extracted from colonic mucosal epithelial cells by the AGPC method were dissolved in 4.5 μl of sterilized water, mixed with 2 μl of 5×MOPS buffer, 3.5 μl of formaldehyde and 10 μl of formamide and then thermally denatured at 60° C. for 15 minutes followed by electrophoresis on a 1% agarose gel in the presence of formaldehyde. After the completion of the electrophoresis, the RNAs were transferred overnight onto a nylon membrane (Biodyne A, manufactured by Pall Corp.) by the capillary method. After fixing the RNAs to the nylon membrane by UV crosslinking, prehybridization was performed in 10 ml of a hybridization solution (5×SSPE, 5×Denhardt's solution, 50% of formamide, 0.5% of SDS, 100 μg/ml of thermally denatured salmon sperm DNA) at 42° C. for 8 hours.

Subsequently, the probes A, Q and Y were each radioisotope-labeled with α[$^{32}$P]dCTP by using Megaprime Labeling Kit (manufactured by Amersham). 1×10$^8$ dpm of each probe was added together with 5 ml of the hybridization solution to the nylon membrane which had been subjected to the prehybridization. After sealing, hybridization was carried out at 42° C. overnight. Then the nylon membrane was washed in a solution containing 0.2×SSC and 0.2% of SDS at 65° C. for 40 minutes thrice. Then the nylon membrane was dried and exposed to an X-ray film overnight.

Figure 7:
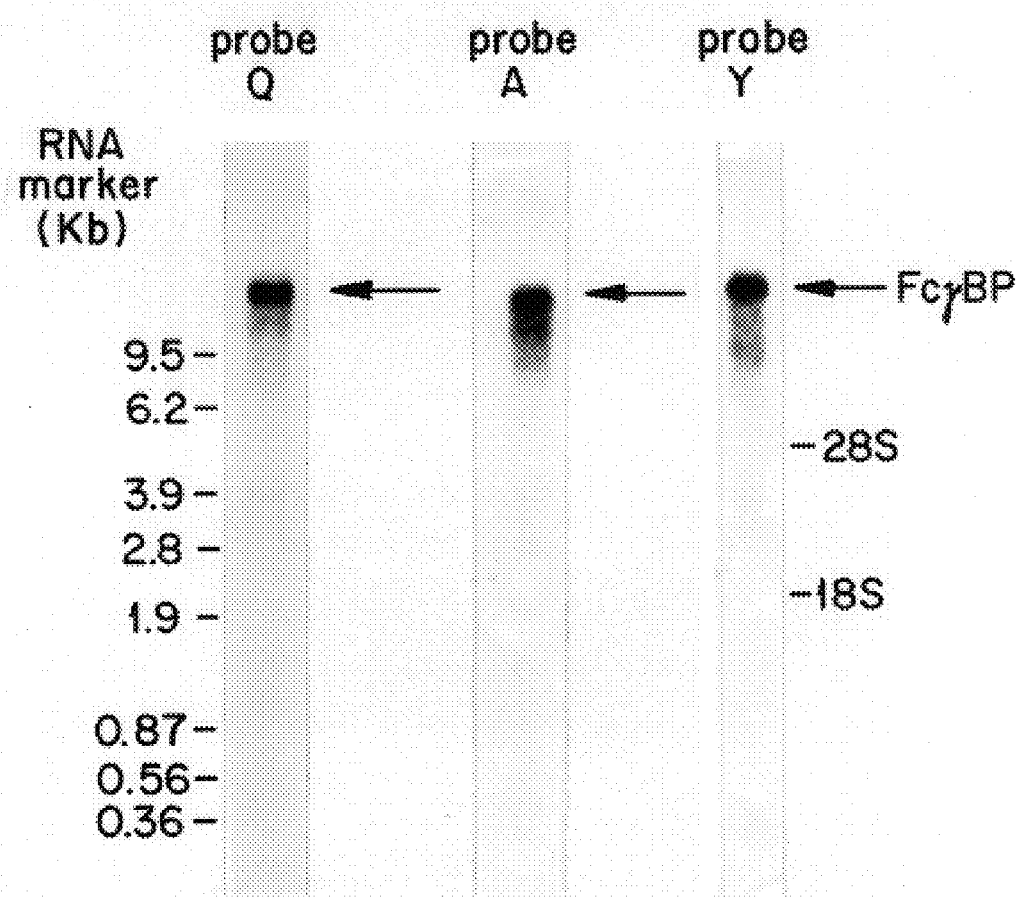
FIG. 7 is an electrophorogram showing the Northern blotting analysis of FcγBP mRNA in colonic mucosal epithelial cells wherein use was made of the probes Q, A and Y.

As a result, a band of approximately 17 kbp was detected by using each of the probes A, Q and Y. which proves that these 3 probes are hybridizable with the same mRNA from the viewpoint of molecular weight (FIG. 7).

Example 15

Identification of Base Sequence of cDNA Encoding FcγBP (2)

Examples 4 and 6 state the identification of the partial base sequence [i.e., about 7.8 kbp (7,826 bases) starting from the 5' end] of the cDNA encoding the amino acid sequence of the protein capable of binding to the Fc region of IgG. Now, the method for identifying the residual base sequence (about 8.6 kbp) will be illustrated.

(1) Structure and Classification of cDNA

The cDNA clones obtained by the screening via the hybridization with the use of the probe A, B or Q in Example 4 were each amplified in *Escherichia coli* and then mapped with the use of the probes A, B and Q. As a result, it was found out that each of these clones was hybridizable with at least one of the 3 probes and the sites homologous with the probes were located in the order of A→B, B→Q or Q→A on the cDNAs.

Based on these results, it was assumed that the FcγBP gene has a structure wherein a unit consisting of the sequences homologous with the probes A, B and Q linked together in the order of A→B→Q is repeated in tandem. In cDNAs clone hybridizable with the probe B, a part (about 280 bp) of the base sequence of the probe B was amplified by PCR with the use of the following primers.

Primer (P-1):
5'-GCC TGC GTG CCC ATC CAG-3' SEQ ID NO:14.
Primer (P-2):
5'-CTC ATA GTT GGG CAG CGAC-3' SEQ ID NO:15.

The fragments amplified by PCR were separated by agarose gel electrophoresis and collected from the gel followed by the analysis of the base sequences. Based on these base sequences, the cDNA clones hybridizable with the probe B were classified into the following 3 groups, while the cDNA clones not hybridizable with the probe B were referred to as the group 4.

Group 1: cDNA clones having the same sequence as that of the amplified fragment of the clone V11.
Group 2: those suffering from the replacement of 5 bases, compared with the sequence of the group 1, and containing no HincII site in the fragment.
Group 3: those suffering from the replacement of 7 bases, compared with the sequence of the group 1, and containing the HincII site in the fragment.
Group 4: those not hybridizable with the probe B.

(2) Clone T5

To isolate the cDNA having poly A moiety on the 3' side, the cDNA library constructed in Example 3 with the use of the oligo dT primer was screened by using the probe A, B or Q in the same manner as the one described in Example 4. As a result, hybridization occurred exclusively with the probe Q. Among the cDNA clones thus obtained, the one having the longest cDNA insert was referred to as clone T5.

The cDNA insert of the clone T5 was cleaved with EcoRI and separated and purified by agarose gel electrophoresis followed by the insertion into the EcoRI site of the plasmid vector pBluescript SK(+). Subsequently, the restriction map of T5 was formed and the entire base sequence thereof was identified.

In the cDNA insert of the clone T5, a region of about 550 bp between the BamHI site about 1 bp apart from poly (A$^+$) on the 5' side and the PstI site about 1.6 kbp apart from the poly (A$^+$) on the 5' side was referred to as probe V. This probe V was not hybridizable with the clones NZ4, C72, Y1, X1, V11, A53, A40 and A 31 but specific to T5.

(3) Clone A43

The cDNA clones hybridizable with the probe A, B or Q were subjected to hybridization by using the probe V in the same manner as the one described in Example 4 (2) to thereby give a clone which was hybridizable not with the probes A and B but with the probes V and Q. The cDNA insert of this clone was cleaved with EcoRI and separated and purified by agarose gel electrophoresis followed by the insertion into the EcoRI site of the plasmid vector pBluescript SK(+). Subsequently, the restriction map was formed and the entire base sequence thereof was identified.

As the result of the analysis of the base sequence, it was confirmed that the sequence of about 2 kbp containing the region hybridizable with the probe Q agreed with the sequence of the part overlapping T5.

(4) Clone A8

To obtain a cDNA extended toward the 5' end from the clone A43, synthesis was made of the following primers by which the base sequence (about 240 bp) around the 5' end of the clone A43 could be amplified.

Primer (P-3):
5'-TGT TGG GAC GAA TGT CGG-3' SEQ ID NO:16.
Primer (P-4):
5'-TCA CAG CCA ACC TGT GCC-3' SEQ ID NO:17.

The cDNA clones of the groups 1, 2 and 3 as classified in Example 15 (1) were subjected to PCR with the use of the above-mentioned primers (P-3) and (P-4). The fragments amplified by PCR were separated by agarose gel electrophoresis and collected followed by the analysis of the base sequences. Thus a cDNA clone having a PCR fragment of the same base sequence as that of A43 was selected from among the cDNA clones of the group 3 as classified in Example 15 (1). This clone was referred to as clone A8. The entire base sequence of the clone A8 was analyzed and it was thus confirmed that the base sequence on the 3' side was completely identical with the overlapping sequence on the 5' side of A43.

(5) Clones A53 and A40

From among the clones falling within the group 2, 2 different clones each having a region hybridizable with the probes Q and A on the 5' side were selected on the basis of the restriction maps. Between these clones thus selected, one which had the longer region overlapping the 3' side of the clone V11 was referred to as clone A53, while another one having the shorter region was referred to as clone A40.

The entire base sequences of the clones A53 and A40 were analyzed. Thus it was confirmed that a region on the 3' side of the clone A53 (about 2.4 kbp) and a region on the 5' side of the clone A40, which overlapped each other, had the same base sequence. Further, a comparison between a region (about 1.8 kbp) on the 3' side of V11 and a region on the 5' side of A53 overlapping each other indicated that the base sequences of these regions were completely consistent with each other except one base (i.e., the base at the position 6273: A in V11, G in A53).

(6) Clone A31

To screen a cDNA extended toward the 3' end from the clone A40, the following procedure was performed. In the clones A53 and A40, the base sequences of the fragments amplified by the primers (P-3) and (P-4) were identical with neither the sequence of V11 of the group 1 nor the sequence of A8 of the group 3. Thus screening was carried out in the following manner with the use of these sequences as indicators. Namely, cDNA clones hybridizable with the probe A, B or Q, from among the cDNA clones (69 in total) other than those belonging to the groups 1 and 3, were subjected to PCR by using the primers (P-3) and (P-4) and the base sequences of the fragments thus amplified were identified. Then cDNA clones having the same base sequence as those of the clones A53 and A40 were selected. From among these clones, one having the PCR-amplified sequence on the 5' side and extended toward the 3' end was selected and referred to as clone A31.

By analyzing the entire base sequence of the clone A31, it was confirmed that the sequence on the 5' side of A31 was identical with the overlapping region on the 3' side of the clone A40, while the sequence on the 3' side of A31 was identical with the overlapping region on the 5' side of the clone A8.

Example 16

Identification of Base Sequence of cDNA Encoding FcγBP (3)

The cDNA of FcγBP had a structure of 16.4 kbp in full length in which a sequence consisting of a unit of 3.5 kbp (containing regions homologous with the probes A, B and Q) was repeated thrice in tandem and the repeating sequences had a homology of at least 95% with each other (FIG. 8).

As described above, the cDNAs employed in the identification of the base sequences in this repeating structure had been cloned depending on the strong reactivities with the probes A, B and Q. By comparing these base sequences to each other, it was confirmed that the base sequences of overlapping regions were identical and thus the relationships among the cDNA were clarified. Consequently, it was proved that a series of DNA fragments originated in a single mRNA (gene). To confirm this fact again, a cDNA fragment in a repeating structure different from pNV11SR containing the 5' terminal cDNA, which had been already employed in expression, was made to undergo protein expression. Then it was examined whether or not the protein thus expressed would be recognized by the monoclonal antibodies K9 and K17 capable of recognizing FcγBP.

(1) Synthesis of Adaptor Containing Initiation Codon

To express each cDNA to be inserted into a vector from the 5' end in full length, it is required to ligate the initiation codon (ATG) to the 5' end of the cDNA. In order to achieve the translation of the protein within the same frame as that of FcγBP, it is furthermore required to regulate the frame between the initiation codon (ATG) and the 5' end of the cDNA. Thus oligonucleotides for an adaptor satisfying the following conditions were synthesized.

Each synthetic oligonucleotide contains a base sequence consisting of 7 bases (GCCATGG), which is the same as the sequence of the initiation region of pNV11SR containing the inherent initiation codon (ATG) of FcγBP, and is consistent with Kozak's rule.

To facilitate the insertion into the vector, the HindIII site and the EcoRI site were added respectively to the 5' side and 3' side of this oligonucleotide. In order to regulate the frame, the following 3 oligonucleotides (FR-1S, FR-2S and FR-3S) were constructed. Furthermore, oligonucleotides FR-1A, FR-2A and FR-3A complementary respectively to the above-mentioned oligonucleotides were synthesized.

Oligonucleotide for adaptor

FR-1S: 5'-A GCT TCT GCA GCC ATG GG-3' SEQ ID NO:18

FR-1A: 3'-AGA CGT CGG TAC CCT TAA-5' SEQ ID NO:19

FR-2S: 5'-A GCT TCT GCA GCC ATG GGG-3' SEQ ID NO:20

FR-2A: 3'-AGA CGT CGG TAC CCC-5' SEQ ID NO:21

FR-3S: 5'-A GCT TCT GCA GCC ATG GGA G-3' SEQ ID NO:22

FR-3A: 3'-AGA CGT CGG TAC CCT CTT AA-5' SEQ ID NO:23

Each oligonucleotide was synthesized by using a DNA synthesizer (model 1395, manufactured by ABI) and purified.

Next, FR-1S, FR-2S and FR-3S were annealed respectively with FR-1A, FR-2A and FR-3A in the same manner as the one described in Example 9 (5) followed by the phosphorylation of the nucleotide at the 5' end. The adaptors thus formed were referred to respectively as adaptors FR-1, FR-2 and FR-3.

(2) Alteration of TAIII/SK Vector

The XbaI site was added to the vector pBLS/TAIII containing the stop codon, which was constructed in Example 9 (5), in the following manner.

Namely, pBLS/TAIII was completely digested with a restriction enzyme XhoI by the same method as the one of Example 10 (1) and then blunt-ended. After ligating an XbaI linker having a phosphorylated end thereto, it was digested with XbaI again and autoligated. Then competent E. coli was transformed thereby and thus a vector pBLS/TAIII2 having the XbaI site inserted into the XhoI site of pBLS/TAIII was obtained.

(3) Insertion of Oligonucleotide Containing Initiation Codon

The pBLS/TAIII2 was completely digested with EcoRI and HindIII and electrophoresed on an agarose gel to thereby recover a vector part of about 3 kbp. Then the adaptors FR-1, FR-2 and FR-3 were each inserted into the above-mentioned pBLS/TAIII2 in the same manner as the one of Example 9 (5). By analyzing the base sequences, plasmids each having one adaptor (FR-1, FR-2 or FR-3) correctly inserted thereinto were obtained and referred to respectively as Fr1-SK2, Frs-SK2 and Fr3-SK2.

(4) Insertion of cDNA Fragment of FcγBP

To express the cDNA clone A53 in the same frame as that of FcγBP, the cDNA part of A53 was excised with EcoRI and inserted into the EcoRI site of Fr3-SK2. Then a plasmid in which the 5' end of cDNA was located on the initiation codon side of Fr3-SK2 was selected and referred to as piF-A53.

Similarly, the cDNA insert of the clone A8 was inserted into Fr2-SK2 to thereby give piF-A8.

Figure 9A:
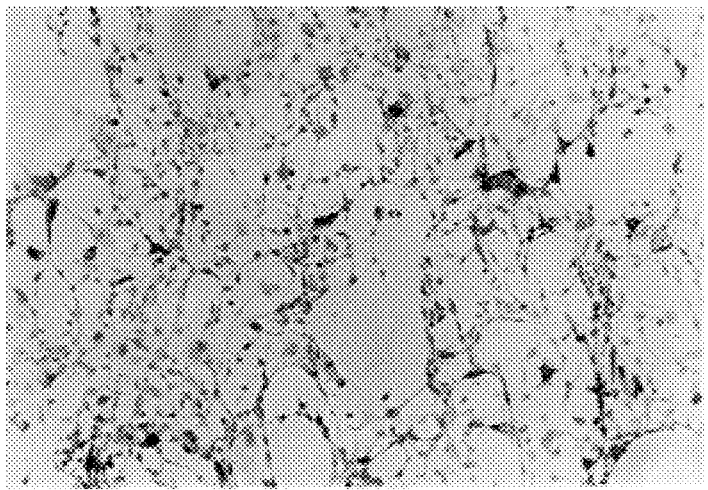
FIGS. 9A–9B provide morphological photographs showing the abilities of COS7 cells, which had been transformed by using the plasmids piF-A53 and piF-A8, to bind to a mixture of monoclonal antibodies K9/K17. 9A: piF-A53, and 9B: piF-A8.
Figure 9B:
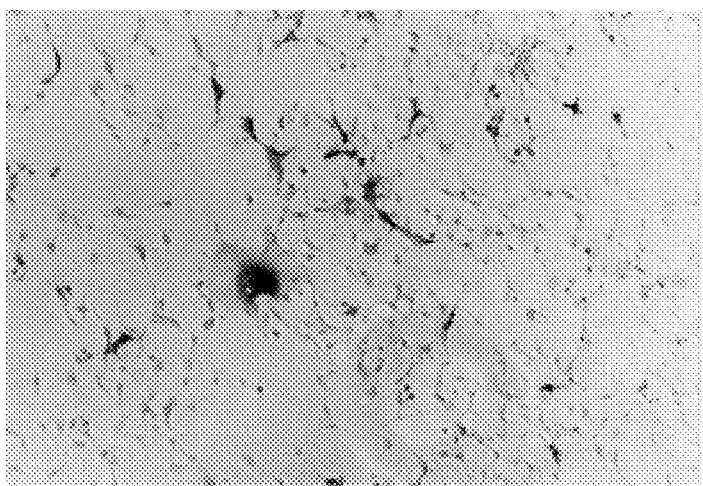

The piF-A53 and piF-A8 thus obtained were purified in the same manner as the one described in Example 11 (1) and then employed in an experiment of protein expression.
(5) Expression of piF-A53 and piF-A8 piF-A53 and piF-A8 were transfected into COS7 cells in the same manner as the one of Example 11-(2). After incubating for 2 days, the cells were stained by using monoclonal antibodies (K9/K17 mixture) by the same method as that of Example 11 (3) to thereby detect the proteins expressed tentatively. As a result, the cells transfected with piF-A53 and those transfected with piF-A8 were both stained with the monoclonal antibodies, which indicated that these cDNAs encoded some part of the protein recognized by either or both of the monoclonal antibodies K9 and K17 (FIGS. 9A and B). Thus it has been proved that A53 and A8 are each a portion of the repeated sequence of the entire cDNA of FcγBP.

Example 17

Assumption of the Presence of Clone NZ4 in the Neighborhood of 5' End of FcγBP mRNA (2)

Based on the results of the primer extension carried out in Example 7, it was assumed that the transcription initiation site might be located within about 20 bases upstream from the clone NZ4 which was located at the 5'-uppermost stream at the present stage; and that the ATG at the 9-position in NZ4 might be the translation initiation site. To examine whether or not ATG in frame or the stop codon was located upstream from NZ4, therefore, the FcγBP gene was isolated from the genomic DNA library and its partial base sequence was identified.
(1) Genomic DNA Library As the library, use was made of a commercially available one originating in human leukocytes (Vector, EMBL3 SP6/T7, manufactured by Clontech).
(2) Probe As the probes to be employed in the screening, use was made of one prepared by excising the cDNA clone NZ4 from the vector with BamHI and the synthetic oligonucleotide employed in Example 7 (primer 2: (GCTCCAGCCCAGAGTATCCACCAGCTCCATAGG-33 mer, SEQ ID NO:11) respectively labeled with α[$^{32}$P] dCTP and γ[$^{32}$P] ATP by random prime labeling (NZ4) or end labeling (primer 2).
(3) Screening The screening with the probe NZ4 was performed in accordance with the method for screening a cDNA library as described in Example 3. In the screening with the synthetic oligonucleotide probe, on the other hand, the formamide concentration of the hybridization solution was adjusted to 20% and washing was repeated 5 times in a solution containing 0.3×SSC/0.1% of SDS at 45° C. each for 30 minutes.

With each probe, a library of 1,000,000 clones was screened. As a result, 2 positive plaques were obtained by using the probe NZ4 while 1 positive plaque was obtained by using the synthetic oligonucleotide probe. Each screening was repeated until all of the plaques became positive.
4) Extraction of λDNA Each positive clone was propagated by using *Escherichia coli* LE392 as the host in accordance with the method described in Example 2 and then DNA was extracted.

(5) Partial Mapping and Sequencing

The λDNAs obtained in the above (4) (GHFc-1, 2 and 3) were completely digested with restriction enzymes (ApaI, BamHI, EcoRI, HindIII, KpnI, NcoI, PstI, SacI, ScaI, SmaI, SpeI, SphI, StuI, XbaI and XhoI), electrophoresed on a 1% agarose gel and then subjected to Southern blotting. Then each gel was immersed in 0.25 N HCl for 30 minutes and allowed to stand under shaking in a denaturation buffer (0.4 N NaOH/1.5 M NaCl) at room temperature for 15 minutes twice. Subsequently, it was further allowed to stand under shaking in a neutralization buffer (1 M NH$_4$OAc/0.02 N NaOH) at room temperature for 15 minutes twice. Next, each gel was transferred onto 2 nylon membrane (bidirectional transfer) and these 2 membranes were subjected to hybridization respectively with the probe NZ4 and the synthetic oligonucleotide probe.

Positive fragments of GHFc-1, 2 (ApaI, EcoRI, SacI and XhoI) and GHFc-3 (BamHI, EcoRI and XbaI) were subcloned into a pBluescript vector (manufactured by Toyobo) and subjected to partial sequencing. The sequencing was carried out in accordance with the method of Example 6.
(6) Result As the results of the partial mapping and sequencing, it was found out that the clones GHFc-1, 2 and 3 were independent clones having inserts of about 15 kb (GHFC-1 and 2) and 13 kb (GHFc-3) and GHFc-1 partly overlapped GHFc-2. Introns satisfying the GT/AG rule were located between the bases at the 63- and 64-positions and those at the 1311- and 1312-positions of the cDNA of FcγBP (FIG. 10) and the base sequence of the exon region up to the 1311-position was completely identical with that of the cDNA (FIG. 11).

Further, the sequence located 5' upstream of the cDNA clone NZ4 was contained in GHFc-3 and the stop codon (TGA) in frame was located 87 bases upstream from the assumed translation initiation codon ATG described in Example 7 (i.e., 79 bases upstream from the 5' end of NZ4 represented by SEQ ID NO:1). No other ATG in frame was observed any more. These results strongly support the possibility that the ATG starting from the base at the 9-position in the clone NZ4 is the translation initiation ATG of the FcγBP gene.

Example 18

Correlation Between Structure of Human FcγBP and IgG Fc Region-binding Activity

Figure 12:
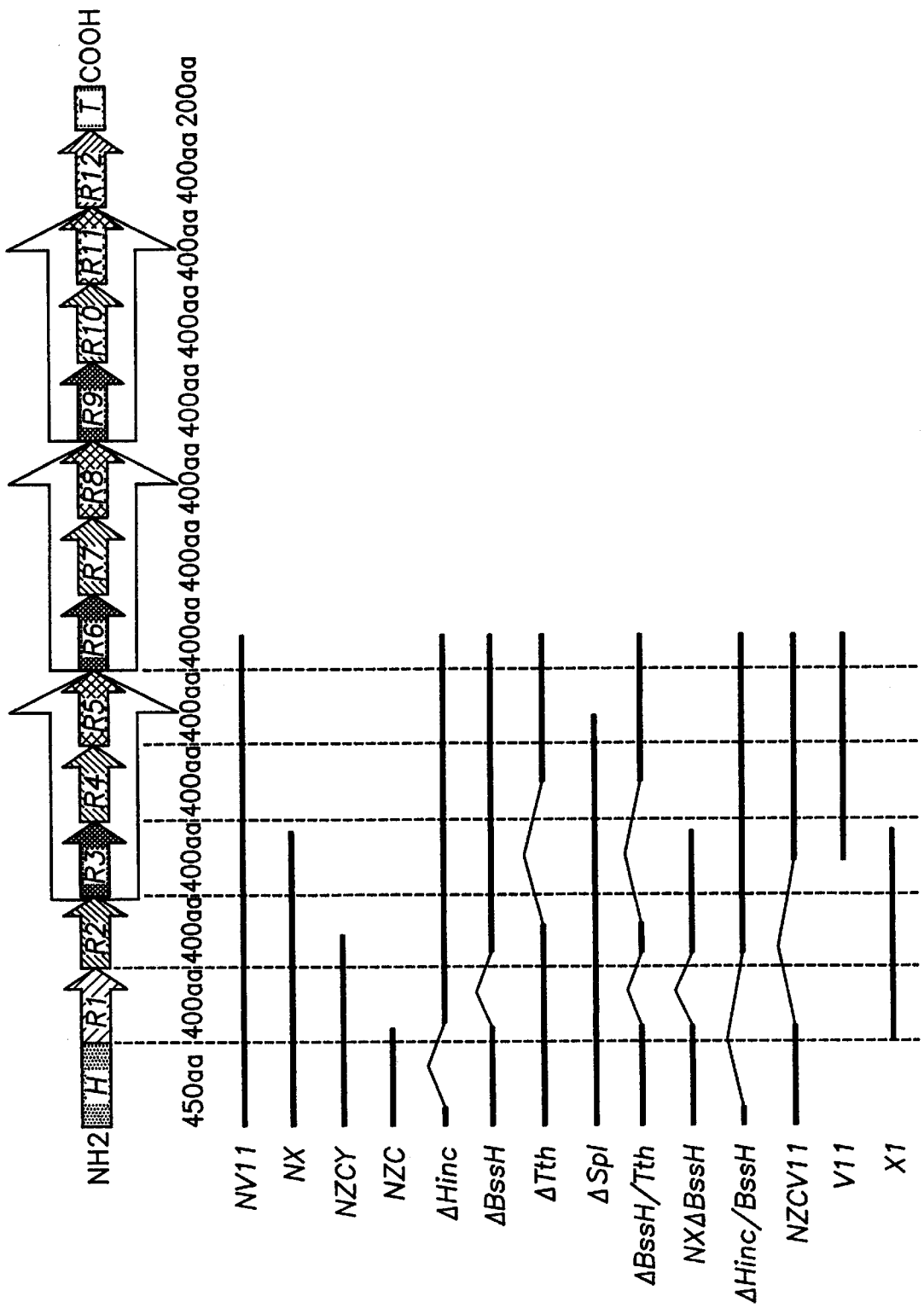
FIG. 12 shows the structure of human FcγBP and the locations therein corresponding to the clones employed in the present invention.

The protein structure having the amino acid sequence assumed from the entire base sequence of the cDNA of FcγBP obtained so far is one having a unique sequence in which a unit consisting of about 400 amino acid residues is repeated 12 times in total (R1–R12 domain) and a sequence consisting of about 450 amino acids (H domain) and another sequence consisting of about 200 amino acid (T domain) are located before and after the R1–R12 part. As FIG. 12 shows, among the repeating units in the R domain, the units R3, R6 and R9 have a homology of at least 95% with each other. Similarly, the units R4/R7/R10 and R5/R8/R11 ave each a homology of at least 95%. On the other hand, he units R1 to R5 have a homology of about 40% with each other. To discuss the function of these protein domains, mutated clones having some defects in the cDNA were separated and expressed in COS cells. Thus the functions including the activity of binding to IgG, etc. were examined.

As FIG. 12 shows, the partial cDNA plasmid pNV11, which had been expressed in animal cells in order to determine the Fc-binding activity, was composed of H, R1, R2, R3, R4, R5 and a part of R6. To clarify the unit having the Fc-biding activity, the following experiment was carried out. Namely, cDNA fragments, from which some part of NV11 had been deleted by cleaving and/or rebinding with restriction enzymes or ligating appropriate clones with each other so as to suit for an amino acid frame, were inserted into an expression vector SRα and then *E. coli* XL-1 was transformed thereby. Table 1 shows the sequences after the deletion of a part of NV11 expressed in the DNA base numbers. In the cDNA of NV11, the first base from which the translation into protein is initiated is referred to as No. 1 while the final base is referred to as No. 7776.

The expression vector containing each cDNA fragment was purified from *Escherichia coli*, tentatively expressed in COS7 cells in the same manner as the one of Example 11 and then stained with human IgG Fc region and the monoclonal antibodies K9 and K17 specific to FcγBP.

Further, the following staining was effected in order to examine the inhibition of the binding to the IgG Fc region by the monoclonal antibodies. The COS7 cells having cDNA tentatively expressed therein were fixed with ethanol. Then thermally denatured human IgG was diluted with hybridoma culture supernatants containing either or both of the inhibition antibodies K9 and K17 or antiFcγRIII (a control antibody) so as to give each a concentration of 1 μg/ml. Then the fixed cells were incubated together with each supernatant. After allowing to stand at room temperature for 1 hour and washing with PBS (−), the cells were further incubated together with HRP-labeled antihuman IgG (H+L) antibody F(ab7)$_2$ fragment and then the biding of the denatured IgG was detected.

The results are as follows. To examine whether or not the gene expression product had IgG Fc region-binding activity, human IgG was employed as the primary antibody while the HRP-labeled antihuman IgG antibody was employed as the secondary antibody. IgG-binding activity was observed in the clones having the entire sequence of the H domain and, furthermore, the entire region of at least one R unit (NV11, NX, NZCY, ΔBSSH, ΔTth, ΔSp1, ΔBssH/Tth, NXΔBssH and NZCV11). The strength of the stain indicating the IgG-binding activity was tend to increase with an increase in the number of R units contained in the clone. However, the clones from which the H domain had been completely or partly deleted (ΔHinc, ΔHinc/BssH, V11 and X1) and the clone having only a part of a R unit (NZC) showed no IgG-binding activity.

Regarding the staining of the gene products with the monoclonal antibodies, on the other hand, the clones having the entire or partial sequence of R5 (NV11, ΔHinc, ΔBssH, ΔTth, ΔSp1, ΔBssH/Tth, ΔHinc/BssH, NZCV11 and V11) were stained with the monoclonal antibody K9, while the clones having the entire or partial sequence of R3 or R6 (all clones except NZCY and NZC) were stained with the monoclonal antibody K17. These results indicated that in the clones lacking the H domain (ΔHinc/BssH, V11 and X1), no IgG-binding activity could be achieved, though the proteins reacting with the FcγBP-specific antibodies were produced therein. Thus it is suggested that the H domain would have a function essentially required in imparting the IgG-binding activity to the R domain products. The clone NZC showed no IgG-binding activity and was negative in the K9/K17 staining, which suggests that the R units (R1 to R5) might correspond to the IgG-binding site.

Subsequently, the results of the inhibition of the IgG-binding by the monoclonal antibodies K9 and K17 will be reported. Table 1 summarizes the inhibitory effects on each clone.

(1) The IgG-binding activities of the clones having at least one R unit in addition to R3 and R5 (NV11, ΔTth and NZCV11) were inhibited to a certain extent by K9 or K17. When these antibodies were added together, the inhibition was strengthened, though complete inhibition did not occur.

(2) The IgG-binding activity of the clone having at least one R unit in addition to R3 (NX) was inhibited by K17 not completely but to a certain extent. The activity of this clone was never inhibited by K9.

(3) The IgG-binding of the clone containing R3 alone (NXΔBssH) was completely inhibited by K17. In contrast, the binding was not affected by K9.

(4) The IgG-binding of the clone containing R5 alone (ΔBssH/Tth) was completely inhibited by K9. In contrast, the binding was not affected by K17.

(5) Both of K9 and K17 did not inhibit the IgG-binding of the clone containing neither R3 nor R5 (NZCY).

(6) The inhibition of the IgG-binding by the control antibody (antiFcγRIII antibody) was observed in none of the clones.

Based on these results, it is assumed that the IgG Fc binding sites are located in the R1–R5 region including R3 and R5 and each R unit can bind to IgG independently. Also, there is pointed out a possibility that 2 or more IgGs might be bound to cDNA clones having 2 or more R units (NV11, etc). These facts suggest that each of R1 to R12 might have the IgG binding site by taking the homology in the amino acid sequences into consideration.

TABLE 1

EXPRESSION TABLE

| Clone | Base No. | Avidity to monoclonal antibody | | IgG-binding | | | |
|---|---|---|---|---|---|---|---|
| | | K9 | K17 | no antibody | +K9 | +K17 | +K9 + K17 |
| NV11 | 1–7776 | + + + | + + + | + + + | + + | + + | + |
| NX | 1–4692 | − | + + + | + + | + + | + | + |
| NZCY | 1–3013 | − | − | + | + | + | + |
| NZC | 1–1473 | − | − | − | | | |
| ΔHinc | 1–271, 1657–7776 | + + + | + + + | − | | | |
| ΔBssH | 1–1600, 2761–7776 | + + + | + + + | + + | | | |
| ΔTth | 1–3272, 5477–7776 | + + + | + + + | + + + | + + | + + | + |
| ΔSp1 | 1–6066 | + + + | + + + | + | | | |

TABLE 1-continued

EXPRESSION TABLE

| Clone | Base No. | Avidity to monoclonal antibody | | IgG-binding | | | |
|---|---|---|---|---|---|---|---|
| | | K9 | K17 | no antibody | +K9 | +K17 | +K9 + K17 |
| ΔBssH/Tth | 1–1600, 2761–3272, 5477–7776 | +++ | +++ | ++ | – | ++ | – |
| NXΔBssH | 1–1600, 2761–4692 | – | +++ | + | + | – | – |
| ΔHinc/BssH | 1–271, 2761–7776 | +++ | +++ | – | | | |
| NZCV11 | 1–1473, 4165–7776 | +++ | +++ | +++ | ++ | ++ | + |
| V11 | 4165–7776 | – | +++ | – | | | |
| X1 | 1445–4692 | – | +++ | – | | | |

Example 19

Partial Analysis of FcγBP Genome Gene
(determination of transcription initiation site)

Based on the results of the primer extension carried out in Example 7, it was assumed that the transcription initiation site might be located within 20 bases upstream from the clone NZ4 which was located at the 5'-uppermost stream at the present stage; and that the ATG at the 9-position in NZ4 might be the translation initiation site. To examine whether or not ATG in frame or the stop codon was located upstream from NZ4, therefore, the FcγBP gene was isolated from the genomic DNA library and its partial base sequence was identified.

Further, the transcription initiation site was more accurately determined by S1 mapping.

(1) Genomic DNA Library

As the library, use was made of a commercially available one originating in human leukocytes (Vector, EMBL3 SP6/T7, manufactured by Clontech).

(2) Probe

As the probes to be employed in the screening, use was made of one prepared by excising the cDNA clone NZ4 from the vector with BamHI and the synthetic oligonucleotide employed in Example 7 (primer 2: (GCTCCAGCCCAGAGTATCCACCAGCTCCATAGG-33 mer, SEQ ID NO:11) labeled respectively with α[$^{32}$P] dCTP and γ[$^{32}$P] ATP by random prime labeling (NZ4) or end labeling (primer 2).

(3) Screening

The screening with the probe NZ4 was performed in accordance with the method for screening a cNDA library as described in Example 4. In the screening with the synthetic oligonucleotide probe, on the other hand, the formamide concentration of the hybridization solution was adjusted to 20% and washing was repeated 5 times in a solution containing 0.3×SSC/0.1% of SDS at 45° C. each for 30 minutes.

With each probe, a library of 1,000,000 clones was screened. As a result, 2 positive plaques were obtained by using the probe NZ4 while 1 positive plaque was obtained by using the synthetic oligonucleotide probe. Each screening was repeated until all of the plaques became positive.

(4) Extraction of λDNA

Each positive clone was propagated by using *Escherichia coli* LE392 as the host in accordance with the method described in Example 2 and then DNA was extracted.

(5) Partial Mapping and Sequencing

The λDNAs obtained in the above (4) (GHFc-1, 2 and 3) were completely digested with restriction enzymes (ApaI, BamHI, EcoRI, HindIII, KpnI, NcoI, PstI, SacI, ScaI, SmaI, SpeI, SphI, StuI, XbaI and XhoI), electrophoresed on a 1% agarose gel and then subjected to Southern blotting. Then each gel was treated with 0.25 N HCl, 0.4 N NaOH/1.5 M NaCl and 1 M NH$_4$Ac/0.02 N NaOH each for 15 minutes twice. Next, each gel was transferred onto 2 nylon membrane (bidirectional transfer) and these 2 membranes were subjected to hybridization respectively with the probe NZ4 and the synthetic oligonucleotide probe.

Positive fragments of GHFc-1, 2 (ApaI, EcoRI, SacI and XhoI) and GHFc-3 (BamHI, EcoRI and XhoI) were subcloned into a pBluescript vector (manufactured by Toyobo) and subjected to partial sequencing. The sequencing was carried out in accordance with the method of Example 6.

(6) S1 Mapping

As a template for constructing an S1 probe, use was made of ssDNA which had been prepared by subcloning the EcoRI/SacI fragment (corresponding to about 2 kb upstream from NZ4 in cDNA clone) of the clone GHFc-3 into pBluescript SK$^+$ and treated with a helper phage VCSM13. To this template was annealed the labeled primer 2 employed in the primer extension followed by synthesis with BcaBEST polymerase (manufactured by Takara) at 65° C. for 10 minutes. Then the synthesis product was digested with BamHI, thermally denatured and separated by using a 7.5% polyacrylamide gel containing 8 M of urea. Then the target gel was excised. The gel thus excised was incubated in G buffer (1M of NH$_4$AC, 20 mM of Mg(OAc)$_2$, 0.1 M of EDTA, 0.2% of SDS, 10 μg/ml of yeast tRNA) at 37° C. overnight to thereby eluate the probe. This S1 probe (1×10$^5$ cpm) was mixed with 40 μg of all RNAs originating inhuman colonic epithelial cells and 1.5 μg of polyA $^+$RNA. After precipitating from ethanol, the precipitate was dissolved in 20 μl of an S1 hybridization solution (80% of formamide, 40 mM of PIPES, 400 mM of NaCl, 1 mM of EDTA). After treating at 80° C. for 10 minutes, it was subjected to hybridization at 42° C. overnight. Then 200 μl of an S1 solution [30 mM of NaOAc (pH 4.6), 280 mM of NaCl, 1 mM of ZnSO$_4$, 1 mg/ml of ssDNA, 150 U of S1 nuclease] was added thereto followed by digestion at 37° C. for 40 minutes. Next, it was electrophoresed on a 6% sequence gel and the gel was fixed, dried and subjected to autoradiography.

RESULTS AND DISCUSSION

As the results of the partial mapping and sequencing, it was found out that the clones GHFc-1, 2 and 3 were independent clones having inserts of about 15 kb (GHFc-1 and 2) and 13 kb (GHFc-3) and GHFc-1 partly overlapped GHFc-2. Introns satisfying the GT/AG rule were located between the bases at the 63- and 64-positions and those at the 1311- and 1312-positions of the cDNA of FcγBP and the base sequence of the exon region up to the 1311-position was completely identical with that of the cDNA (FIGS. 10 and 11). Further, the sequence 5' upstream from the cDNA clone NZ4 was contained in GHFc-3 and the stop codon (TGA) in frame was located 87 bases upstream from the assumed translation initiation codon ATG described in Example 7 (i.e., 79 bases upstream from the 5' end of NZ4). No other ATG in frame was observed any more. These results strongly support the possibility that the ATG starting from the base at the 9-position in the clone NZ4 is the translation initiation ATG of the FcγBP gene. Further, no typical promoter motif (TATA/CCAAT, etc.) was contained within about 2 kbp 5'-upstream from NZ4. The results of the S1 mapping indicated that bands of the corresponding lengths were observed 8, 9 and 10 bases upstream from this ATG. Among these bands, the one of the A residue at the 10-position showed the strongest signal, which suggests that the transcription would be initiated from this A residue.

Example 20

Analysis of Polymorphism of FcγBP Gene

As the result of the sequencing of the cDNA of FcγBP, it was suggested that polymorphism occurred at specific sites in the coding region. Namely, the sequence CCCGGG at the SmaI sites located on the 5120-, 8723- and 12326-positions in the cDNA of FcγBP were replaced by CCTGGG in the same region of the clone A52. The library employed in the screening of the cDNA originated in genes of not a single person but several subjects. Accordingly, the following experiment was carried out in order to confirm whether the above-mentioned base replacement was observed among individuals or in the major repeating region (thrice) per haploid genome in a single individual.

The following 2 primers were synthesized as the primers on the forward side:

BC1: ACCACTCCTTCGATGGCC, SEQ ID NO:24, and
GS1: ACCTGTAACTATGTGCTGGC, SEQ ID NO:25.

On the other hand, the following 4 primers were synthesized as the primers on the reverse side:

GS2: TGGTGGTGACGGTGAAGGG, SEQ ID NO:26,
GS3: ACAGCAGGGTTGCCCCGG, SEQ ID NO:27,
GS4: TGGTGCCGAGGGCAGCCACG, SEQ ID NO:28, and
BC2: TGGGTCACTGAAATCCG, SEQ ID NO:29.

Further, leukocytes of 6 healthy subjects and colonic epithelial cells of normal parts of 4 patients with cancer were separated and DNAs were extracted therefrom by the method of Nelson et al. To 20 ng of each DNA was added primer sets BC1/BC2, BC1/GS3, BC1/GS4, GS1/GS3 and GS1/GS4 to give each a final concentration of 20 pmole. Then PCR was performed in a PCR buffer [10 mM of Tris-HCl (pH 8.3), 50 mM of KCl, 1.5 mM of $MgCl_2$, 200 μM of dNTPs, 0.001% of gelatin, 2.5 U of taq polymerase] in 30 cycles each cycle consisting of 94° C. for 1 minute, 60° C. for 1.5 minutes and 72° C. for 2.5 minutes. The PCR products were digested with SmaI, electrophoresed on a 2% agarose gel and then stained with EtBr.

As the results of the SmaI-treatment of the PCR products for the primer sets, it was found out that polymorphism was observed in each of the primer sets except BC1/BC2.

Namely, from among 10 DNA samples, one was completely digested with SmaI. Accordingly, this sample had the SmaI sites at last in all of the 6 repeating units involving the allele. In contrast, SmaI-digested products and undigested products were observed at various ratios in other samples. On the contrary, none of these 10 samples was free from any SmaI site. Furthermore, RT-PCR was performed in HT-29N2 cells by using the same primer sets followed by digestion with SmaI. As a result, all of the samples contained the sites.

The primers BC1/BC2 showed no polymorphism. This is seemingly because the PCR product had a chain length of about 1.8 kbp and thus there was an intron (about 1.6 kbp) between the primer GS4 and the primer BC2 and the samI site was located on the 5' side of this intron. Thus it was assumed that no polymorphism was detected since the above-mentioned site was extremely close to the target SmaI site showing polymorphism and the BC1/BC2 amplification product was scarcely different in chain length from the SmaI-digestion product.

Example 21

Separation of High Expression-inducible CHO Cell Line and Detection of FcγBP

In order to establish a cell line capable of expressing a large mount of the FcγBP fragment described in Example 11 in a stable state, NV11ST (i.e., the partial FcγBP cDNA) was expressed by using an expression vector pMSXND for animal cells. The vector pMSXND is one having a metal-lothionein promoter, which can induce the expression of a protein with sodium butyrate, etc., as an expression promoter and being constructed in such a manner as to have dhfr gene which enables gene amplification after being integrated into chromosomal DNA.

(1) Alteration of Vector pMSXND

First, the plasmid was completely digested with XhoI corresponding to the cDNA cloning site of pMSXND. Subsequently, it was blunt-ended by treating with 0.4 U of Klenow fragment for 15 minutes.

Next, NotI linker (5'-pGCGGCCGC-3') was ligated to the vector followed by complete digestion with NotI. After the completion of the autoligation, competent E. coli XL1-B was transformed thereby. The clones thus obtained were analyzed to thereby give a plasmid pMSXND-NOT in which the NotI linker had been inserted into the XhoI site of pMSXND.

(2) Insertion of cDNA pMSND-NOT was completely digested with NotI and then dephosphorylated by treating with alkaline phosphatase. Next, the plasmid pNV11-ST, which was prepared in Example 6-(6) and had FcγBP cDNA integrated thereinto, was completely digested with NotI and electrophoresed on an agarose gel to thereby separate and recover a cDNA fragment of 8 kbp. These expression vectors were ligated to the cDNA insert and competent E. coli (XL1-B) was transformed thereby. From the colonies formed by incubating the transformant on an LB plate containing ampicillin, a plasmid in which cDNA had been inserted in the sense direction to the metallothionein promoter was selected and referred to as pNV11-MSX.

(3) Expression of Partial cDNA of IgG FcBP Region in CHO Cell

Escherichia coli containing the plasmid pNV11-MSX was incubated in the same manner as the one described in Example 11 and the plasmid thus amplified was purified. Then 10 μg of this plasmid dissolved in 250 μl of F-12 medium (containing nucleotide) was mixed with 10 μl of a lipofection reagent (Transfectum, manufactured by Sepacor) dissolved in 250 μl of F-12 medium and the resulting mixture was immediately added onto CHO cells (dhfr-deficient line). After incubating at 37° C. for 6 hours, the medium was replaced by F-12 medium containing 10% of serum and the incubation was continued for 3 days. Next, the medium was replaced by α-MEM medium (nucleotide-free, manufactured by Gibco) containing 1 mg/ml of G418 and 10% of fetal bovine serum. Then incubation was carried out for 14 days while replacing the medium at intervals of 3 days. Next, cells having the plasmid inserted thereinto were selected. Thus the cells were cloned by the limiting dilution analysis from a dish in which several ten colonies had been formed. Among the cell clones thus obtained, those showing the expression of the protein with high Fc-binding activity were selected. Subsequently, gene amplification was carried out in order to elevate the expression yield.

(4) Gene Amplification

The integrated gene was amplified by treating with methotrexate so as to elevate the expression yield of the protein by the cell clone which had pNV11-MSX integrated into the chromosome of CHO cells and was capable of stably expressing the FcγBP fragment.

Namely, the above-mentioned cell clone showing stable expression was incubated in A-MEM medium (nucleotide-free) containing 0.005 μM of methotrexate and 500 μg/ml of G418 for 3 to 4 weeks and the cells thus grown were selected. Next, the methotrexate concentration was elevated 4-fold (0.02 μM) and the incubation was continued in the same manner for additional 3 to 4 weeks. The procedure of elevating the methotrexate concentration 4-fold followed by incubation was repeated to thereby finally give cells propagated in the presence of 6.4 to 25 μM of methotrexate. These cells were cloned by the limiting dilution analysis to thereby give a cell line with high expression of the FcγBP fragment. Similar to Examples 11 and 12, the increase in the expression yield was determined by the primary judgement by histochemical staining with the monoclonal antibodies K9/K17 or the detection of the IgG-binding activity.

(5) Preparation of Cell Sample $5 \times 10^5$ cells of the CHO cell line, which could stably express the FcγBP fragment at a high yield, were transferred into a dish (diameter: 100 mm) and incubated in α-MEM medium containing 6.4 μM of methotrexate and 1 mg/ml of G418. If necessary, sodium butyrate was added in such an amount as to give a final concentration of 5 mM to thereby induce the expression of the protein. After 3 days, the culture supernatant (SUPL) was recovered. Then the SUP1 was centrifuged at 100,000×g for 60 minutes to thereby eliminate cell pieces therefrom and the supernatant (SUP2) was recovered. The cells were suspended in 500 μl of a cytolysis buffer [50 mM of Tris-HCl (pH 7.5), 150 mM of NaCl, 1 mM of EDTA, 1 mM of PMSF, 10 mM of monoiodo acetamide, 10 μg/ml of approtinine, 10 μg/ml of leupeptin] and subjected to ultrasonication (30 seconds×3 times) and centrifugation at 10,000×g for 10 minutes at 4° C. After the completion of the centrifugation, the supernatant (LYS1) was eliminated. To the residue was added 400 μl of the cytolysis buffer containing 1% of NP-40 followed by ultrasonication and centrifugation. After recovering the supernatant (LYS2), the residue was dissolved in 200 μl of the cytolysis buffer containing 1% of NP-40, 0.1% of SDS and 0.5% of sodium deoxycholate followed by ultrasonication and centrifugation. After recovering the supernatant (LYS3), the residue was dissolved in 100 μl of the cytolysis buffer (LYS4). As a control, use was made of solutions of colonic epithelial cells (diluted 100- to 3,200-fold).

(6) Sandwich ELISA

To quantitatively detect the FcγBP fragment thus produced, a sandwich ELISA system with the use of the monoclonal antibodies K9 and K17 specific for FcγBP was developed. The antibody K9 purified by affinity chromatography was dissolved in a 0.05 M carbonate buffer (pH 9.2) in such a manner as to give a concentration of 5 μg/ml and added to an ELISA plate (PRO-BIND, manufactured by Falcon) at a ratio of 50 μl/well. After allowing to stand at 4° C. overnight, the wells were washed with a washing liquor [PBS (−) containing 0.05% of Tween-20] thrice. Then 50 μl/well of a blocking solution (RPMI 1640 medium containing 10% of serum) was added and the plate was allowed to stand at room temperature for 60 minutes.

After eliminating the blocking solution, 50 μl portions of the samples prepared in the above (5) were added and the plate was allowed to stand at room temperature for 2 hours. After washing with the washing liquor thrice, 50 μl of HRP-labeled K17 antibody, which had been diluted with the blocking solution to give a concentration of 4 mg/ml, was added and the plate was allowed to stand at room temperature for 1 hour. Then it was washed with the washing liquor thrice and 50 μl of a color development solution [20 mg of o-phenylenediamine and 80 μl of $H_2O_2$ (30%) dissolved in 50 ml of citrate buffer] was added thereto followed by the color development at room temperature for 3 minutes. Subsequently, the reaction was ceased by adding 50 μl of a 2.5 M $H_2SO_4$ solution and the absorbance at 492 nm was measured.

RESULT (i) Typical CHO Cell Line Showing FcγBP Expression Obtained Above

Figure 13A:
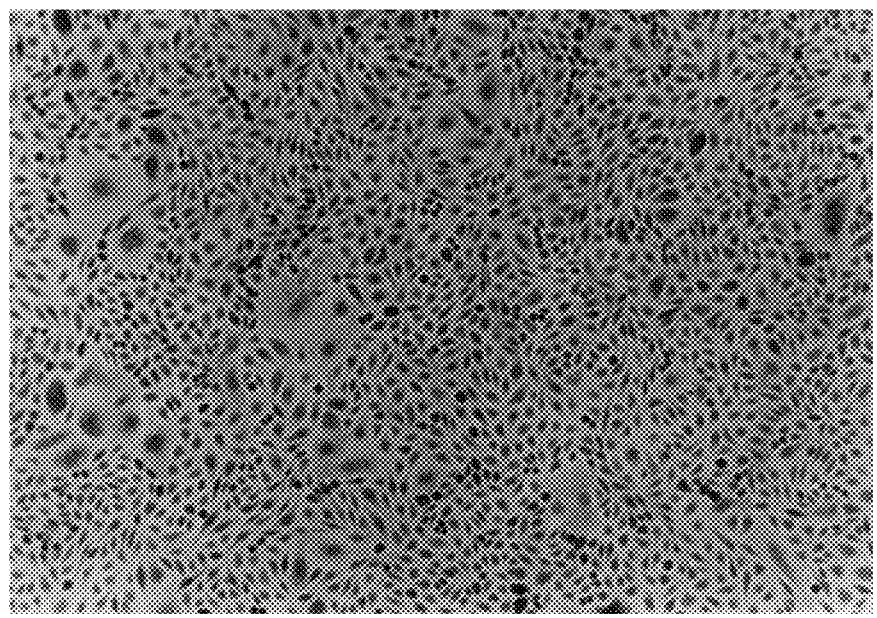
FIGS. 13A–13B provide morphological photographs showing CHO cells expressing the FcγBP fragment therein. The sample (13A) had been treated with 6.4 μM of methotrexate but no sodium butyrate, while the sample (13B) had been treated with 6.4 μM of methotrexate and 5 mM of sodium butyrate.
Figure 13B:
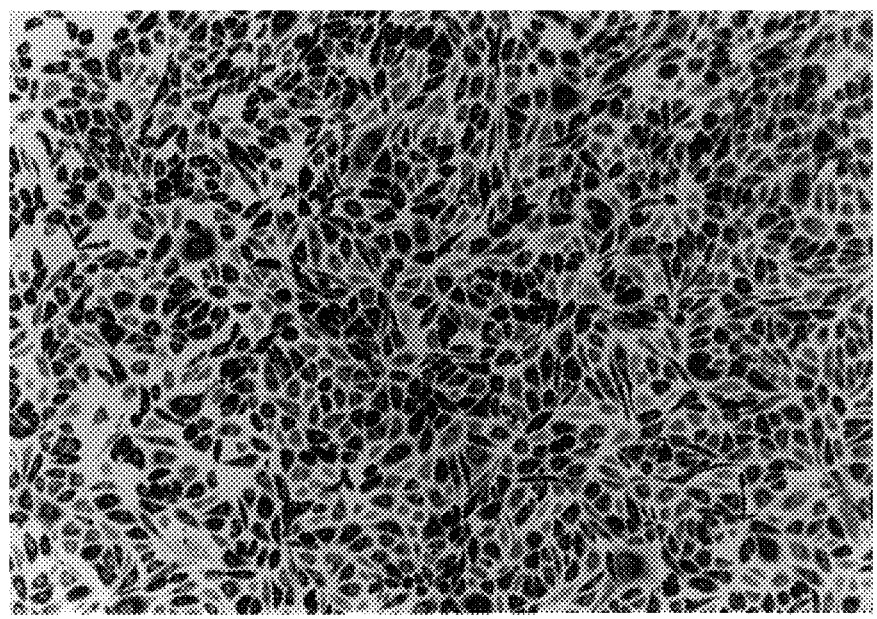

After incubating in the presence of methotrexate optionally followed by the treatment with sodium butyrate, the expression yield of the FcγBP fragment after 3 days was detected by the cell staining method with the use of the monoclonal antibodies K9/K17. Thus a cell line with a high expression yield could be isolated as shown in FIG. 13.

(ii) Result of Determination of FcγBP Fragment by ELISA

The samples obtained from the cell line with a high expression yield of the FcγBP fragment were subjected to sandwich ELISA. As a result, the cytolysis solutions (LYS1 to LYS4) contained the FcγBP fragment in larger amounts than the culture supernatants (SUP1 and SUP2), as shown in the absorbances listed in the following Table 2. This fact indicates that the FcγBP fragment thus expressed is not accumulated in the cells but secreted out therefrom.

TABLE 2

| Sample | | $OD_{492}$ |
|---|---|---|
| colonic epithelial cell lysate (control) | dilution | |
| | 100-fold | 2.184 |
| | 200 | 2.024 |
| | 400 | 1.516 |
| | 800 | 0.935 |
| | 1600 | 0.514 |
| | 3200 | 0.264 |
| expression-induced cell | SUP1 | 0.731 |
| | SUP2 | 0.712 |
| | LYS1 | 0.044 |
| | LYS2 | 0.174 |
| | LYS3 | 0.013 |
| | LYS4 | 0.095 |
| expression-uninduced cell | SUP1 | 0.259 |
| | SUP2 | 0.273 |
| | LYS1 | 0.027 |
| | LYS2 | 0.070 |
| | LYS3 | 0.012 |
| | LYS4 | 0.019 |

What is claimed is:

1. An isolated DNA comprising a base sequence encoding the amino acid sequence represented by SEQ ID NO:7 or a base sequence hybridizable therewith in 5×SSPE, 5×Denhardt's solution, 50% formamide, 0.5% SDS, 100 µg/ml salmon sperm DNA, at 42° C. and washed with 0.2×SSC and 0.2% SDS at 65° C., wherein said hybridizing base sequence encodes a polypeptide which binds to the Fc region of IgG.

2. A DNA as claimed in claim 1 which has been inserted into a plasmid pNV11-ST (FERM BP-4625).

3. An isolated DNA comprising a base sequence encoding the amino acid sequence represented by SEQ ID NO:9 or a base sequence hybridizable therewith in 5×SSPE, 5×Denhardt's solution, 50% formamide, 0.5% SDS, 100 μg/ml salmon sperm DNA, at 42° C. and washed with 0.2×SSC and 0.2% SDS at 65° C., wherein said hybridizing base sequence encodes a polypeptide which binds to the Fc region of IgG.

4. A recombinant vector containing the DNA as claimed in claim 1 or 3.

5. Procaryotic or eucaryotic host cells transformed by a recombinant vector as claimed in claim 4.

6. A process for producing a recombinant protein which comprises incubating host cells as claimed in claim 5 and separating and purifying the protein thus produced.

7. A method for identifying a tissue synthesizing mRNA of the IgG Fc region-binding protein by Northern blotting or in situ hybridization with the use of a DNA as claimed in claim 1 or 3 as a probe.

8. An isolated DNA comprising:

a) an H (nucleotides 9–1352 of SEQ ID NO:8) region and one or more regions selected from the group consisting of R1 (nucleotides 1353–2528 of SEQ ID NO:8), R2 (nucleotides 2529–3692 of SEQ ID NO:8), R3 (nucleotides 3693–4955 of SEQ ID NO:8), R4 (nucleotides 4956–6149 of SEQ ID NO:8), R5 (nucleotides 6150–7295 of SEQ ID NO:8), R6 (nucleotides 7296–8558 of SEQ ID NO:8), R7 (nucleotides 8559–9752 of SEQ ID NO:8), R8 (nucleotides 9753–10898 of SEQ ID NO:8), R9 (nucleotides 10899–12161 of SEQ ID NO:8), R10 (nucleotides 12162–13355 of SEQ ID NO:8), R11 (nucleotides 13356–14504 of SEQ ID NO:8) and R12 (nucleotides 14505–15767 of SEQ ID NO:8); or b) an isolated DNA which hybridizes to said DNA of a) in 5×SSPE, 5×Denhardt's solution, 50% formamide, 0.5% SDS, 100 μg/ml salmon sperm DNA, at 42° C. and washed with 0.2×SSC and 0.2% SDS at 65° C., wherein said hybridizing base sequence encodes a polypeptide which binds to the Fc region of IgG.

9. An isolated DNA sequence encoding a protein of SEQ ID NO:7 or 9.

10. An isolated DNA comprising:

an H (nucleotides 9–1352 of SEQ ID NO:8) region and one or more regions selected from the group consisting of R1 (nucleotides 1353–2528 of SEQ ID NO:8), R2 (nucleotides 2529–3692 of SEQ ID NO:8), R3 (nucleotides 3693–4955 of SEQ ID NO:8), R4 (nucleotides 4956–6149 of SEQ ID NO:8), R5 (nucleotides 6150–7295 of SEQ ID NO:8), R6 (nucleotides 7296–8558 of SEQ ID NO:8), R7 (nucleotides 8559–9752 of SEQ ID NO:8) R8 (nucleotides 9753–10898 of SEQ ID NO:8), R9 (nucleotides 10899–12161 of SEQ ID NO:8), R10 (nucleotides 12162–13355 of SEQ ID No:8), R11 (nucleotides 13356–14504 of SEQ ID NO:8) and R12 (nucleotides 14505–15767 of SEQ ID NO:8) wherein said DNA encodes a protein which binds to the IgG Fc region.

* * * * *